(12) United States Patent
Roe

(10) Patent No.: US 11,896,810 B2
(45) Date of Patent: Feb. 13, 2024

(54) INJECTION MONITORING DEVICE WITH DELIVERY SIGNATURE

(71) Applicant: Genentech, Inc., South San Francisco, CA (US)

(72) Inventor: Steven N. Roe, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 18/066,800

(22) Filed: Dec. 15, 2022

(65) Prior Publication Data

US 2023/0398305 A1 Dec. 14, 2023

Related U.S. Application Data

(63) Continuation of application No. 16/912,560, filed on Jun. 25, 2020, now Pat. No. 11,565,054, which is a continuation of application No. PCT/US2018/067580, filed on Dec. 27, 2018.

(60) Provisional application No. 62/612,147, filed on Dec. 29, 2017.

(51) Int. Cl.
*A61M 5/00* (2006.01)
*A61M 5/315* (2006.01)
*G16H 20/17* (2018.01)

(52) U.S. Cl.
CPC ...... *A61M 5/3157* (2013.01); *A61M 5/31536* (2013.01); *G16H 20/17* (2018.01); *A61M 2205/332* (2013.01); *A61M 2205/3553* (2013.01); *A61M 2205/8206* (2013.01)

(58) Field of Classification Search
CPC ............ A61M 5/3157; A61M 5/31536; A61M 2205/332; A61M 2205/3553; A61M 2205/8206; G16H 20/17
USPC ......................................................... 604/208
See application file for complete search history.

(56) References Cited

U.S. PATENT DOCUMENTS

| 11,565,054 | B2 | 1/2023 | Roe |
| 2011/0009821 | A1 | 1/2011 | Jespersen et al. |
| 2011/0131395 | A1* | 6/2011 | Georgiades ............. G06F 7/724 712/E9.017 |
| 2014/0194825 | A1 | 7/2014 | Nielsen et al. |
| 2016/0030683 | A1* | 2/2016 | Taylor ................... A61M 5/345 604/151 |
| 2016/0074587 | A1 | 3/2016 | Searle et al. |
| 2016/0259913 | A1 | 9/2016 | Yu et al. |
| 2017/0007765 | A1 | 1/2017 | Cowe et al. |
| 2020/0261652 | A1* | 8/2020 | Cowe .................. A61M 5/3157 |

FOREIGN PATENT DOCUMENTS

| CN | 104703641 A | 6/2015 |
| CN | 105007961 A | 10/2015 |
| CN | 106039482 A | 10/2016 |
| EP | 3184137 A1 | 6/2017 |

(Continued)

*Primary Examiner* — Tai T Nguyen
(74) *Attorney, Agent, or Firm* — Shay Glenn LLP

(57) ABSTRACT

Drug delivery systems and methods of use thereof for recording administration of a drug dose to a subject are provided. Aspects of the invention include a syringe stopper rod comprising a sensor component that is configured to detect a delivery signature, and to transmit a report comprising a drug dose completion signal to a data management component, e.g., a mobile computing device.

33 Claims, 48 Drawing Sheets

(56) References Cited

FOREIGN PATENT DOCUMENTS

| | | | |
|---|---|---|---|
| JP | 2017536177 | A | 12/2017 |
| TW | 201729852 | A | 9/2017 |
| WO | WO2007/126851 | A2 | 11/2007 |
| WO | WO2008/037138 | A1 | 3/2008 |
| WO | WO2009/024562 | A1 | 2/2009 |
| WO | WO2013/054165 | A1 | 4/2013 |
| WO | WO2016/005421 | A1 | 1/2016 |
| WO | WO2016/078863 | A1 | 5/2016 |
| WO | WO2016/087512 | A1 | 6/2016 |
| WO | WO2016/115372 | A1 | 7/2016 |
| WO | WO2016/128207 | A1 | 8/2016 |
| WO | WO2016/180873 | A1 | 11/2016 |
| WO | WO2017/001923 | A1 | 1/2017 |
| WO | WO2017/071983 | A1 | 5/2017 |

\* cited by examiner

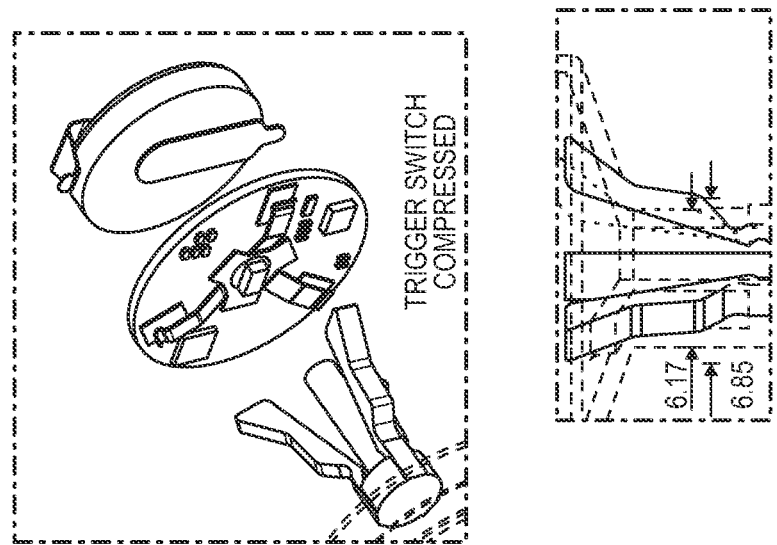
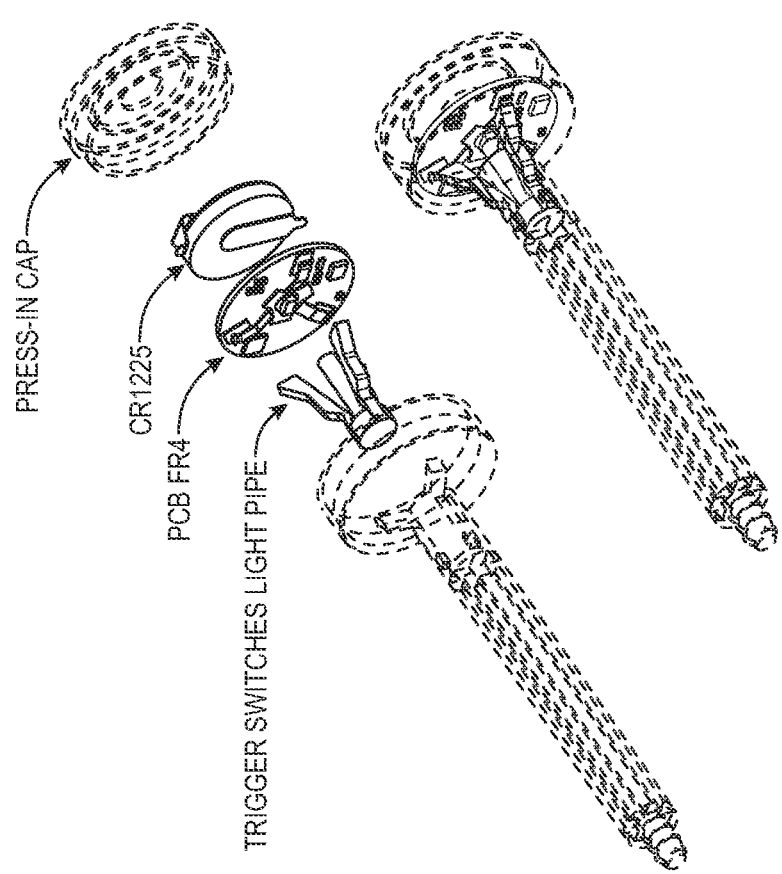
FIG. 7

COIL ARRANGEMENT DASHED LINES INDICATE THE INSTANTANEOUS DIRECTION OF INDUCED CURRENT WHEN THE ROTOR IS SPINNING

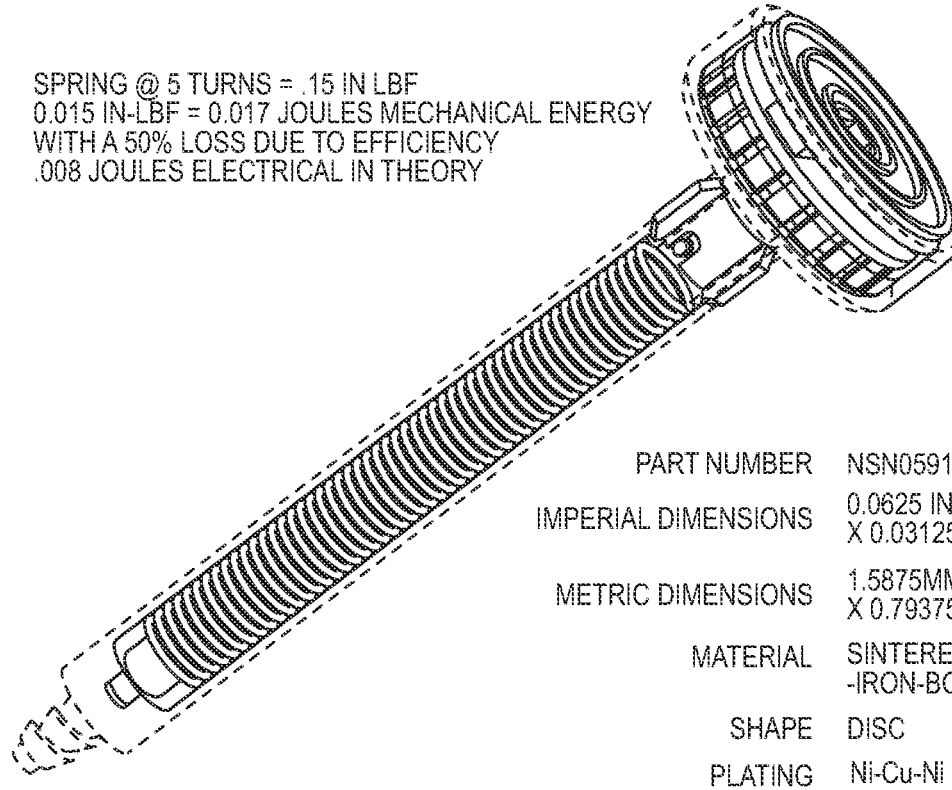

SPRING @ 5 TURNS = .15 IN LBF
0.015 IN-LBF = 0.017 JOULES MECHANICAL ENERGY
WITH A 50% LOSS DUE TO EFFICIENCY
.008 JOULES ELECTRICAL IN THEORY

MAGNET DATA
GAUSS FIELD: 2103

| | |
|---|---|
| PART NUMBER | NSN0591 |
| IMPERIAL DIMENSIONS | 0.0625 INCH DIAMETER X 0.03125 INCH THICK |
| METRIC DIMENSIONS | 1.5875MM DIAMETER X 0.79375MM THICK |
| MATERIAL | SINTERED NEODYMIUM -IRON-BORON (NDFeB) |
| SHAPE | DISC |
| PLATING | Ni-Cu-Ni (NICKEL) |
| MAGNETIZATION DIRECTION | THICKNESS |
| GRADE | N40 |
| PULL FORCE(lBS[G]) | 0.17[77] |
| SURFACE FIELD(G) | 2103 |
| OPERATING TEMPERATURE | 80 DEG C (176 DEG F) |
| DIMENSIONAL TOLERANCE | +/- 0.005" |
| MAGNET QUANTITY | 200 |
| VOLUME (CM3) | 0 |
| WEIGHT (G) | 0.01 |

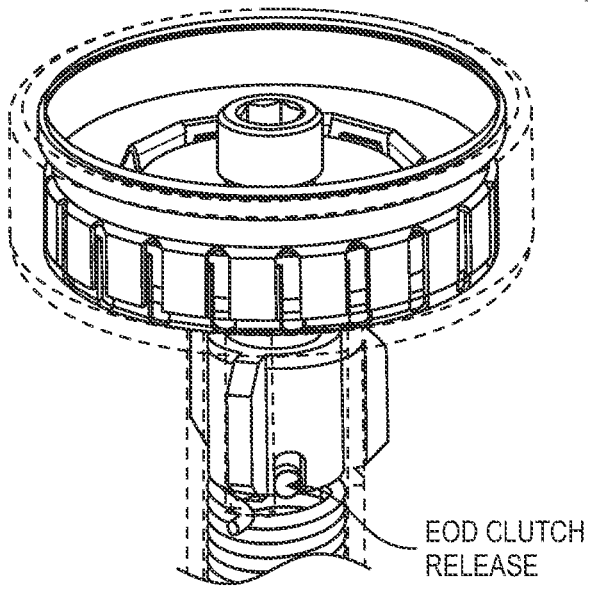

EOD CLUTCH RELEASE

FIG. 48

COIL DATA

| COIL PARAMETERS CALCULATOR | | |
|---|---|---|
| WIRE DIAMETER | .127 | (MM) (SEE GAUGE TABLE) |
| NUMBER TURNS | 200 | (TURNS) |
| BOBBIN LENGTH | 2 | (MM) |
| BOBBIN DIAMETER | 11 | (MM) |
| RATED DC CURRENT (OPTIONAL) | 1 | (A) |
| RESULTS | | |
| | COMPUTE | |
| TURNS/WINDING | 15.748 | (TURNS/WINDING) |
| NUMBER OF WINDINGS | 12.700 | (WINDINGS) |
| COIL DIAMETER | 14.226 (MM) | 0.560 (IN) |
| CROSS SECTIONAL AREA | 124.945 (MM²) | 0.194 (IN²) |
| TOTAL LENGTH OF WIRE IN COIL | 7.925 | (M) |
| RESISTANCE/METER | 1.361 | (OHMS/M) |
| RESISTANCE | 10.788 | (OHMS) |
| VOLTAGE AT RATED CURRENT | 10.788 | (V) |
| POWER AT RATED CURRENT | 10.788 | (W) |

TORSION SPRING TO-1114
PART CHARACTERISTICS

| CSC STOCK# | TO-1114 |
|---|---|
| OD (IN) | 0.185 |
| ID (IN) | 0.147 |
| LEG LENGTH (IN) | 1.400 |
| BODY LENGTH (IN) | 1.590 |
| RATE (IN-lbs / DEG) | 0.000 |
| SUGG. MAX. DEFL. DEG. | 1,891.000 |
| SUGG. MAX. TORQUE, (IN-LBS) | 0.150 |
| TOTAL COILS | 75.000 |
| WIRE DIA. (IN) | 0.019 |
| WIND DIR | RIGHT |
| SUGG. MANDREL DIA. (IN) | 0.120 |
| MATERIAL | MUSIC WIRE |

**FIG. 48
(Continued)**

INJECTION MONITORING DEVICE WITH DELIVERY SIGNATURE

CROSS REFERENCE TO RELATED APPLICATIONS

This application is a continuation of U.S. application Ser. No. 16/912,560, filed Jun. 25, 2020, now U.S. Pat. No. 11,565,054, which is a continuation of International Application No. PCT/US2018/067580, filed Dec. 27, 2018, which claims the benefit of priority to U.S. Provisional Patent Application No. 62/612,147, filed on Dec. 29, 2017, each of which are herein incorporated by reference in its entirety.

This application is related to International Patent Application Serial No. PCT/US2017/068477, filed on Dec. 27, 2017, which claims the benefit of priority to U.S. Provisional Patent Application Ser. No. 62/439,838, filed on Dec. 28, 2016.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates to drug delivery systems and methods of use thereof for recording administration of a drug dose to a subject. Aspects of the disclosure include a syringe stopper rod comprising a sensor that is configured to detect a delivery signature generated by a deflection component or other component, and to transmit a report comprising a drug dose completion signal to a data management component, e.g., a mobile computing device, when the delivery signature is detected.

BACKGROUND

The effectiveness of a medication for the treatment of a given disease or disorder is highly dependent on patient adherence to a defined dosage regimen. A typical dosage regimen may require a patient to receive a medication according to a specific schedule, e.g., two doses per day for a period of several days, weeks or months. The ability of a patient to successfully follow a specified dosage regimen is therefore of paramount importance to the ultimate efficacy of the medication in treating the disease or disorder.

In spite of its importance, patient compliance with a dosage regimen remains a challenge, especially for medications that are self-administered. A patient's non-compliance with a dosage regimen can stem from any number of factors, including, for example, failing to correctly administer the proper dose of the medication, forgetting to administer the medication at a designated time, or failing to record and/or remember the time and date of a previous administration, and therefore failing to correctly determine the time and date at which a subsequent administration should take place. Additionally, a patient may be uncertain as to whether a given lot of a medication has expired, whether the medication has reached a proper temperature for administration following its removal from cold storage, or how much of the medication to administer at a designated time. Furthermore, proper recordation of each medication dose delivered to the patient, as well as additional information relating to the medication itself (e.g., the temperature of the drug at the time of administration) is important to various other parties, including, e.g., health care providers, pharmacies, and drug manufacturers.

As provided herein, aspects of the present disclosure provide drug delivery systems and methods of use that embody certain advantageous alternatives to existing drug delivery devices and methods, and which address one or more of the needs described above.

SUMMARY OF THE DISCLOSURE

Drug delivery systems and methods of use for recording a drug dose completion signal in a data management system are provided. Aspects of the disclosure include drug delivery systems comprising a syringe stopper rod that comprises a sensor component comprising a wireless transmitter module and a deflection component configured to generate a delivery signature in response to a delivery stroke of the syringe stopper rod, wherein the wireless transmitter module is configured to transmit a report comprising a drug dose completion signal when the sensor detects the delivery signature. In some embodiments, a subject drug delivery system comprises a housing, a drug reservoir, a drug delivery cannula, an actuation component, and a data management component that is configured to receive and record a report that is transmitted from the sensor component. Aspects of the disclosure further include methods of using the subject drug delivery systems and devices to record administration of a drug dose to a patient.

In some embodiments, a syringe stopper rod comprises a sensor comprising a wireless transmitter module, and a deflection component configured to generate a delivery signature in response to a delivery stroke of the syringe stopper rod, wherein the wireless transmitter module is configured to transmit a report comprising a drug dose completion signal when the sensor detects the delivery signature. In some embodiments, the deflection component comprises a plurality of trigger switches that are configured to deflect in an inward direction when compressed by a syringe barrel, and a circuit board component disposed within the stopper rod and configured to separately detect an inward deflection of each trigger switch. In some embodiments, a syringe stopper rod comprises at least one internal trigger switch contact assembly. In some embodiments, the internal trigger switch contact assembly is disposed between a trigger switch and an internal circuit board component. In some embodiments, the circuit board component comprises a conductive rubber switch pad. In some embodiments, at least two trigger switches that are disposed on a first side of the stopper rod. In some embodiments, one or more centering components are disposed on a second side of the stopper rod, opposite the at least two trigger switches. In some embodiments, a syringe stopper rod comprises at least two trigger switches, wherein one trigger switch is disposed on a first side of the stopper rod, and one trigger switch is disposed on a second, opposite side of the stopper rod. In some embodiments, each of the at least two trigger switches is disposed at the same longitudinal position along the syringe stopper rod. In some embodiments, each of the at least two trigger switches is disposed at a different longitudinal position along the syringe stopper rod.

In some embodiments, the syringe stopper rod comprises at least four trigger switches, wherein at least two trigger switches are disposed on a first side of the syringe stopper rod, and at least two trigger switches are disposed on a second, opposite side of the syringe stopper rod. In some embodiments, each of the at least two trigger switches on the first side of the syringe stopper rod is disposed at the same longitudinal position along the syringe stopper rod as each of the at least two trigger switches on the second, opposite side of the syringe stopper rod. In some embodiments, each of the at least two trigger switches on the first side of the syringe stopper rod is disposed at a different longitudinal position along the syringe stopper rod than each of the at least two trigger switches on the second, opposite side of the syringe stopper rod.

In some embodiments, the syringe stopper rod comprises a first material, and the trigger switches are integrated into the syringe stopper rod and comprise the first material. In some embodiments, one or more trigger switches comprise a second material that is different from the first material. In some embodiments, at least one trigger switch comprises an alignment component. In some embodiments, the alignment component comprises a semi-circular tab. In some embodiments, the trigger switches are integrated into an external trigger switch assembly that is separable from the syringe stopper rod. In some embodiments, the syringe stopper rod comprises a first material, and the external trigger switch assembly comprises a second material that is different from the first material.

In some embodiments, a syringe stopper rod further comprises one or more deflection limiting components configured to limit a deflection range of one or more trigger switches. In some embodiments, at least one deflection limiting component is disposed on the syringe stopper rod adjacent to each trigger switch. In some embodiments, the deflection limiting component comprises a semi-circular tab.

In some embodiments, the delivery signature comprises a deflection order of the trigger switches, a deflection duration of each trigger switch, one or more time intervals corresponding to a time between a deflection of a first trigger switch and a deflection of a second trigger switch, or any combination thereof. In some embodiments, the deflection component comprises a force sensor. In some embodiments, the force sensor is an absolute or a relative force sensor.

In some embodiments, the deflection component comprises a circuit board sensor component comprising a first inductive sensor coil configured to move toward a first detection target in response to a force applied to the syringe stopper rod by a user. In some embodiments, the first detection target is disposed on an internal surface of the syringe stopper rod. In some embodiments, the first detection target is disposed on an external surface of the syringe stopper rod. In some embodiments, the first detection target is disposed on a thumb pad. In some embodiments, the first detection target comprises a conductive material. In some embodiments, the delivery signature comprises an injection force profile applied to the syringe stopper rod by a user. In some embodiments, the injection force profile comprises a break loose force, a glide force, an end of dose force, or any combination thereof. In some embodiments, the injection force profile further comprises a first time interval and/or force magnitude associated with the break loose force, a second time interval and/or force magnitude associated with the glide force, and a third time interval and/or force magnitude associate the end of dose force. In some embodiments, the injection force profile comprises a characteristic shape that is indicative of the delivery stroke.

In some embodiments, a syringe stopper rod comprises a sensor comprising a wireless transmitter module, and an extension component configured to generate a delivery signature in response to a delivery stroke of the syringe stopper rod, wherein the extension component extends within a central cavity of the syringe stopper rod and comprises: (i) a first inductive sensor coil configured to move toward a first detection target in response to a force applied to the syringe stopper rod by a user, and (ii) a second inductive sensor coil configured to detect a second detection target disposed on a syringe barrel, and wherein the wireless transmitter module is configured to transmit a report comprising a drug dose completion signal when the sensor detects the delivery signature. In some embodiments, the delivery signature comprises detection of the first and second detection targets by the first and second inductive sensor coils. In some embodiments, the second detection target comprises a uniform geometry, and wherein the delivery signature comprises detection of one or more aspects of the uniform geometry by the second inductive sensor coil to measure a progression or a completion of the delivery stroke. In some embodiments, the second detection target comprises a repeating geometry, and wherein the delivery signature comprises detection of one or more aspects of the repeating geometry by the second inductive sensor coil to measure a progression or a completion of the delivery stroke. In some embodiments, the first and second detection targets comprise a conductive material. In some embodiments, the delivery signature comprises a characteristic shape that is indicative of the delivery stroke.

In some embodiments, a syringe stopper rod comprises a sensor comprising a wireless transmitter module, and an extension component configured to generate a delivery signature in response to a delivery stroke of the syringe stopper rod, wherein the extension component extends within a central cavity of the syringe stopper rod and comprises a first inductive sensor coil that is configured to detect a first detection target comprising a variable geometry and disposed on a syringe barrel, and wherein the wireless transmitter module is configured to transmit a report comprising a drug dose completion signal when the sensor detects the delivery signature. In some embodiments, the delivery signature comprises detection of one or more aspects of the variable geometry of the first detection target by the first inductive sensor coil to measure a progression or a completion of the delivery stroke. In some embodiments, a syringe stopper rod further comprises a second inductive sensor coil configured to move toward a second detection target in response to a force applied to the syringe stopper rod by a user. In some embodiments, the delivery signature comprises detection of the first and second detection targets by the first and second inductive sensor coils. In some embodiments, the delivery signature comprises a characteristic shape that is indicative of the delivery stroke. In some embodiments, the first and second detection targets comprise a conductive material.

In some embodiments, a syringe stopper rod further comprises an indicator component. In some embodiments, the indicator component is configured to indicate a ready state to a user. In some embodiments, the indicator component is configured to indicate an unready state to a user. In some embodiments, the indicator component is configured to indicate a dose-in-progress state to a user. In some embodiments, the indicator component is configured to indicate a dose completed state to a user. In some embodiments, the indicator component is configured to indicate a sleep mode to a user. In some embodiments, the indicator component is configured to indicate a low battery state to a user.

In some embodiments, the indicator component is a visual indicator component. In some embodiments, the visual indicator component comprises a light-emitting component.

In some embodiments, the light-emitting component comprises a light-emitting diode (LED). In some embodiments, the light-emitting component comprises an organic light-emitting diode (OLED). In some embodiments, a syringe stopper rod further comprises a light pipe.

In some embodiments, the indicator component is a haptic indicator component. In some embodiments, the haptic indicator component comprises a vibration component. In some embodiments, the indicator component is an auditory indicator component. In some embodiments, the auditory indicator component is configured to produce a plurality of unique sounds.

In some embodiments, the sensor component further comprises a light sensor. In some embodiments, a syringe stopper rod further comprises a sensor housing configured to house the sensor component, wherein the sensor housing comprises a window that is configured to allow ambient light to contact the light sensor. In some embodiments, the sensor component further comprises a motion sensor. In some embodiments, the sensor component further comprises a touch sensor. In some embodiments, the sensor component further comprises a capacitance sensor component that is configured to detect a skin contact from a user. In some embodiments, the capacitance sensor component is located on an outer surface of the syringe stopper rod. In some embodiments, the syringe stopper rod comprises a thumb pad, and the capacitance sensor component is located on an interior surface of the thumb pad. In some embodiments, the sensor component further comprises a temperature sensor. In some embodiments, the sensor component comprises a non-volatile memory component. In some embodiments, the non-volatile memory component comprises at least one drug identification characteristic. In some embodiments, the at least one drug identification characteristic is encoded into the non-volatile memory component of the sensor. In some embodiments, the non-volatile memory component is configured to be programmed using over-the-air transmission with a universal unique identifier (UUID). In some embodiments, the at least one drug identification characteristic is encoded into a non-volatile memory component on a drug reservoir, and wherein the sensor component is configured to transfer the at least one drug identification characteristic from the non-volatile memory component on the drug reservoir to the non-volatile memory component on the sensor. In some embodiments, the sensor component is configured to wirelessly transfer the at least one drug identification characteristic from the non-volatile memory component on the drug reservoir to the non-volatile memory component on the sensor.

In some embodiments, the at least one drug identification characteristic is selected from the group consisting of: a drug name, a drug concentration, a drug dose, a drug dosage, a serial number, a lot number, an expiration date, a manufacturing site, or any combination thereof. In some embodiments, a syringe stopper rod further comprises one or more device identification characteristics selected from: a device name, type, model number, serial number, lot number, date of manufacture, place of manufacture, universal unique identifier (UUID), or any combination thereof.

In some embodiments, a distal end of the syringe stopper rod comprises a coupler component that is configured to mechanically couple the syringe stopper rod to a syringe stopper. In some embodiments, the coupler component comprises a threaded coupler component, an adhesive couple component, a snap fit coupler component, a magnetic coupler, or any combination thereof.

In some embodiments, a drug delivery system comprises a housing, a drug reservoir, a drug delivery cannula, an actuation component comprising a deflection or extension component configured to generate a delivery signature in response to a delivery stroke of the actuation component, wherein the wireless transmitter module is configured to transmit a report comprising a drug dose completion signal when the sensor detects the delivery signature, and a data management component configured to receive and record the report from the sensor component. In some embodiments, the sensor comprises a non-volatile memory component that is encoded with at least one unique drug identification characteristic. In some embodiments, the drug reservoir comprises a non-volatile memory component that is encoded with at least one drug identification characteristic. In some embodiments, the sensor is configured to acquire the at least one drug identification characteristic from the non-volatile memory component on the drug reservoir. In some embodiments, the at least one drug identification characteristic is selected from the group consisting of: a drug name, a drug concentration, a drug dose, a drug dosage, a serial number, a lot number, an expiration date, a manufacturing site, or any combination thereof.

In some embodiments, the drug reservoir comprises a syringe. In some embodiments, the syringe is a pre-filled syringe. In some embodiments, the drug reservoir comprises a vial. In some embodiments, the drug reservoir comprises a cartridge. In some embodiments, the drug reservoir is removably coupled to the housing. In some embodiments, the drug delivery cannula comprises a needle. In some embodiments, the needle is removably coupled to the housing.

In some embodiments, a drug delivery system further comprises a needle shield. In some embodiments, the drug delivery cannula comprises a catheter. In some embodiments, the catheter is an implantable catheter. In some embodiments, the actuation component is removably coupled to drug reservoir. In some embodiments, the drug reservoir comprises a syringe, and the actuation component comprises a syringe stopper rod as described herein. In some embodiments, the drug delivery cannula comprises a needle, and wherein the drug delivery system further comprises a needle safety device (NSD). In some embodiments, the NSD is configured to sequester the needle upon completion of a delivery stroke by the actuation component.

In some embodiments, a drug delivery system further comprises a finger flange component. In some embodiments, the data management system comprises a mobile computing device. In some embodiments, the mobile computing device is a smart phone. In some embodiments, the smart phone comprises a computer application configured to record administration of a drug dose to a patient. In some embodiments, the report comprises a drug temperature value. In some embodiments, the report comprises a dose amount. In some embodiments, the report comprises a dose administration time stamp. In some embodiments, the report comprises a geographical location. In some embodiments, the report comprises an anatomical location. In some embodiments, the report comprises a drug authentication signal. In some embodiments, the drug authentication signal comprises at least one unique drug identification characteristic. In some embodiments, the at least one unique drug identification characteristic is selected from the group consisting of: a drug name, a drug concentration, a drug dose, a drug dosage, a serial number, a lot number, an expiration date, a manufacturing site, or any combination thereof. In some embodiments, the data management component is configured to validate the drug authentication signal.

In some embodiments, the data management component is configured to utilize the drug authentication signal to obtain one or more additional unique drug identification characteristics. In some embodiments, the one or more additional unique drug identification characteristics are selected from the group consisting of: a drug name, a drug concentration, a drug dose, a drug dosage, a serial number, a lot number, an expiration date, a manufacturing site, or any combination thereof. In some embodiments, the data management component is configured to transmit the drug authentication signal to a remote database and receive the one or more additional unique drug identification characteristics in response. In some embodiments, the data management component is an Internet-enabled data management component, and is configured to wirelessly transmit the drug authentication signal over the Internet to a remote database, and to wirelessly receive the one or more additional unique drug identification characteristics over the Internet in response.

Aspects of the disclosure include methods for recording administration of a drug dose to a patient, the methods comprising inserting the drug delivery cannula of a drug delivery system described herein into the patient, completing a delivery stroke of the actuation component, thereby causing the deflection or extension component to generate a delivery signature that is detected by the sensor, and causing the wireless transmitter module to transmit a report comprising a drug dose completion signal to the data management component, and receiving and recording the report in the data management component, thereby recording administration of the drug dose to the patient. In some embodiments, the data management system comprises a mobile computing device. In some embodiments, the mobile computing device is a smart phone. In some embodiments, the smart phone comprises a computer application configured to record administration of a drug dose to the patient. In some embodiments, the report comprises a drug temperature value. In some embodiments, the report comprises a dose amount. In some embodiments, the report comprises a dose administration time stamp. In some embodiments, the report comprises a geographical location. In some embodiments, the report comprises an anatomical location. In some embodiments, the report comprises a drug authentication signal. In some embodiments, the drug authentication signal comprises at least one drug identification characteristic. In some embodiments, the at least one drug identification characteristic is selected from the group consisting of: a drug name, a drug concentration, a drug dose, a drug dosage, a serial number, a lot number, an expiration date, a manufacturing site, or any combination thereof.

In some embodiments, a method further comprises validating the drug authentication signal. In some embodiments, a method further comprises utilizing the unique drug authentication signal to obtain one or more additional drug identification characteristics. In some embodiments, the one or more additional drug identification characteristics are selected from the group consisting of: a drug name, a drug concentration, a drug dose, a drug dosage, a serial number, a lot number, an expiration date, a manufacturing site, or any combination thereof. In some embodiments, a method further comprises transmitting the drug authentication signal to a remote database and receiving the one or more additional drug identification characteristics in response. In some embodiments, the data management component is an Internet-enabled data management component, and wherein the method comprises wirelessly transmitting the drug authentication signal over the Internet to a remote database, and wirelessly receiving the one or more additional drug authentication characteristics over the Internet in response.

Aspects of the disclosure include drug delivery systems comprising a housing, a drug reservoir in the housing, a drug deliver cannula, an actuation component, a transmitter module and an energy harvesting system. In some embodiments, the drug delivery cannula is in fluid communication with the drug reservoir. In these embodiments, the actuation component is configured to generate a delivery signature in response to a delivery stroke of the actuation component. The transmitter module is configured to transmit a report comprising a drug dose completion signal when a sensor detects the delivery signature. The energy harvesting system is configured to supply electrical energy to the actuation component, the sensor and the transmitter module.

In some embodiments, the drug delivery system does not include any battery. The energy harvesting system may harvest energy from ambient radiation, a fluid flow, a photovoltaic source, a piezoelectric source, a pyroelectric source, a thermoelectric source, an electrostatic source, a chemical source, using magnetic induction, or a combination thereof.

In some embodiments, the use of magnetic induction is in an impulse energy harvester configuration, a levitating magnetic harvester configuration, a cantilevered beam harvester configuration, an axial flux generator configuration, a clawpole microgenerator configuration, or a combination thereof.

In some embodiments, the energy harvesting system may include a leaf spring, a torsion spring and/or a clock spring. In some embodiments, a spring may be located in a proximal head portion of the actuation component. A torsion spring may be located in a distal rod portion of the actuation component. In some embodiments, a torsion spring is rotationally coupled to a rotor of a generator in a fixed fashion that permits the rotor and spring to oscillate after energy has been imparted from the spring to the rotor. In some embodiments, a torsion spring is rotationally coupled to a rotor of a generator in a releasable fashion that permits the rotor to freewheel after energy has been imparted from the spring to the rotor.

In some embodiments, the drug delivery system may include a plurality of coils formed on at least one printed circuit board. The at least one printed circuit board may include more than two conductive layers. In some embodiments, the drug delivery system includes a generator having a rotor located within a stator. In some embodiments, the drug delivery system includes a generator having a stator located within a rotor.

Aspects of the disclosure include drug delivery systems comprising a housing, a drug reservoir in the housing, a drug deliver cannula, an actuation component, a transmitter module and a battery. In some embodiments, the drug delivery cannula is in fluid communication with the drug reservoir. In these embodiments, the actuation component is configured to generate a delivery signature in response to a delivery stroke of the actuation component. The transmitter module is configured to transmit a report comprising a drug dose completion signal when a sensor detects the delivery signature. The battery is configured to supply electrical energy to the actuation component, the sensor and the transmitter module. The battery is also removably located in a proximal head portion of the actuation component.

In some embodiments, the head portion includes a slide top configuration in which a top slides open to expose the battery and permit its removal. In some embodiments, the head portion includes a flip top configuration in which a top rotates open to expose the battery and permit its removal. In some embodiments, the head portion includes a pop top configuration in which sides of the head portion are squeezed together in order to release a top portion. In some embodiments, the head portion includes a side flip-out eject configuration in which a user's fingertip is used to flip an ejection lever to eject the battery.

BRIEF DESCRIPTION OF THE DRAWINGS

FIG. 7 is a three dimensional rendering showing a syringe stopper rod, a trigger switch assembly comprising three trigger switches, and a battery assembly according to one embodiment of the disclosure.

FIG. 48 is a three dimensional rendering of a claw-pole microgenerator deployed in a syringe plunger rod according to one embodiment of the disclosure. The left side shows a perspective view of the plunger rod and the right side shows an enlarged view of the proximal head portion of the plunger rod.

DEFINITIONS

Figure 1:
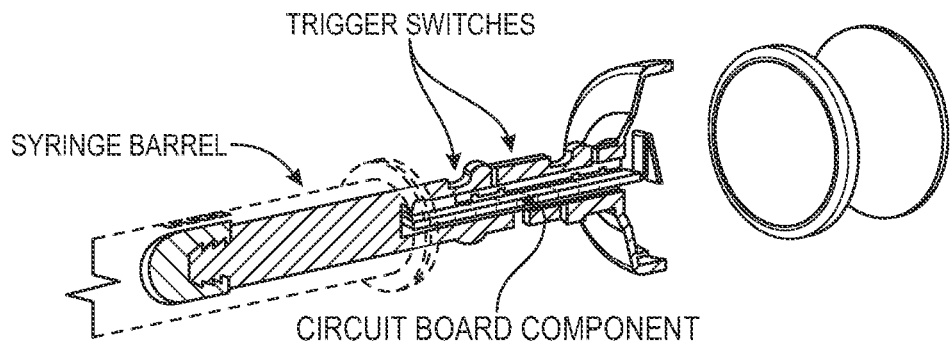
FIG. 1 is a three dimensional exploded view of a syringe stopper rod according to one embodiment of the disclosure.

For purposes of interpreting this specification, the following definitions will apply, and whenever appropriate, terms used in the singular will also include the plural and vice versa.

The terms "drug", "medicine" and "medication" as used interchangeably herein refer to a substance that has a physiological effect when introduced into the body of a patient.

The term "patient" as used herein refers to a human or a non-human animal who is being treated and/or monitored for a medical condition or disorder.

The term "delivery stroke" as used herein refers to a physical motion of an actuation component of a subject drug delivery system or device that results in the dispensation of a specified dose of a drug.

The term "delivery signature" as used herein refers to any combination of data inputs that are representative of a successful delivery stroke.

The terms "dose" and "drug dose" as used interchangeably herein refer to an amount of a drug to be administered to a patient at any one time. A "dose" can be a volume-based dose (e.g., a specific volume of a drug to be administered at one time) or a weight-based dose (e.g., a specific weight of a drug to be administered at one time).

The terms "dosage" and "drug dosage" as used interchangeably herein refer to the frequency at which a drug dose is to be administered to a patient.

The term "haptic indicator" as used herein refers to a component that creates a signal that is detectable via a patient's or a user's sense of touch.

The term "drug identification characteristic" as used herein refers to any information relating to a drug's identity and/or its biochemical characteristics (including, but not limited to, a drug's name, concentration, dose, dosage, serial number, lot number, expiration date, manufacturing date, site of manufacture, or any combination thereof).

The term "cannula" as used herein refers to a thin, tube-like element that is configured to be inserted into the body of a patient (e.g., inserted into an artery or a vein, or inserted subcutaneously). As used herein, a "cannula" can be rigid, semi-rigid, or flexible.

The term "catheter" as used herein refers to a thin, flexible tube-like element that is configured to be inserted into the body of a patient (e.g., inserted into an artery or a vein, or inserted subcutaneously).

The terms "smart phone" and "smartphone" as used interchangeably herein refer to a mobile phone with an operating system that comprises features of a personal computer operating system (e.g., the ability to install and run application programs, the ability to send and receive data).

The terms "graphical user interface" or "GUI" as used interchangeably herein refer to a user interface that is configured to allow a user to interact with an electronic device (e.g., a data management component) through one or more graphical icons and/or text-based commands.

The term "time stamp" as used herein refers to a specific date and time that are associated with an event, indicating the specific date and time when the event took place.

The term "Internet-enabled" as used herein refers to the ability of the referenced device or system to send and/or receive information over the Internet.

DETAILED DESCRIPTION

Drug delivery systems and methods of use for recording a drug dose completion signal in a data management system are provided. Aspects of the disclosure include drug delivery systems comprising a syringe stopper rod that comprises a sensor component comprising a wireless transmitter module and an a deflection component configured to generate a delivery signature in response to a delivery stroke of the syringe stopper rod, wherein the wireless transmitter module is configured to transmit a report comprising a drug dose completion signal when the sensor detects the delivery signature. In some embodiments, a subject drug delivery system comprises a housing, a drug reservoir, a drug delivery cannula, an actuation component, and a data management component that is configured to receive and record a report that is transmitted from the sensor component. Aspects of the disclosure further include methods of using the subject drug delivery systems and devices to record administration of a drug dose to a patient.

Before the present invention is further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "the component" includes reference to one or more components, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

Systems and Devices

As reviewed above, aspects of the disclosure include drug delivery systems comprising a syringe stopper rod that comprises a sensor component comprising a wireless transmitter module and an a deflection component configured to generate a delivery signature in response to a delivery stroke of the syringe stopper rod, wherein the wireless transmitter module is configured to transmit a report comprising a drug dose completion signal when the sensor detects the delivery signature. In some embodiments, a subject system comprises a housing, a drug reservoir, a drug delivery cannula, a sensor component comprising a wireless transmitter module, and an actuation component comprising a deflection component configured to generate a delivery signature when the actuation component has completed a delivery stroke, wherein the wireless transmitter module is configured to transmit a report comprising a drug dose completion signal when the delivery signature is detected, and a data management component configured to receive and record the report from the sensor component. Each of these components is now further described in greater detail.

Sensor Component

As reviewed above, aspects of the disclosure include systems and devices that comprise a sensor component. Sensor components in accordance with embodiments of the disclosure are configured to acquire one or more data inputs from the subject systems and devices, or from the immediate vicinity of the subject systems and devices, and to transmit a report comprising a drug dose completion signal when a delivery signature is detected. In certain embodiments, the report transmitted by the sensor component includes additional information, such as, e.g., one or more drug identification characteristics (described further herein).

In some embodiments, a sensor component comprises a circuit board component that is configured or adapted to mechanically support and electrically connect one or more electronic components of a subject sensor. Circuit board components in accordance with embodiments of the disclosure can include, without limitation, printed circuit boards, etched circuit boards, flexible circuit boards, or any combination thereof. In some embodiments, a circuit board component comprises a printed circuit board (PCB).

Circuit board components in accordance with embodiments of the disclosure can comprise conductive tracks, pads, or other features that are etched from conductive sheets (e.g., copper sheets) that are attached to a non-conductive substrate. In certain embodiments, standard circuit components, such as, e.g., capacitors, resistors, memory components, and the like, are electrically connected to a circuit board component (e.g., are soldered to a PCB). Connection of one or more electronic circuit components to a PCB results in a printed circuit assembly (PCA) or a printed circuit board assembly (PCBA), which terms are used interchangeably herein.

Aspects of the disclosure include switches that are configured to establish or break an electrical contact in a subject circuit board component in response to an external stimulus (e.g., in response to an external mechanical stimulus). In some embodiments, a circuit board component comprises a momentary contact switch that is configured to establish or break an electrical contact only while the momentary contact switch is in an activated state. In some embodiments, a circuit board component comprises a non-momentary contact switch that is configured to establish or break an electrical contact until the non-momentary switch is activated again.

In some embodiments, a sensor component comprises a position sensor that is configured or adapted to permit position measurement of one or more components of the subject drug delivery systems and devices. For example, in some embodiments, a position sensor is configured to detect and/or measure a position of an actuation component and/or a deflection component. In some embodiments, a position sensor is configured to detect an orientation of one or more components of a subject device (e.g., an orientation of a drug delivery cannula). Position sensors in accordance with embodiments of the disclosure can be absolute position sensors or relative position sensors, and can be linear, angular or multi-axis position sensors. In some embodiments, a position sensor is configured to acquire a plurality of measurements over a defined time interval, or during execution of a drug delivery procedure, in order to measure a position of one more components of the subject systems or devices, either as a function of time, or as a function of progression through the drug delivery procedure.

In some embodiments, a sensor component and/or a deflection component comprises a force sensor that is configured or adapted to detect and/or measure one or more forces in one or more components of the subject drug delivery systems and devices. For example, in some embodiments, a force sensor is configured to measure the amount of force that is applied to a drug reservoir by an actuation component (e.g., the amount of force that is applied to a syringe stopper by a syringe stopper rod, or the amount of force that is applied to a thumb pad by a user). Force sensors in accordance with embodiments of the disclosure can be absolute or relative force sensors. Non-limiting examples of force sensors include electrical resistance strain gauges, elastic strain gauges, foil strain gauges, semiconductor strain gauges, thin-film strain gauges, wire strain gauges, piezoelectric force transducers, strain gauge load cells, inductive sensors and the like.

In some embodiments, a sensor component comprises a light sensor that is configured or adapted to detect and/or measure ambient light. For example, in some embodiments, a light sensor is configured to determine whether an amount of ambient light in the vicinity of a subject drug delivery system or device is above a predetermined threshold value. Light sensors in accordance with embodiments of the disclosure can be absolute or relative light sensors. In some embodiments, a light sensor is used to detect an increase in ambient light, thereby indicating that a subject device has been removed from its packaging, removed from a storage container, and/or removed from a dark location.

In some embodiments, a sensor component comprises a motion sensor that is configured or adapted to detect and/or measure motion of a subject drug delivery system or device. For example, in some embodiments, a motion sensor is configured to determine whether a device, or component thereof, moves more than a predetermined threshold value. Motion sensors in accordance with embodiments of the disclosure can be absolute or relative motion sensors. In some embodiments, a motion sensor is used to detect motion of a subject device, thereby indicating that a user has begun interacting with the device.

In some embodiments, a sensor component comprises a temperature sensor that is configured or adapted to detect and/or measure a temperature of one or more components of the subject systems or devices. For example, in some embodiments, a temperature sensor is configured to determine whether the temperature of a drug in a drug reservoir is above a predetermined threshold value, or is within a predetermined temperature range. Temperature sensors in accordance with embodiments of the disclosure can be absolute or relative temperature sensors. In some embodiments, a temperature sensor is used to detect an increase in temperature, thereby indicating that a subject device has been removed from cold storage and has reached a temperature that is suitable for administration of the drug to a patient. In some embodiments, a temperature sensor is used to determine when a cold chain is broken (i.e., when the temperature of the device or a portion thereof (e.g., the drug reservoir) rises above a predetermined threshold temperature) and to record this information. In some embodiments, a temperature sensor is used to track when the device or a portion thereof (e.g., the drug reservoir) rises above a predetermined threshold temperature, and to wake up the device when the temperature reaches the predetermined threshold temperature to record an injection procedure. Any information relating to the cold chain of the device can be recorded and used for purposes of information tracking and/or for preparing the device for use. In some embodiments, the device is configured to wake up from a deep sleep, read the temperature from the sensor and go back to sleep. This process may be performed with low power levels once per minute or other frequency to allow long term storage of the device. In some embodiments, this process may be performed for up to 5 years on a single battery, due to fast action of the microprocessor and selective power up of only circuit components needed to read a temperature.

In some embodiments, a sensor component comprises a touch sensor that is configured or adapted to detect and/or measure contact by an object that is conductive, or that has a dielectric value that is different from air. In some embodiments, a touch sensor comprises one or more detection components (e.g., capacitive sensing components) that are placed in close proximity to, or on, the inside of an external surface of a subject drug delivery system or device (e.g., on a thumb pad of a subject syringe stopper rod) and are electrically connected to the touch sensor. When a user touches a detection component, an electrical signal is sent to the touch sensor, indicating that the user has touched the device. In some embodiments, a touch sensor is used to determine that a user has made physical contact with a subject device (e.g., that a portion of a user's skin has made physical contact with a subject device), thereby indicating that the user has begun interacting with the device.

Aspects of the subject sensor components include a power component that is configured or adapted to provide electrical power to the sensor component. In some embodiments, a power component comprises a battery. In some embodiments, a power component comprises a rechargeable battery. In certain embodiments, such as, e.g., where one or more components are disposable, a power component does not include a rechargeable battery. In some embodiments, a power component comprises one or more standard electrical cords that are configured to supply electrical power to a sensor component by establishing electrical contact with an external power source (e.g., a standard electrical outlet). In some embodiments, a subject system or device comprises an on/off switch or button that can be used to turn power to the system or device on or off, as desired.

In some embodiments, a sensor component comprises a memory component that is configured or adapted to store one or more drug identification characteristics therein. Memory components in accordance with embodiments of the disclosure can be volatile or non-volatile memory components. In some embodiments, a memory component is encoded with one or more drug identification characteristics before it is connected to the sensor component (e.g., the memory component is encoded with one or more drug identification characteristics at the time the memory component is manufactured). In some embodiments, a memory component is encoded with one or more drug identification characteristics after the memory component has been connected to the sensor component. In certain embodiments, a sensor component comprises a data acquisition component that is configured to acquire the one or more drug identification characteristics that are stored in the memory component from an external source (e.g., from an external encoder, or from a memory component on a drug reservoir). In some embodiments, a memory component is configured to wirelessly receive encoded information (e.g., a data acquisition component is configured to wirelessly acquire the one or more drug identification characteristics). In some embodiments, a sensor component comprises a near-field communication (NFC) component and/or a radio frequency identification (RFID) component that are configured for data exchange.

Drug identification characteristics in accordance with embodiments of the disclosure broadly include any information relating to a drug's identity and/or its biochemical characteristics (including, but not limited to, a drug's name, concentration, dose, dosage, serial number, lot number, universal unique identifier (UUID), expiration date, manufacturing date, site of manufacture, or any combination thereof). In some embodiments, a memory component can further comprise one or more patient identification characteristics (including, but not limited to: a patient name, patient identification number, prescription number, demographic information, patient group or subgroup, or any combination thereof). In some embodiments, a memory component can further comprise one or more drug delivery device identification characteristics (including, but not limited to: a system or device name, type, model number, serial number, lot number, date of manufacture, place of manufacture, UUID, or any combination thereof). In some embodiments, a memory component is configured to be programmed (e.g., during manufacture of the device) using over-the-air transmission with a universal unique identifier (UUID).

Aspects of the subject sensor components include a wireless transmitter module that is configured to wirelessly transmit data to a networked device (e.g., a data management component). In some embodiments, a networked device is a secure networked device. In some embodiments, transmitted data can be encrypted. In some embodiments, a wireless transmitter module is configured to communicate with one or more networked devices using a wireless transmission component (e.g., a communication link that utilizes, e.g., infrared light, radio-frequency, optical or ultrasound waves, or any combination thereof). Networked devices in accordance with embodiments of the disclosure broadly include any device or component that communicates with at least one other device over a communication link. Non-limiting examples of networked devices include mobile computing devices (e.g., smart phones, laptop computers) that use, e.g., Bluetooth, Bluetooth low energy (BLE), or Wi-Fi connections. In some embodiments, a wireless transmitter module is configured to wirelessly communicate directly with a network or directly with a remote computing device (i.e., without first communicating with a mobile computing device). In certain embodiments, a wireless transmitter module comprises an antenna. Aspects of the disclosure broadly include any radio wave spectrum communication systems, including but not limited to those that can communicate to a central hub, and then into a cloud-based computing/data transmission environment.

Sensor components in accordance with embodiments of the disclosure are configured to transmit a report comprising a drug dose completion signal when the sensor component detects a delivery signature. In some embodiments, a drug dose completion signal comprises an indication that an actuation component has completed a delivery stroke. In some embodiments, a data management component is configured to determine a volume of drug that was delivered to the patient by identifying the drug delivery system or device, and determining the volume of drug that is administered in a single delivery stroke of the identified system or device. In some embodiments, a data management component is encoded with information relating to, e.g., a volume of a drug that is administered in a single delivery stroke of a specified system or device, a start of dose, dosing speed or injection rate for a specified system or device, or any combination thereof.

In some embodiments, a subject sensor component is configured or adapted to determine one or more operational states of a drug delivery system or device. For example, in some embodiments, a sensor component is configured to determine a ready state, wherein the system or device is ready to administer a drug dose to the patient. In some embodiments, a sensor component is configured to determine an unready state, wherein the system or device is not ready to administer a drug dose to the patient. In some embodiments, a sensor component is configured to determine a dose-in-progress state, wherein the system or device is actively administering a drug dose to the patient. In some embodiments, a subject system or device can be configured to administer a drug dose to a patient over a time frame that ranges from about 1 second up to about 30 minutes, such as about 5, 10, 15, 20, 25, 30, 35, 40, 45, 50, 55, or 60 seconds, or about 1, 2, 3, 4, 5, 6, 7, 8, 9 or 10 minutes or more, such as about 11, 12, 13, 14, 15, 16, 17, 18, 19, 20, 21, 22, 23, 24, 25, 26, 27, 28 or 29 minutes or more. In some embodiments, a subject system or device is configured to remain in a dose-in-progress operational state for a period of time that is equal to the time frame for administering the drug to the patient.

In some embodiments, a sensor component is configured to determine a sleep mode state (e.g., a low power state), wherein the system or device is operating in reduced power mode, and is not ready to administer a drug dose to the patient. In some embodiments, a sensor component is configured to determine a low battery state, wherein the battery charge is below a predetermined level.

Determination of any of the states described herein can be accomplished by analysis of one or more inputs from one or more of the subject sensor components. For example, in some embodiments, a ready state can be determined when a temperature value from a temperature sensor falls within a predetermined range (i.e., indicating that the drug is at a desired temperature range for administration) and a position sensor indicates that the system or device is in a desired position or orientation for administration (e.g., a position of an actuation component is determined to be correct for administration of the drug to the patient). This arrangement can also be used for training the user on correct 'injection posture' orientation. In some embodiments, this may be done in conjunction with the correct injection posture orientation being shown on the graphical user interface of the user's mobile device.

In some embodiments, a sensor component can communicate a determined operational state, as described above, to another component of the system or device (e.g., to a data management component). In certain embodiments, the data management component can then indicate the operational state to a user (e.g., on a GUI), thereby communicating the operational state to the user. In some embodiments, as described further herein, the subject systems and devices can comprise one or more indicator components that are configured to communicate an operational state of the system or device to a user (e.g., a "ready to inject" operational state).

Sensor components in accordance with embodiments of the disclosure can be mounted in any suitable location on the subject systems or devices. For example, in some embodiments, a sensor component can be mounted in a housing that is positioned anywhere on the system or device. In one embodiment, a sensor component is mounted in a thumb pad that is attached to an actuation component (e.g., a syringe stopper rod, as described further herein). In some embodiments, a sensor component is configured to be removably coupled to subject drug delivery system or device. For example, in some embodiments, a sensor component is mounted in a thumb pad, and the thumb pad is configured to be removably coupled to a proximal end of a syringe stopper rod. In some embodiments, a sensor component can be mounted in a finger flange component. In certain embodiments, a sensor component is formed into a single unit. In certain embodiments, a sensor component comprises two or more individual units (e.g., two or more different PCBAs) that are electrically connected to one another, each of which is mounted in a suitable location on a subject drug delivery system or device.

Figure 15:
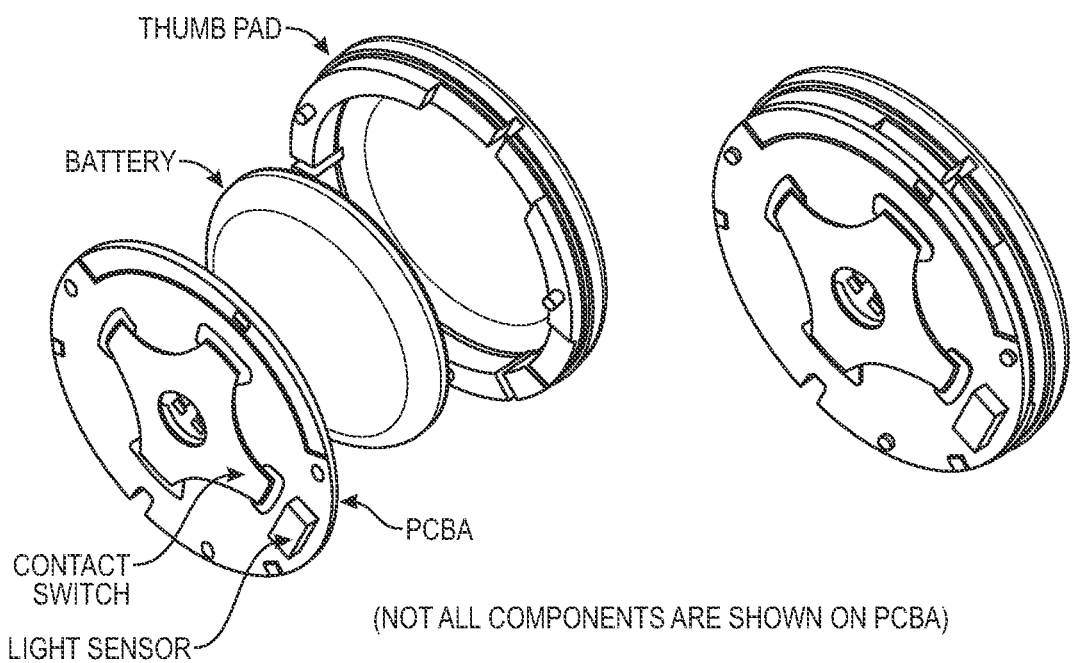
FIG. 15 is a three dimensional exploded view and a three dimension assembled view of a sensor component and battery assembly according to one embodiment of the disclosure.

Turning now to FIG. 15, a sensor component is depicted, comprising a PCBA and a battery. The depicted sensor component is configured to fit within a sensor housing that is located at a proximal end of the depicted syringe stopper rod. FIG. 1 provides another view of a sensor component that comprises a PCBA and a battery, and which is configured to fit within a sensor housing that is located at a proximal end of the depicted syringe stopper rod. FIGS. 2-13, 17 and 19 show assembled views of various embodiments of the subject devices wherein the sensor component is disposed within a sensor housing at the proximal end of the syringe stopper rod. In some embodiments, the sensor component forms a dome switch that is actuated when it engages the needle safety device (NSD), which can only occur when the stopper rod reaches the end of dose delivery position.

Deflection Components

Aspects of the disclosure include one or more deflection components that are configured to generate a delivery signature when a delivery stroke has been completed. The subject drug delivery systems and devices are configured to transmit a report comprising a drug dose completion signal only when a delivery signature has been generated and detected.

Deflection components in accordance with embodiments of the disclosure can be positioned in any suitable location on the subject systems or devices so that they can interact with one or more components of the subject systems and devices during the execution of a delivery stroke. In some embodiments, a deflection component is located along the length of an actuation component (e.g., a syringe stopper rod) and is configured to be mechanically deflected by at least a portion of the system or device (e.g., by a barrel of a syringe) during a delivery stroke. For example, in some embodiments, a deflection component comprises a plurality of trigger switches that are configured to deflect in an inward direction when compressed by a syringe barrel. In some embodiments, a deflection component comprises a force sensor that is configured to measure one or more forces applied to a portion of a subject system or device by a user (e.g., to detect a force applied to a thumb pad during a delivery stroke). In some embodiments, a deflection component comprises one or more inductive sensor coils that are configured to move toward one or more detection targets in response to a force applied to one or more components of a subject system or device.

As reviewed above, in some embodiments, a deflection component comprises a plurality of trigger switches that are configured to deflect in an inward direction when compressed by a syringe barrel. In certain embodiments, a syringe stopper rod further comprises a circuit board component disposed within the stopper rod and configured to separately detect an inward deflection of each trigger switch. In some embodiments, a syringe stopper rod comprises at least one internal trigger switch contact assembly that is disposed between a trigger switch and the internal circuit board component. In certain embodiments, an internal circuit board component can comprise a conductive rubber switch pad. In some embodiments, a syringe stopper rod comprises an internal trigger switch assembly with a plurality of laterally oriented trigger switches. In use, the laterally oriented trigger switches are deflected in an inward direction when the syringe stopper rod is inserted into a syringe barrel. In such embodiments, a circuit board component can be located in the thumb pad of the syringe stopper rod, and the internal trigger switch assembly is configured to make contact with the circuit board component when each of the trigger switches are deflected inward.

Trigger switches in accordance with embodiments of the disclosure can have any suitable dimensions to facilitate deflection. Trigger switches generally include an elongated body that is attached to a syringe stopper rod at a first end, and a head that is located at a second end of the elongated body, opposite the first end. In use, when a trigger switch enters the barrel of a syringe during a delivery stroke, the head is deflected in an inward direction, causing the elongated body to deflect in an inward direction as well. In the deflected position, the head of the trigger switch makes contact with one or more components of a contact assembly, which sends an electrical signal to the circuit board component. In certain embodiments, a trigger switch is a member of an internal trigger switch assembly and comprises two flexible members that are each connected to the internal trigger switch assembly, and which protrude from a side of the syringe stopper rod in their fully extended position, and are deflected in an inward manner when the syringe stopper rod is inserted into the syringe barrel. Deflection of the trigger switches causes a portion of the internal trigger switch assembly to make contact with a circuit board component.

In some embodiments, a plurality of trigger switches, such as 2, 3 or 4 trigger switches, are assembled in a trigger switch assembly, wherein the individual trigger switches are spaced around a central node. In some embodiments, the trigger switches are uniformly spaced around the central node, while in other embodiments, the trigger switches are spaced around the central node in a non-uniform manner. During use, the trigger switches in the assembly are deflected in accordance with a predetermined pattern to indicate successful completion of a delivery stroke. For example, in one non-limiting embodiment, a trigger switch assembly comprises three trigger switches, evenly arranged around a central node, and the assembly is disposed near a proximal end of a syringe stopper rod, just beneath the thumb pad (FIG. 7). When a delivery stroke is completed, the syringe stopper rod is fully inserted into the syringe barrel, causing each of the three trigger switches in the assembly to radially deflect in an inward direction. The deflection of the trigger switches is detected via a switch assembly located in a PCB in the thumb pad, and creates a delivery signature, or pattern, as described further herein.

In some embodiments, a trigger switch has a length that ranges from about 3 mm to about 30 mm, such as about 4, 5, 6, 7, 8, 9, 10, 11, 12, 13, 14, 15, 16, 17, 18, 19, 20, 21, 22, 23, 24, 25, 26, 27, 28 or about 29 mm. In some embodiments, a trigger switch comprises an alignment component disposed on the of the trigger switch that functions to maintain the alignment of the trigger switch as it enters the barrel of a syringe. In some embodiments, an alignment component comprises a semi-circular tab.

In some embodiments, a deflection component comprises two trigger switches that are disposed on a first side of a syringe stopper rod. In some embodiments, a deflection component comprises one or more centering components that are positioned on a side of a syringe stopper rod opposite from one or more trigger switches. The centering components function to keep the syringe stopper rod centered within the syringe barrel by provided a counteracting force to the trigger switches. Accordingly, centering components in accordance with embodiments of the disclosure have a geometry that mirrors that of the trigger switches.

In some embodiments, a deflection component comprises two trigger switches, wherein one trigger switch is disposed on a first side of the stopper rod, and another trigger switch is disposed on the opposite side of the stopper rod. In some embodiments, each of the two trigger switches is disposed at the same longitudinal position along the stopper rod, while in other embodiments, each of the two trigger switches is disposed at a different longitudinal position along the syringe stopper rod.

In some embodiments, a deflection component comprises four trigger switches, wherein two trigger switches are disposed on a first side of the stopper rod, and two trigger switches are disposed on a second, opposite side of the stopper rod. In some embodiments, each of the two trigger switches on the first side of the stopper rod is disposed at the same longitudinal position along the stopper rod as each of the two trigger switches on the second, opposite side of the syringe stopper rod. In other embodiments, each of the two trigger switches on the first side of the stopper rod is disposed at a different longitudinal position along the stopper rod than each of the two trigger switches on the second, opposite side of the syringe stopper rod.

In some embodiments, a syringe stopper rod comprises a first material, and the trigger switches are integrated into the syringe stopper rod and are made from the same material as the syringe stopper rod. In other embodiments, one or more of the trigger switches can comprise a material that is different from the material of the syringe stopper rod. In certain embodiments, one or more trigger switches are integrated into an external trigger switch assembly that is separable from the syringe stopper rod. In some embodiments, the external trigger switch assembly comprises the same material as the syringe stopper rod, while in other embodiments, the external trigger switch contact assembly comprises a material that is different from the material of the syringe stopper rod.

In some embodiments, a syringe stopper rod comprises a deflection limiting component that is configured to limit a deflection range of one or more trigger switches. Limitation of the deflection range of a trigger switch can ensure that the trigger switch does not break, and/or can facilitate establishing an electrical connection between the trigger switch and the trigger switch contact assembly in a suitable manner. In certain embodiments, a deflection limiting component is disposed on the syringe stopper rod adjacent to a trigger switch. In some embodiments, a deflection limiting component comprises a semi-circular tab.

Turning now to FIG. 1, a three dimensional exploded view of a syringe stopper rod is depicted. In the depicted embodiment, a plurality of trigger switches are disposed along the syringe stopper rod, and a circuit board component is disposed within a central cavity of the syringe stopper rod. When the syringe stopper rod is moved into the syringe barrel during a delivery stroke, the trigger switches are deflected in an inward direction and make contact with a contact assembly on the circuit board component.

Figure 2:
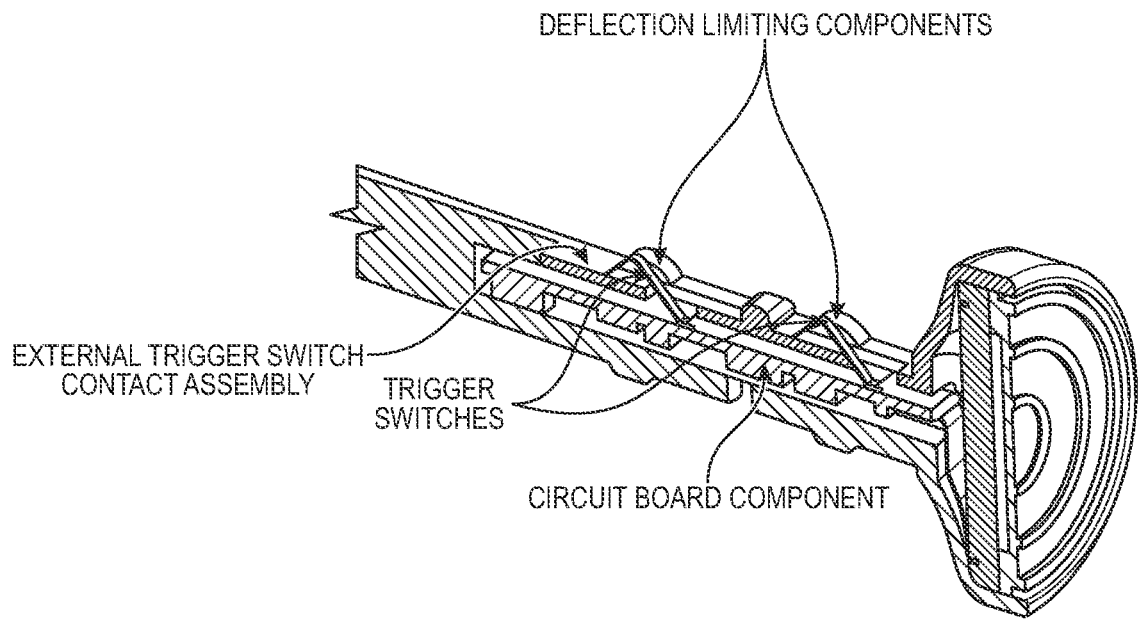
FIG. 2 is a three dimensional cross sectional rendering of a syringe stopper rod according to one embodiment of the disclosure.
Figure 3:
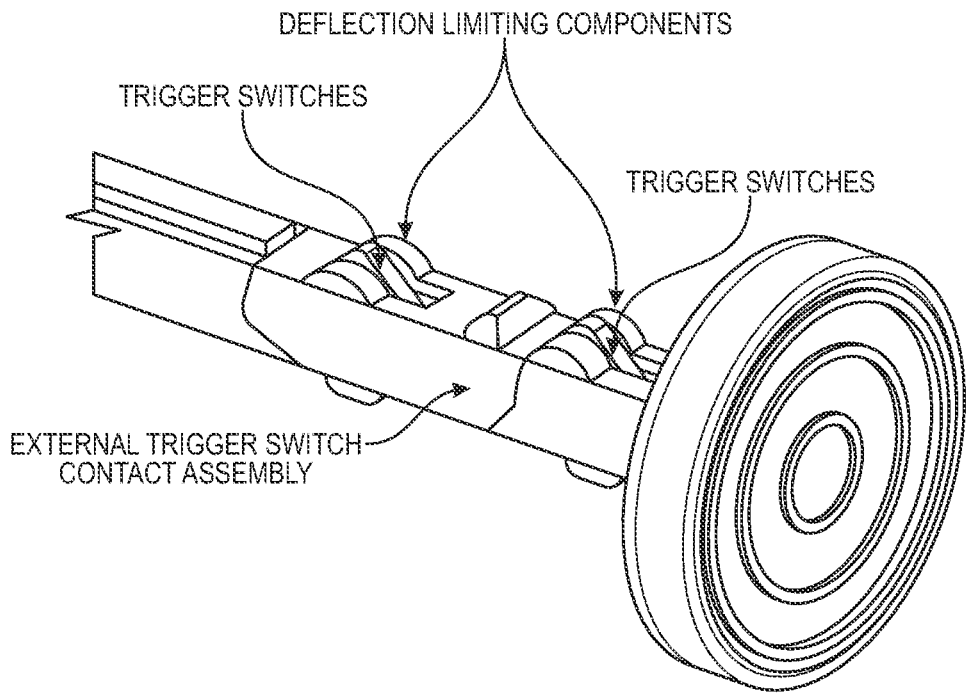
FIG. 3 is a three dimensional rendering of a syringe stopper rod according to one embodiment of the disclosure.

Turning now to FIGS. 2 and 3, a three dimensional view of a syringe stopper rod is depicted. In the depicted embodiment, a plurality of trigger switches are disposed along the syringe stopper rod, and a circuit board component is disposed within a central cavity of the syringe stopper rod. The depicted trigger switches are in the form of an external trigger switch assembly that comprises a material that is different from the material of the syringe stopper rod. Also depicted are deflection limiting components in the form of semi-circular tabs that are disposed on the syringe stopper rod. When the syringe stopper rod is moved into the syringe barrel during a delivery stroke, the trigger switches are deflected in an inward direction and make contact with a contact assembly on the circuit board component. The deflection range of the trigger switches is limited by the deflection limiting components.

Figure 4:
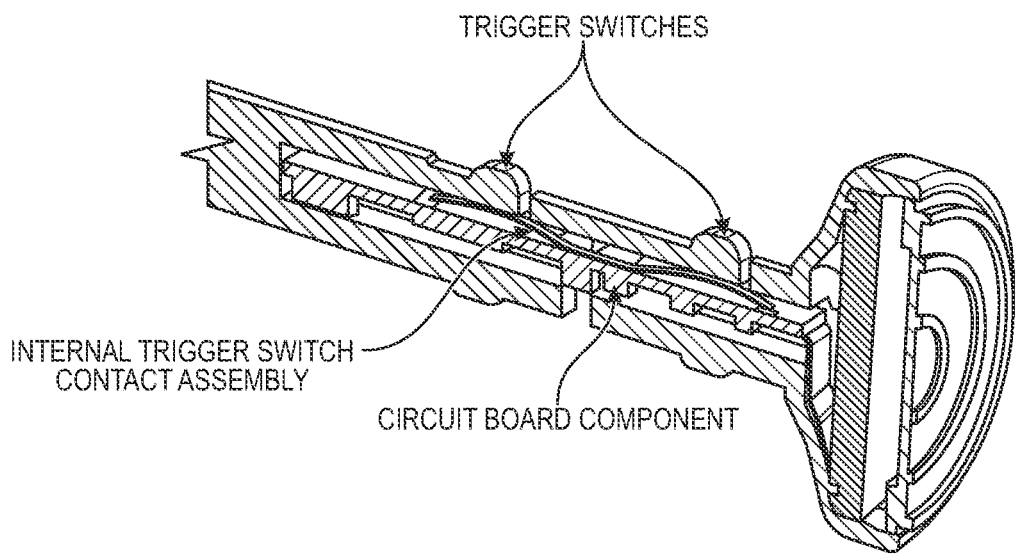
FIG. 4 is a three dimensional cross sectional rendering of a syringe stopper rod according to one embodiment of the disclosure.
Figure 6:
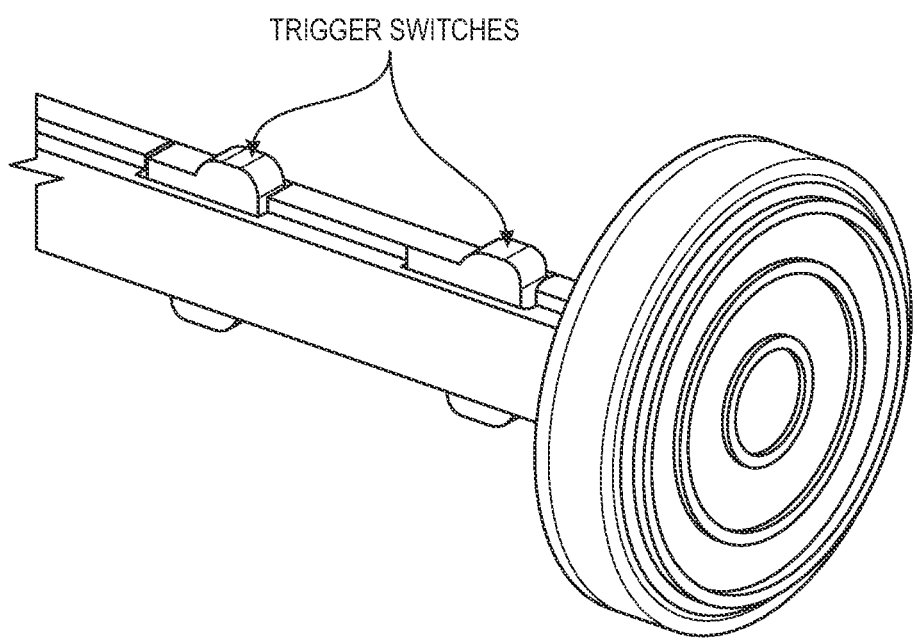
FIG. 6 is a three dimensional rendering of a syringe stopper rod according to one embodiment of the disclosure.

Turning now to FIGS. 4 and 6, a three dimensional view of a syringe stopper rod is depicted. In the depicted embodiment, a plurality of trigger switches are disposed along the syringe stopper rod, and a circuit board component is disposed within a central cavity of the syringe stopper rod. The depicted trigger switches are integrated into the syringe stopper rod and comprise the same material as the syringe stopper rod. The depicted embodiment also includes an internal trigger switch contact assembly. When the syringe stopper rod is moved into the syringe barrel during a delivery stroke, the trigger switches are deflected in an inward direction and make contact with the internal trigger switch contact assembly, which in turn makes contact with the circuit board component.

Figure 5:
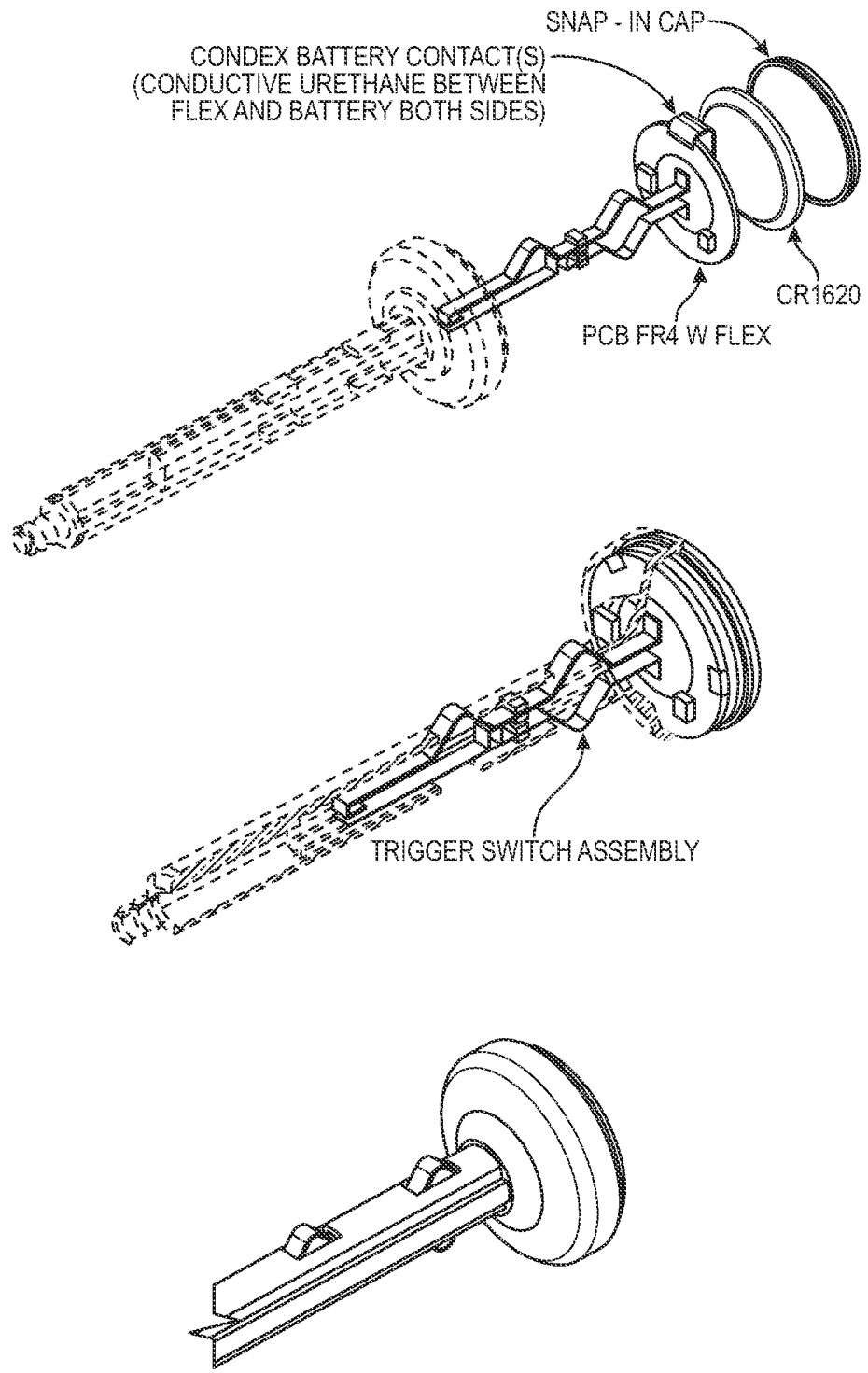
FIG. 5 is a three dimensional rendering showing a syringe stopper rod, an internal trigger switch assembly, and a battery assembly according to one embodiment of the disclosure.

Turning now to FIG. 5, a three dimensional view of a syringe stopper rod comprising an internal trigger switch assembly is depicted. The internal trigger switch assembly comprises three individual trigger switches, two of which are located on a first side of the syringe stopper rod, and one of which is located on an opposite side of the syringe stopper rod. The internal trigger switch assembly is in electrical contact with the sensor component. In use, the syringe stopper rod is inserted into a syringe barrel, and as the individual trigger switches are deflected inward, a signal from each trigger switch is detected by the sensor.

In some embodiments (not shown), the locations of components on the syringe barrel and stopper rod may be reversed or located elsewhere. For example, the trigger switch or switches may be located on the barrel along with other electrical components. In these embodiments, the switch(es) may be deflected outward by features of the stopper rod as it travels through the barrel. Alternately, the stopper rod may include one or more recesses that allow the switch(es) located on the barrel to deflect inward when they are activated. In still other embodiments, the barrel may be provided with one or more recesses that allow the switch(es) located on the stopper rod to deflect outward when they are activated. As used herein, the terminology "deflect in an inward direction" may refer to movement in a radial, axial or other direction. For example, in some embodiments a trigger switch may move proximally into the underside of the stopper rod thumb pad when signaling the end of a dose delivery.

As reviewed above, in some embodiments, a deflection component comprises a force sensor. Force sensors in accordance with embodiments of the disclosure can be absolute or relative force sensors, and details of such sensors are generally known in the art.

In certain embodiments, a deflection component comprises one or more inductive sensor coils that are configured to move toward a detection target in response to a force that is applied to a portion of the subject systems and devices during a delivery stroke. Inductive sensor coils in accordance with embodiments of the disclosure generally operate by generating an alternating electrical field that can detect a conductive material within a certain proximity of the inductive sensor coil. As such, inductive sensor coils in accordance with embodiments of the disclosure generally operate in conjunction with one or more detection targets that comprise a conductive material (e.g., a conductive metal material). The configuration of an inductive sensor coil and its detection target can take on any suitable arrangement. For example, in some embodiments, a first inductive sensor coil is disposed on a base portion of a deflection component, and the base portion is configured to deflect towards the detection target when a force is applied to the base portion by a user during a delivery stroke. In some embodiments, an inductive sensor coil is disposed on an extension component that is configured to move through a portion of a subject device during a delivery stroke, and is configured to pass one or more portions of a detection target during the delivery stroke. In certain embodiments, a detection target is disposed on an internal surface of a syringe stopper rod. In some embodiments, a detection target is disposed on an external surface of a syringe stopper rod. In some embodiments, a detection target is disposed on a thumb pad of a syringe stopper rod. In some embodiments, a detection target comprises a battery, or a portion thereof. In some embodiments, a detection target is disposed in a label that can be placed on an external surface of a syringe barrel, or an on external surface of a drug reservoir.

Detection targets in accordance with embodiments of the disclosure can have any number of different geometries. For example, in some embodiments, a detection target has a uniform geometry that does not change significantly as a function of position in a given direction. Non-limiting examples of uniform geometry detection targets include geometric shapes (e.g., rings, bands, rectangles and squares). In some embodiments, a uniform geometry detection target can be placed on an internal or an external surface of a subject device, and can be detected when an inductive sensor coil passes the detection target and/or moves towards it. In certain embodiments, a detection target with a uniform geometry is disposed over at least half of a surface of a subject system or device. For example, when a drug reservoir comprises a syringe barrel, in some embodiments, a detection target comprises a band that is disposed around at least half of the syringe barrel (i.e., covers at least 180 degrees) so as to be detectable in a manner that is independent of an orientation of a syringe stopper rod within the syringe barrel. In some embodiments, a detection target covers an angular range of about 180 to about 360 degrees, such as about 190, 200, 210, 220, 230, 240, 250, 260, 270, 280, 290, 300, 310, 320, 330, 340, or about 350 degrees.

In some embodiments, a detection target has a repeating geometry, wherein two or more uniform geometry detection targets are disposed in a repeating manner in a given direction along a surface of a subject device. For example, in some embodiments, two or more circular or square detection targets can be disposed in series along the length of a syringe barrel, or two or more circular bands that encircle the syringe barrel can be disposed in series along the length of the syringe barrel. As an inductive sensor coil passes each uniform target, the progression of the delivery stroke can be determined.

In some embodiments, a detection target has a variable geometry, wherein one or more dimensions of the detection target change as a function of position in a given direction. For example, in some embodiments, a variable detection target comprises a conductive material that starts at a minimum width at a first end of a syringe barrel, and the width gradually increases along the length of the syringe barrel to a final maximum width at the other end of the syringe barrel. Any number of variations in the variable geometry can be introduced to generate a unique reading, or signature, that is obtained as an inductive sensor coil moves past the variable geometry detection target.

Figure 8:
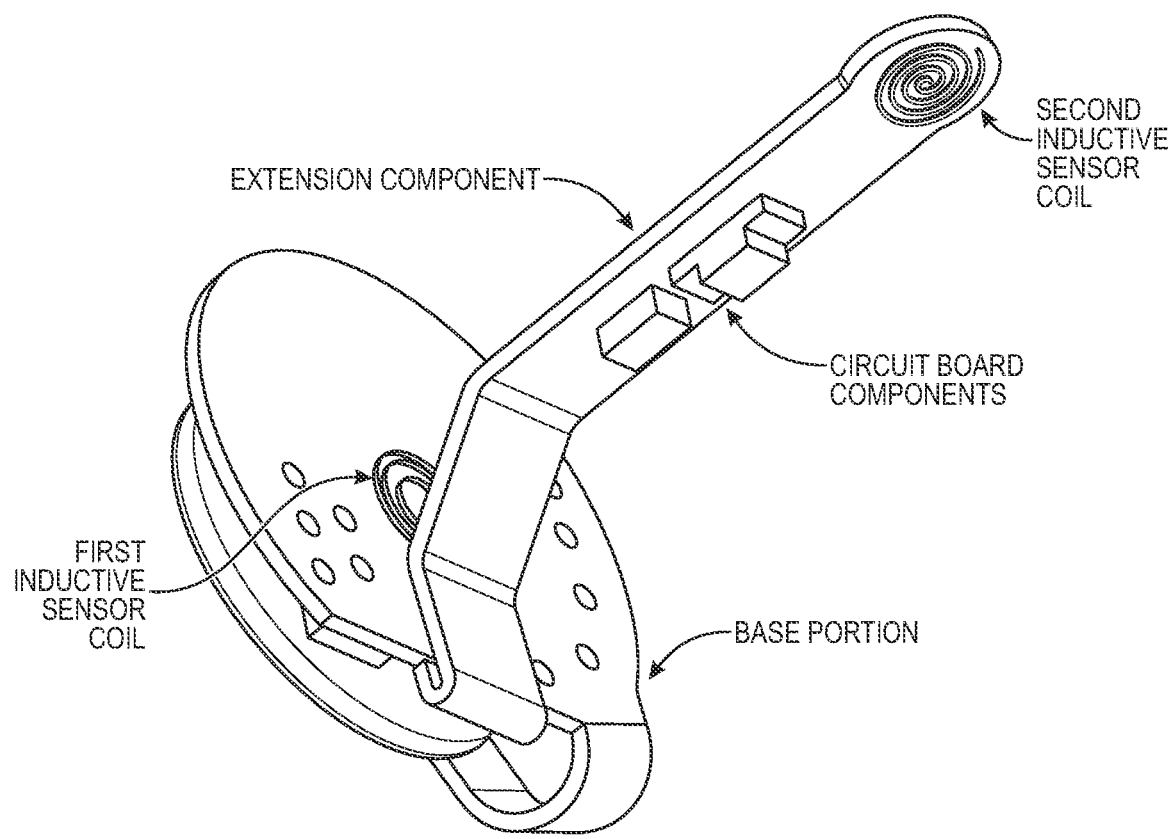
FIG. 8 is a three dimensional rendering of a deflection component according to one embodiment of the disclosure.
Figure 9:
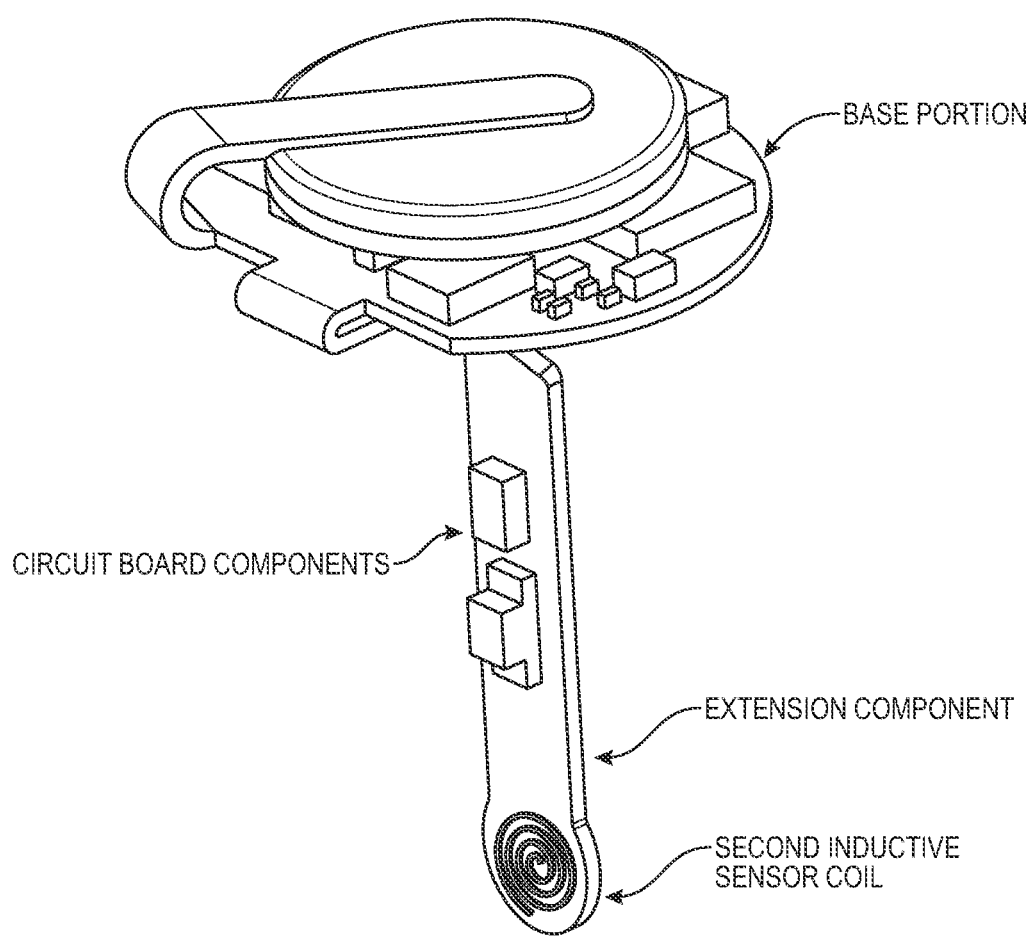
FIG. 9 is a three dimensional rendering of a deflection component according to one embodiment of the disclosure.

Turning now to FIGS. 8 and 9, a three dimensional view of a deflection component is depicted. In the depicted embodiment, a first inductive sensor coil is disposed on a base portion of the deflection component, and second inductive sensor coil is disposed on an extension component of the deflection component. Circuit board components and a battery are also depicted.

Figure 10:
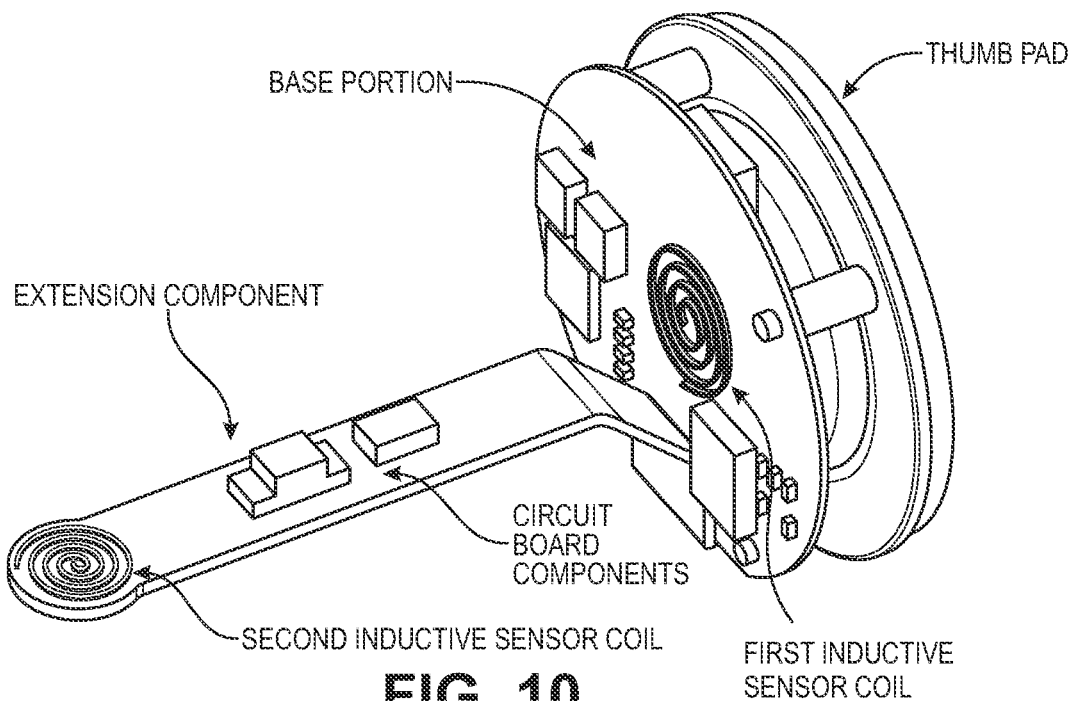
FIG. 10 is a three dimensional rendering of a deflection component according to one embodiment of the disclosure.
Figure 11:
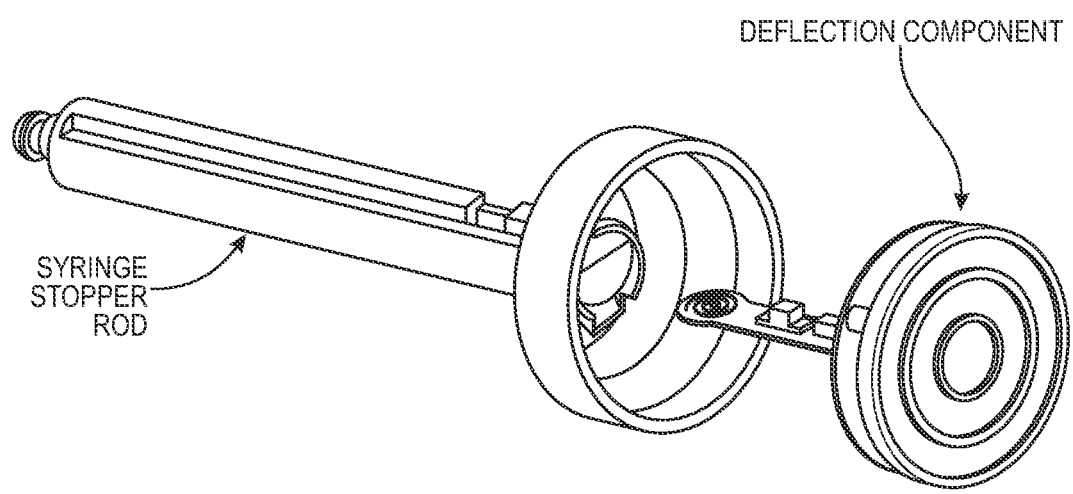
FIG. 11 is a three dimensional rendering of a syringe stopper rod and a deflection component according to one embodiment of the disclosure.

Turning now to FIG. 10, a three dimensional view of a deflection component is depicted. In the depicted embodiment, a first inductive sensor coil is disposed on a base portion of the deflection component, and second inductive sensor coil is disposed on an extension component of the deflection component. Circuit board components and a thumb pad are also depicted. When a force is applied to the thumb pad, the thumb pad deflects toward the first inductive sensor coil, and a detection target disposed on an internal surface of the thumb pad (not shown) moves toward the first inductive sensor coil. FIG. 11 depicts the deflection component described in FIG. 10 and a syringe stopper rod with a central cavity for receiving the extension component.

Figure 12:
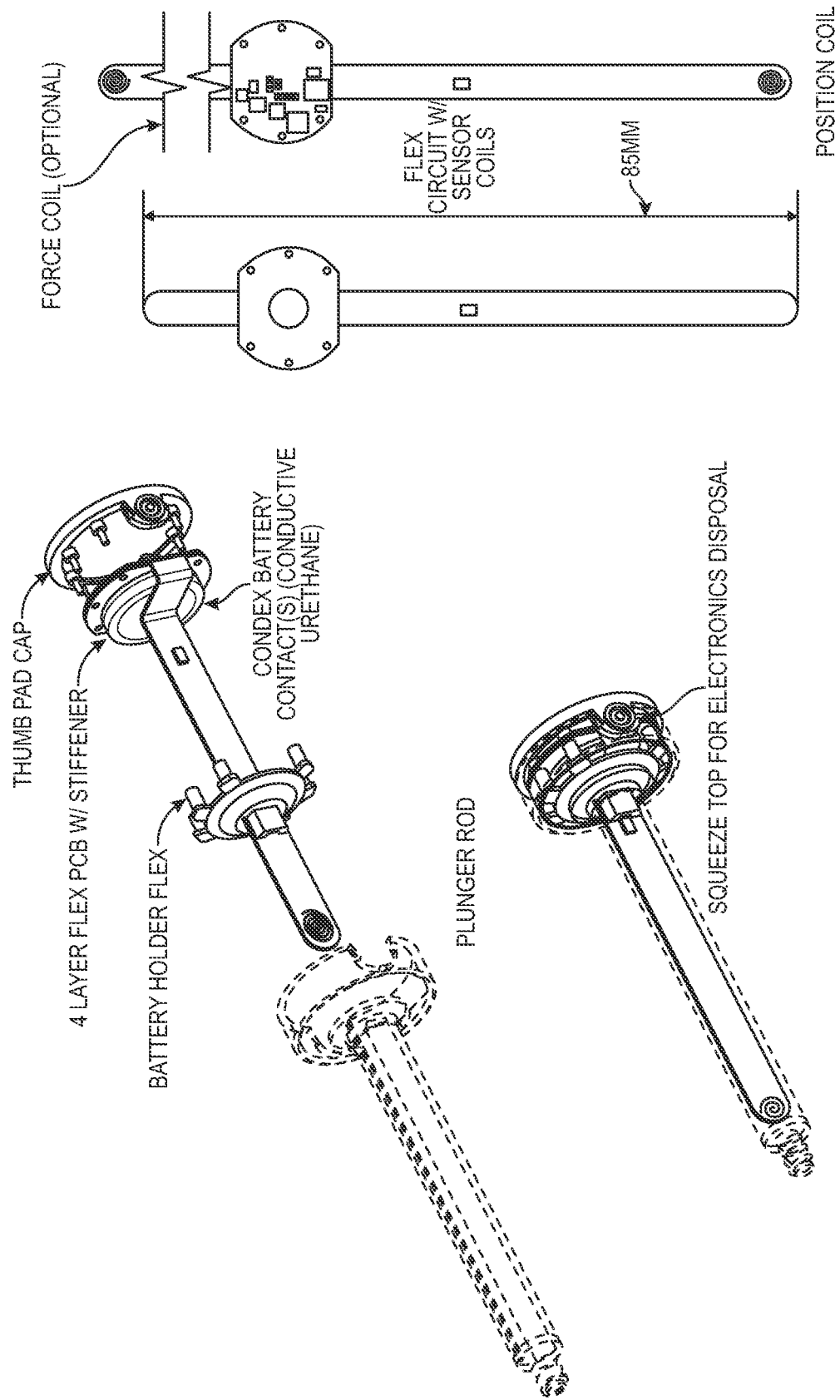
FIG. 12 is a three dimensional rendering of a syringe stopper rod and a deflection component comprising a position coil, an optional force coil, a flexible circuit assembly, sensor, and battery assembly according to one embodiment of the disclosure.

Turning now to FIG. 12, a three dimensional view of a deflection component is depicted. The depicted embodiment comprises a position coil disposed at a first end of an extension component, and an optional force coil disposed on a second end of the extension component. The extension component is composed of a flexible circuit board material, and includes a sensor component. In use, the extension component is folded and assembled, and placed inside the syringe stopper rod.

Figure 13:
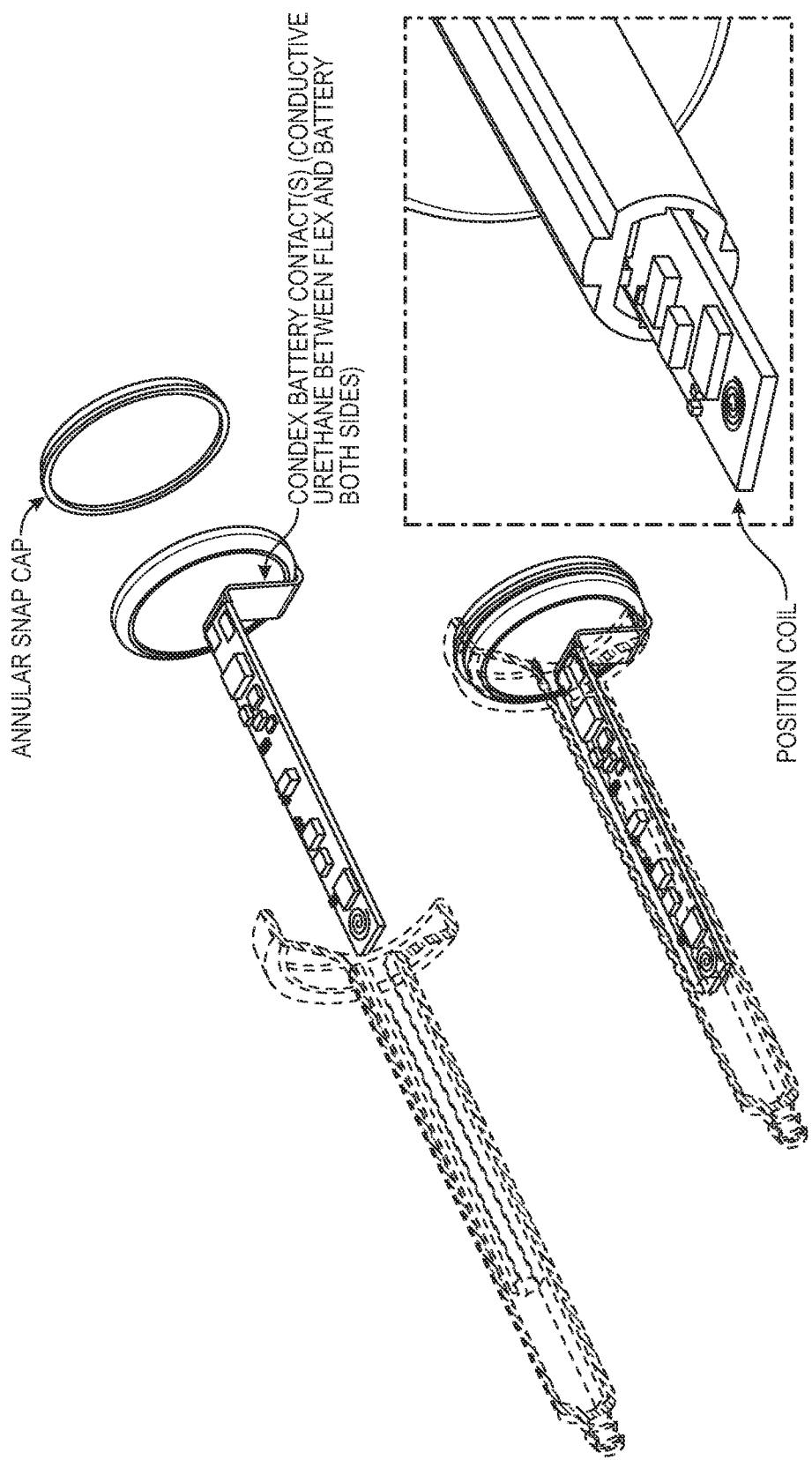
FIG. 13 is a three dimensional rendering of a syringe stopper rod and a deflection component comprising a flexible circuit assembly, a position coil, and a battery assembly.

Turning now to FIG. 13, a three dimensional view of another deflection component is depicted. The depicted embodiment comprises a position coil disposed at a first end of an extension component. In this embodiment, the sensor component is disposed on a portion of the extension component, and is composed of a rigid circuit board material. Another portion of the extension component is composed of a flexible circuit board material that wraps around the battery, which is disposed inside the thumb pad of the syringe stopper rod. In use, the extension component and sensor are assembled and placed inside the syringe stopper rod, as depicted, with the position coil protruding from an interior cavity, but still positioned inside the housing of the syringe stopper rod.

Figure 14:
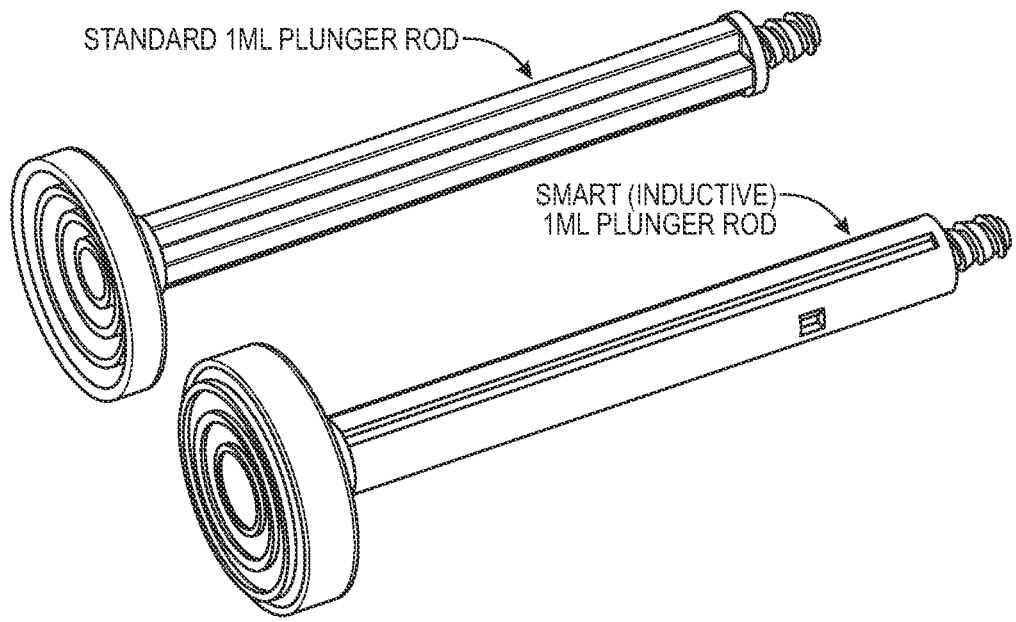
FIG. 14 is a three dimensional rendering of a standard 1 mL syringe plunger rod and a Smart 1 mL plunger rod according to one embodiment of the disclosure.

Turning now to FIG. 14, two three dimensional renderings of syringe stopper rods are depicted. The first is a standard 1 mL syringe stopper rod, or "plunger" rod. The second is a Smart syringe stopper rod in accordance with embodiments of the disclosure. The Smart syringe stopper rod contains the internal components depicted in, e.g., FIGS. 12-13, but still has roughly the same dimensions are the depicted "standard" 1 mL syringe stopper rod.

Figure 16:
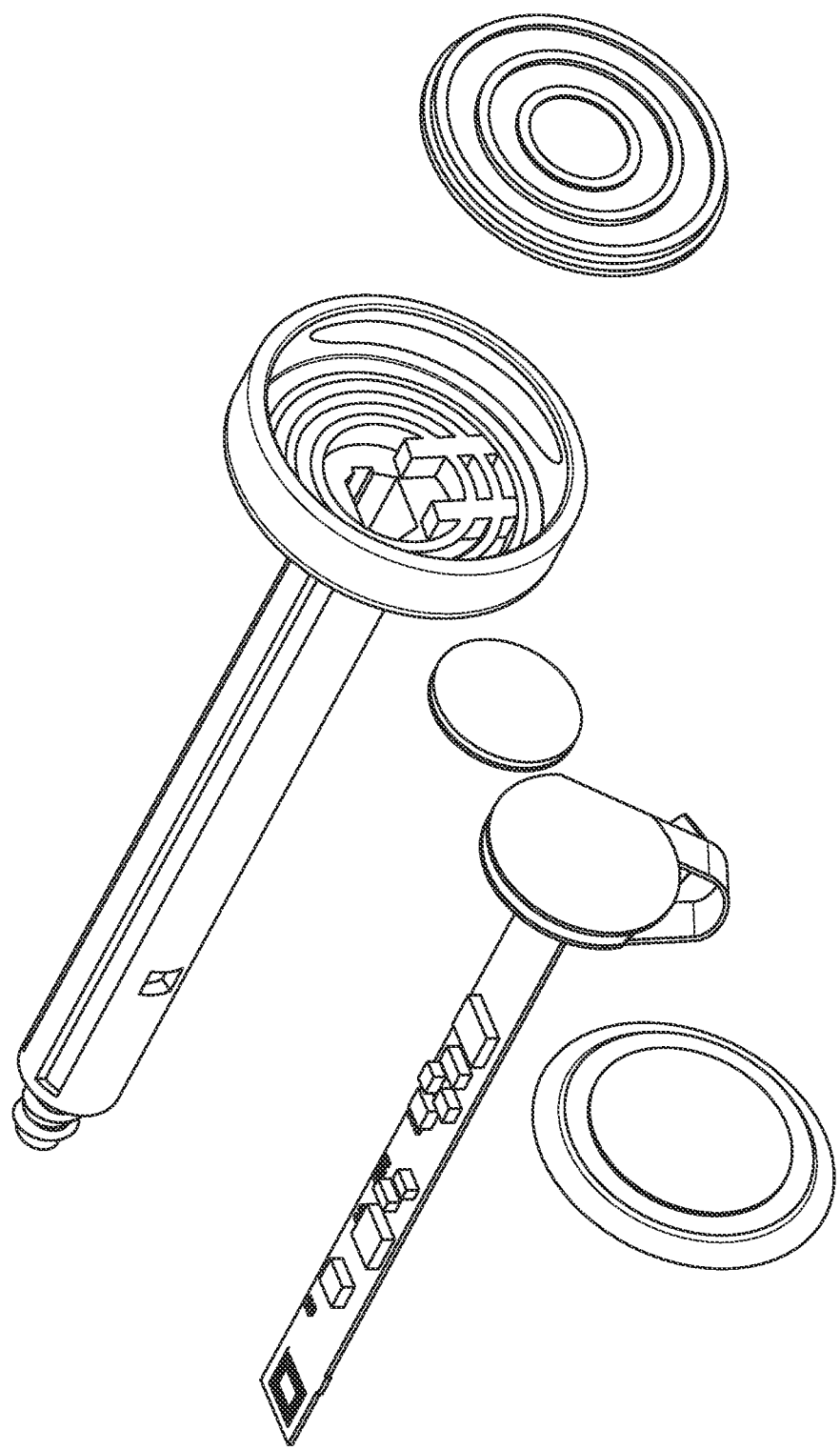
FIG. 16 is a three dimensional rendering showing various individual components of a system according to one embodiment of the disclosure.
Figure 17:
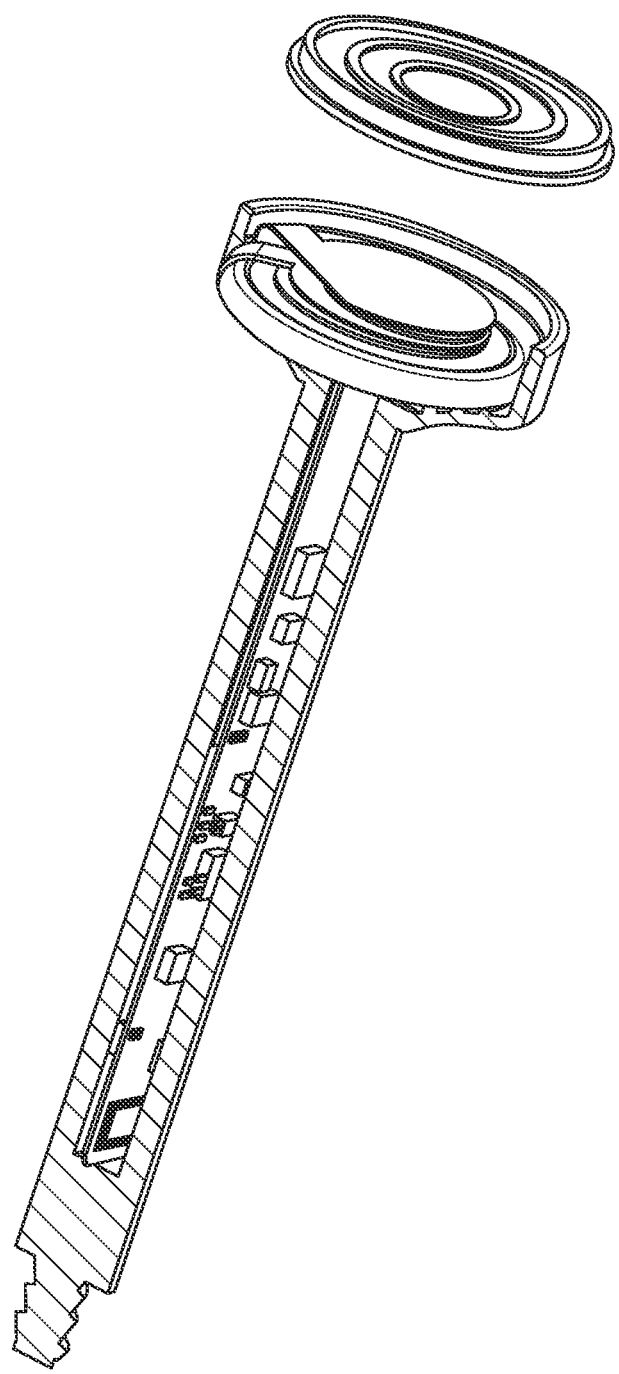
FIG. 17 is three dimensional rendering showing an assembled view of the components depicted in FIG. 16.
Figure 18:
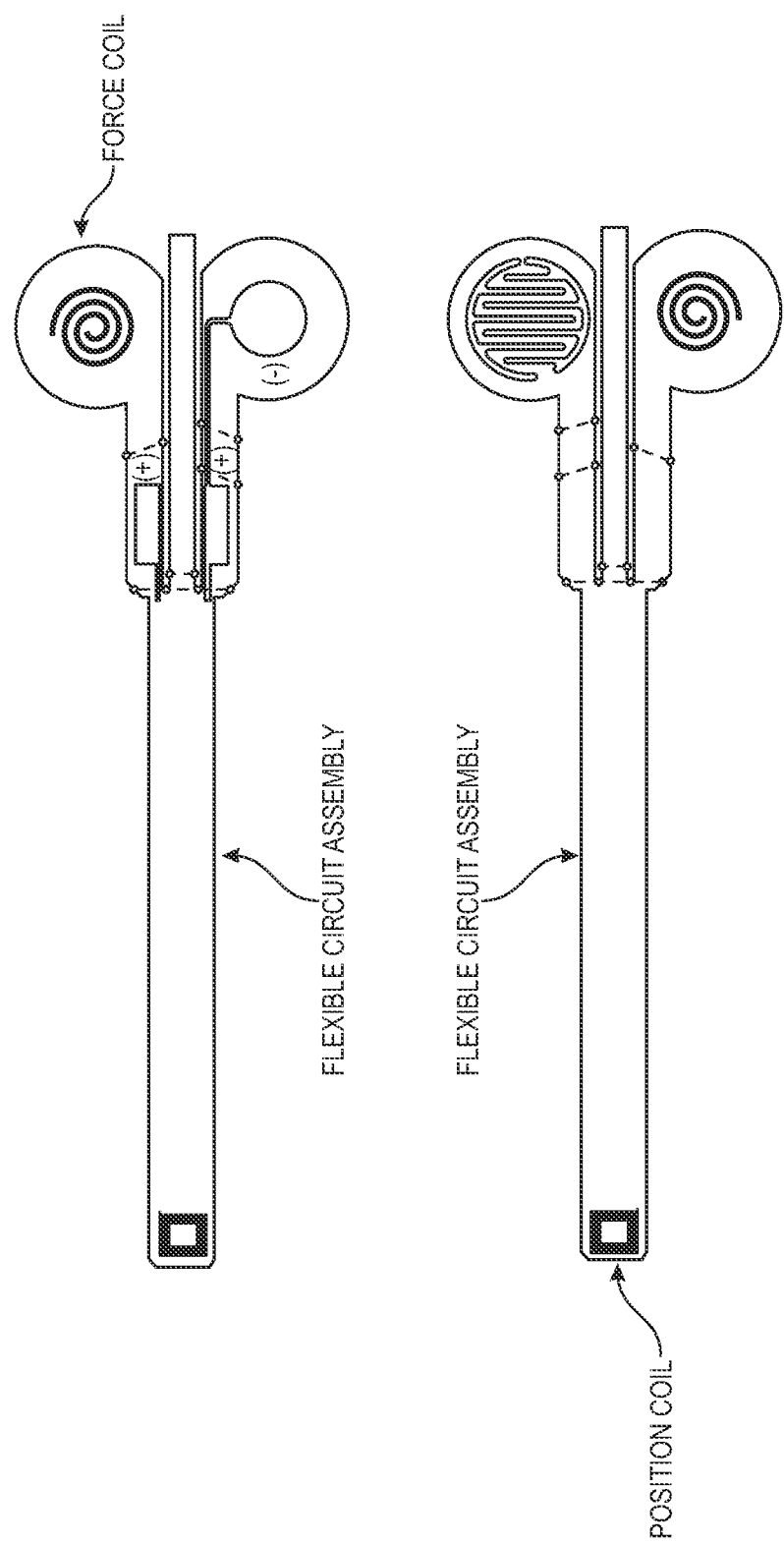
FIG. 18 is a diagram of a deflection component and flexible circuit assembly according to one embodiment of the disclosure.
Figure 19:
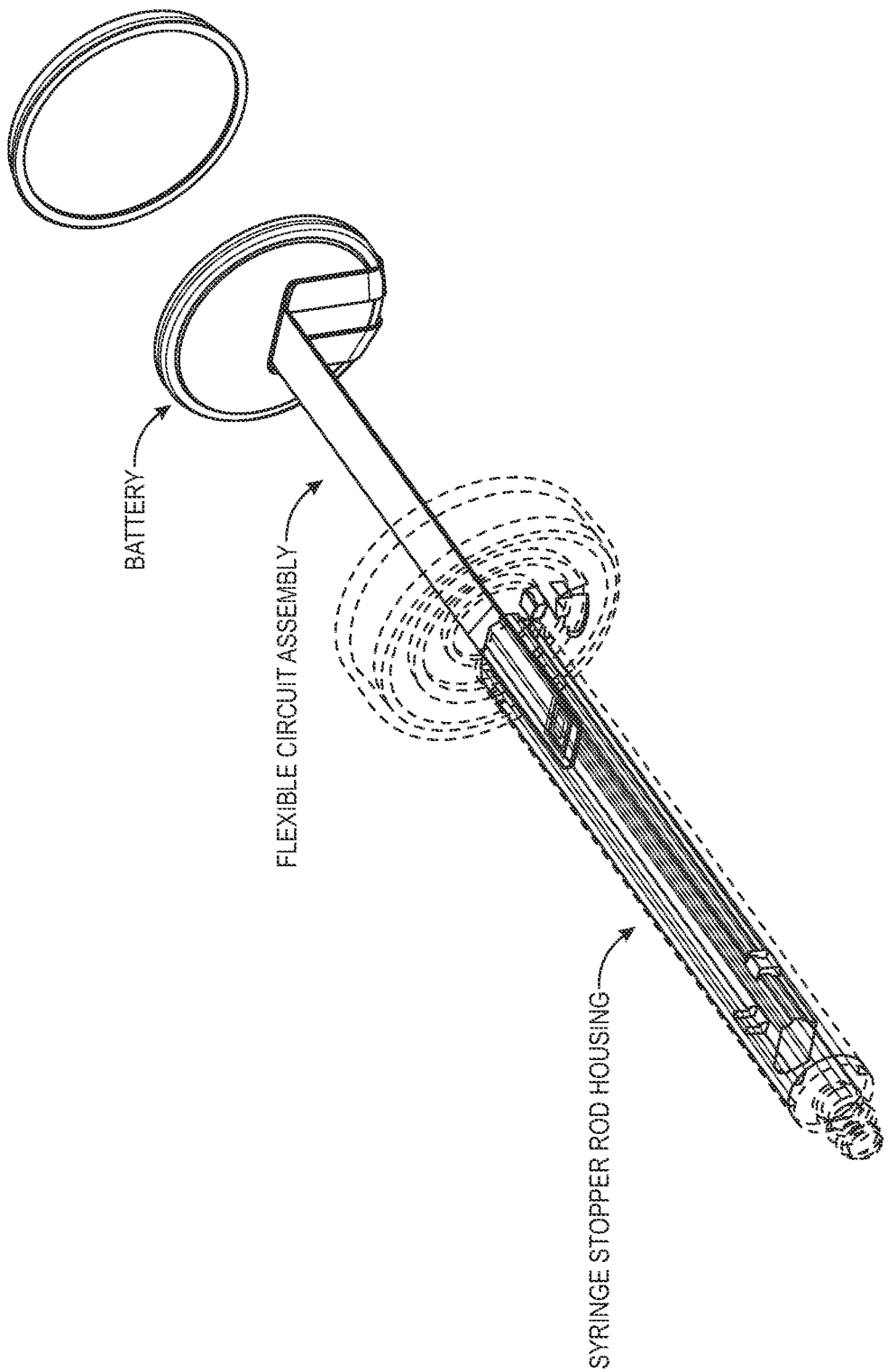
FIG. 19 is an exploded three dimensional view of various components of a syringe stopper rod according to one embodiment of the disclosure.
Figure 20:
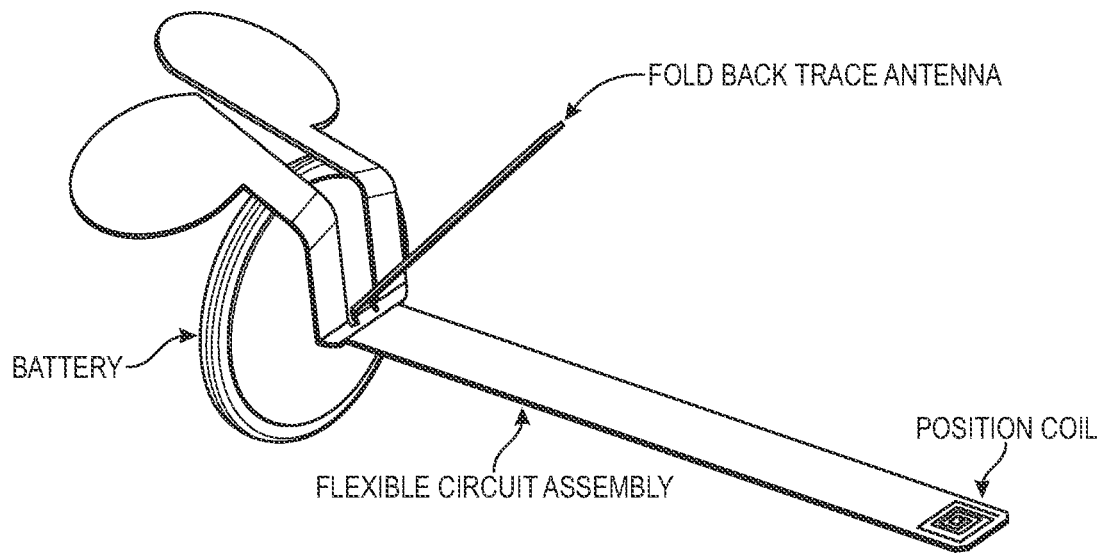
FIG. 20 is a three dimensional rendering showing folding and assembly of a flexible circuit assembly and deflection component in accordance with one embodiment of the disclosure.
Figure 21:
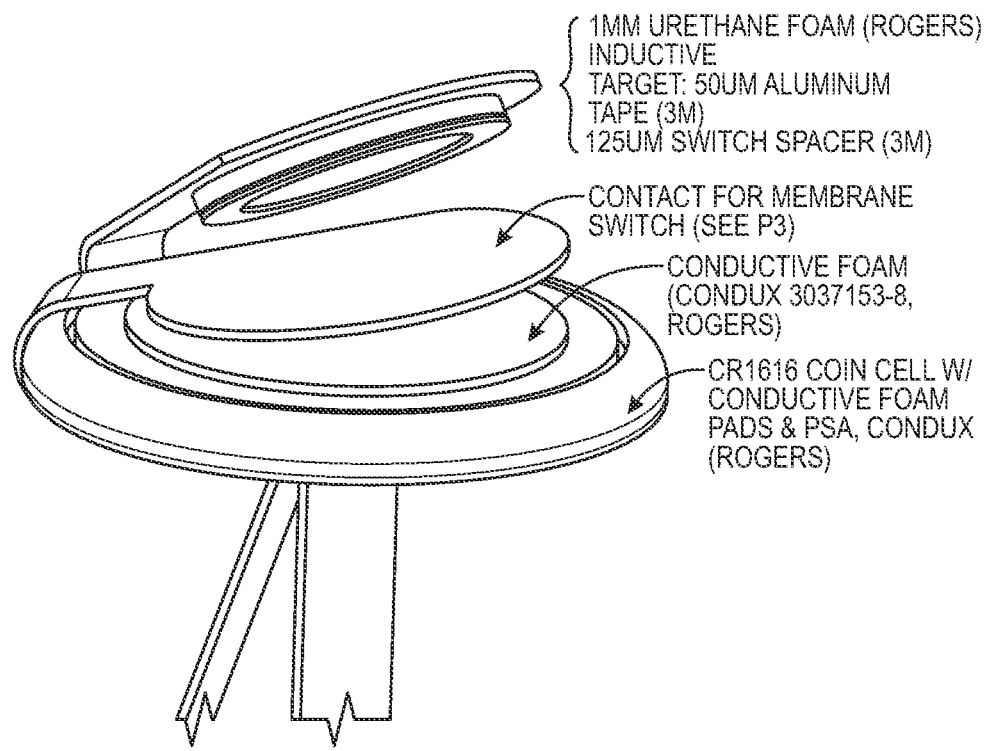
FIG. 21 is a three dimensional rendering showing a detailed view of the assembly of the components depicted in FIGS. 18-20.
Figure 22:
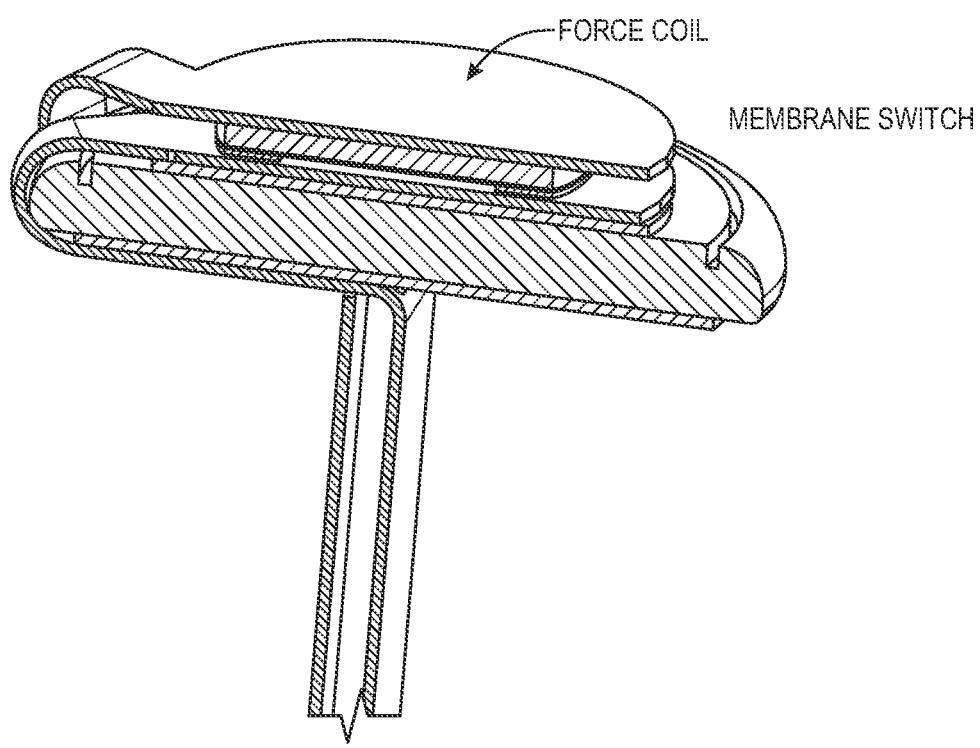
FIG. 22 is a three dimensional rendering showing a detailed view of the assembled components depicted in FIGS. 18-21.

Turning now to FIGS. 16-22, the components of a Smart syringe stopper rod are depicted in various phases of assembly. FIG. 16 shows a syringe stopper rod housing, a flexible circuit assembly, a battery, and components of the thumb pad. FIG. 17 shows these elements assembled and inserted inside the syringe stopper rod housing. FIG. 18 is a diagram showing the elements of the flexible circuit assembly, which include a position coil, a force coil, and an antenna. FIGS. 19-22 show how the flexible circuit assembly is folded around the other components of the system and configured for insertion into the syringe stopper rod housing.

Delivery Signatures

As reviewed above, aspects of the disclosure include detection of a delivery signature by a subject sensor and/or data management component. Delivery signatures in accordance with embodiments can comprise any of a variety of data components. For example, in embodiments where a deflection component comprises a plurality of trigger switches, a delivery signature can comprises data relating to a deflection order of the trigger switches, a deflection duration of each trigger switch, one or more time intervals corresponding to a time between a deflection of a first trigger switch and a deflection of a second trigger switch, or any combination thereof.

In embodiments where a deflection component and/or a sensor component comprises a force sensor, a delivery signature can comprise an injection force profile corresponding to an injection force applied to a portion of a subject device by a user. For example, in some embodiments, an injection force profile can comprise a break loose force, a glide force, an end of dose force, or any combination thereof. In certain embodiments, an injection force profile can comprise a time interval associated with the break loose force, a time interval associated with the glide force, a time interval associated with the end of dose force, or any combination thereof.

In embodiments where a deflection component comprises a first and second inductive sensor coil and a first and second detection target, a delivery signature can comprise a detection signal from the first and second inductive sensor coils, corresponding to detection of the first and second detection targets. In such embodiments, where the second detection target comprises a uniform geometry, a delivery signature can comprise detection of the uniform geometry of the second detection target by the second inductive sensor coil, which can be located on an extension component of the deflection component. Further, in such embodiments, where the second detection target comprises a repeating geometry, a delivery signature can comprise detection of the repeating geometry by the second inductive sensor coil, which can be located on an extension component of the deflection component. Additionally, in embodiments where a detection target comprises a variable geometry, a delivery signature can comprise a detection signal from one or more attributes of the variable geometry, such as a proportional signal.

Delivery signatures in accordance with embodiments of the disclosure can have a characteristic shape that is indicative of a delivery stroke. Aspects of the disclosure involve detecting all or a portion of a delivery signature in order to measure a progression of a delivery stroke or a completion of a delivery stroke. In some embodiments, a delivery signature is detected and/or analyzed by a sensor component. In some embodiments, a delivery signature is detected and/or analyzed by a data management component. In some embodiments, a delivery signature is compared to a reference signature, and if the delivery signature matches the reference signature within acceptable tolerance levels, a successful delivery stroke is recorded. In some embodiments, a data management component is programmed with one or more algorithms that are adapted to apply a set of rules to determine whether a delivery signature sufficiently conforms to a predetermined reference signature.

In one embodiment, a delivery signature is generated when a plurality of trigger switches is deflected in a given direction for a specified period of time. For example, when all three of the trigger switches in the trigger switch assembly depicted in FIG. 7 are deflected in an inward direction for a specified period of time (e.g., for 3 or more seconds, such as 4, 5, 6, 7, 8, 9, and 10 or more seconds), the data management component determines that the delivery signature conforms to a reference signature.

Figure 27:
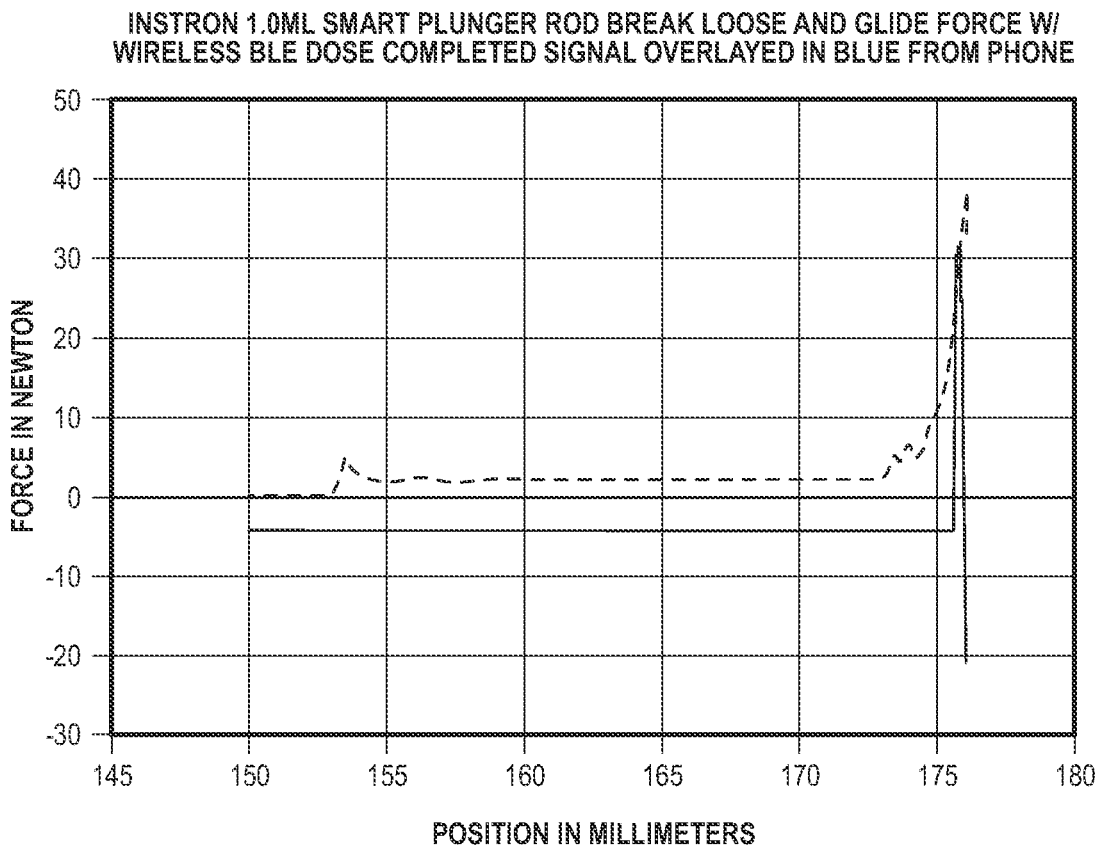
FIG. 27 is a graph showing force as a function of position obtained from a force measurement experiment performed on a drug delivery system according to one embodiment of the disclosure.

Turning now to FIG. 27, a graph of an injection force profile is depicted. In the graph, force is plotted (in Newtons) as a function of position (in millimeters). The graph shows a break loose force (spike located between 153 mm and 155 mm, with a maximum force value of approximately 5 Newtons), a glide force (plateau located between 155 mm and 173 mm, with a constant force value of approximately 2 Newtons) and an end of dose force (located between 173 mm and 176 mm, with a maximum force value of approximately 38 Newtons).

Figure 28:
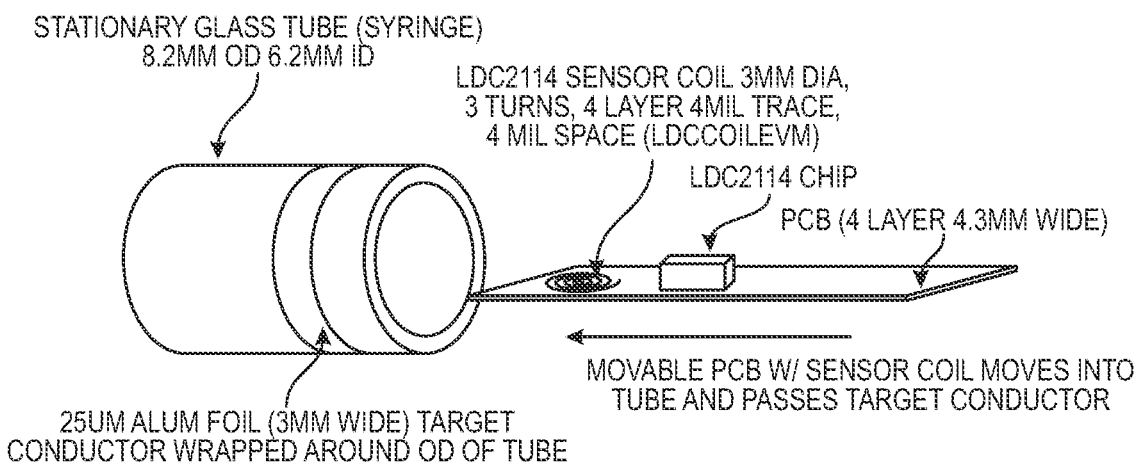
FIG. 28 is an illustration of a deflection component comprising an inductive sensor coil being inserted into a stationary glass tube with a detection target mounted on the glass tube.

Turning now to FIG. 28, a syringe barrel and an extension component are depicted. The syringe barrel comprises two annular rings disposed on the outer surface, which serve as detection targets for the inductive sensor coil disposed on the extension component. The depicted detection target represents an example of a repeating geometry. If only one annular ring were present, this would be an example of a uniform geometry detection target. In use, during a delivery stroke, the extension component is passed along the interior of the syringe barrel, and the inductive sensor coil sequentially passes each of the annular rings. In some embodiments, the annular rings can be disposed on an external surface of a syringe barrel, while in some embodiments, the annular rings can be incorporated into a label that is wrapped around the syringe barrel.

Figure 29:
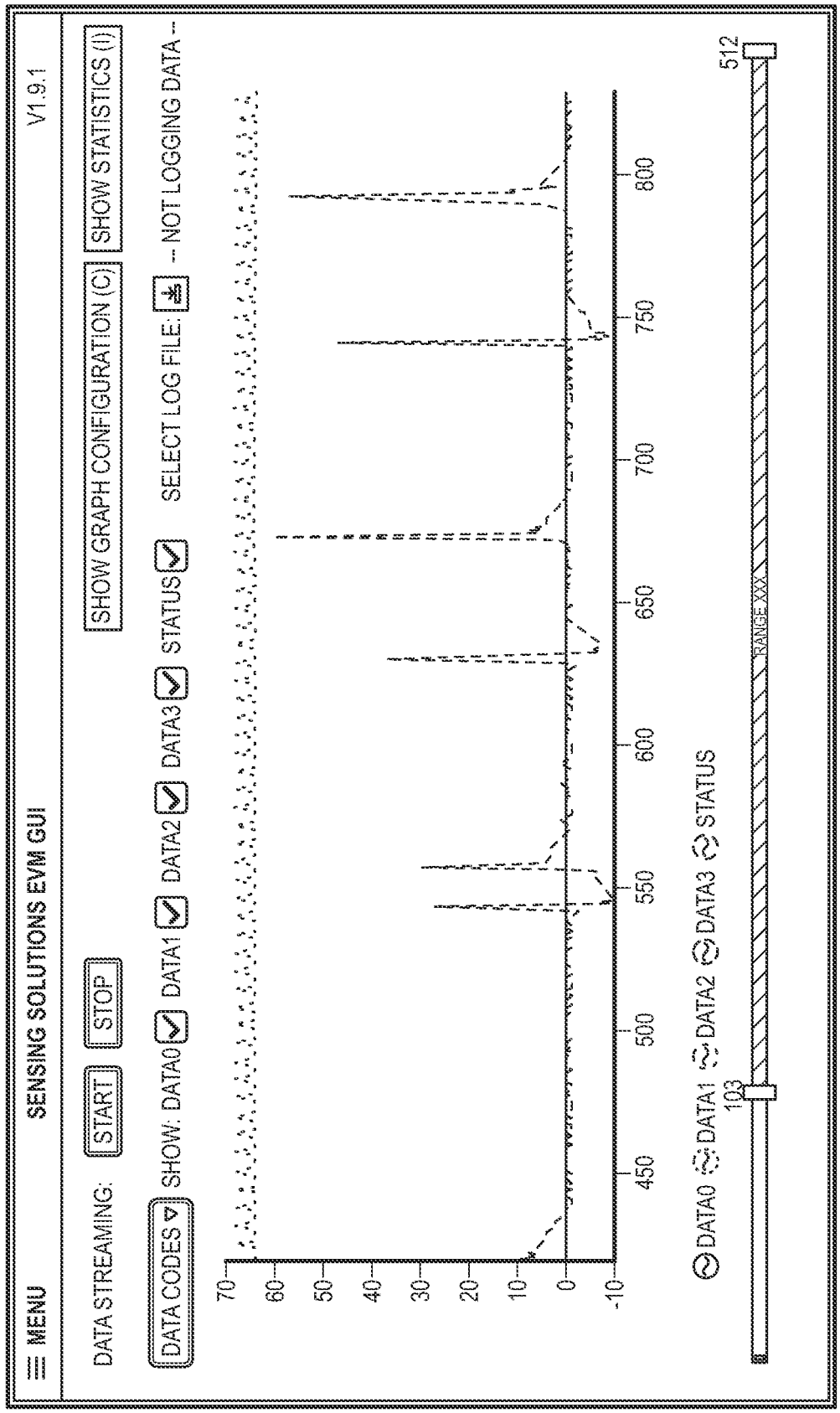
FIG. 29 is a graph showing sensation of a detection target by an inductive sensor coil according to one embodiment of the disclosure.
Figure 30:
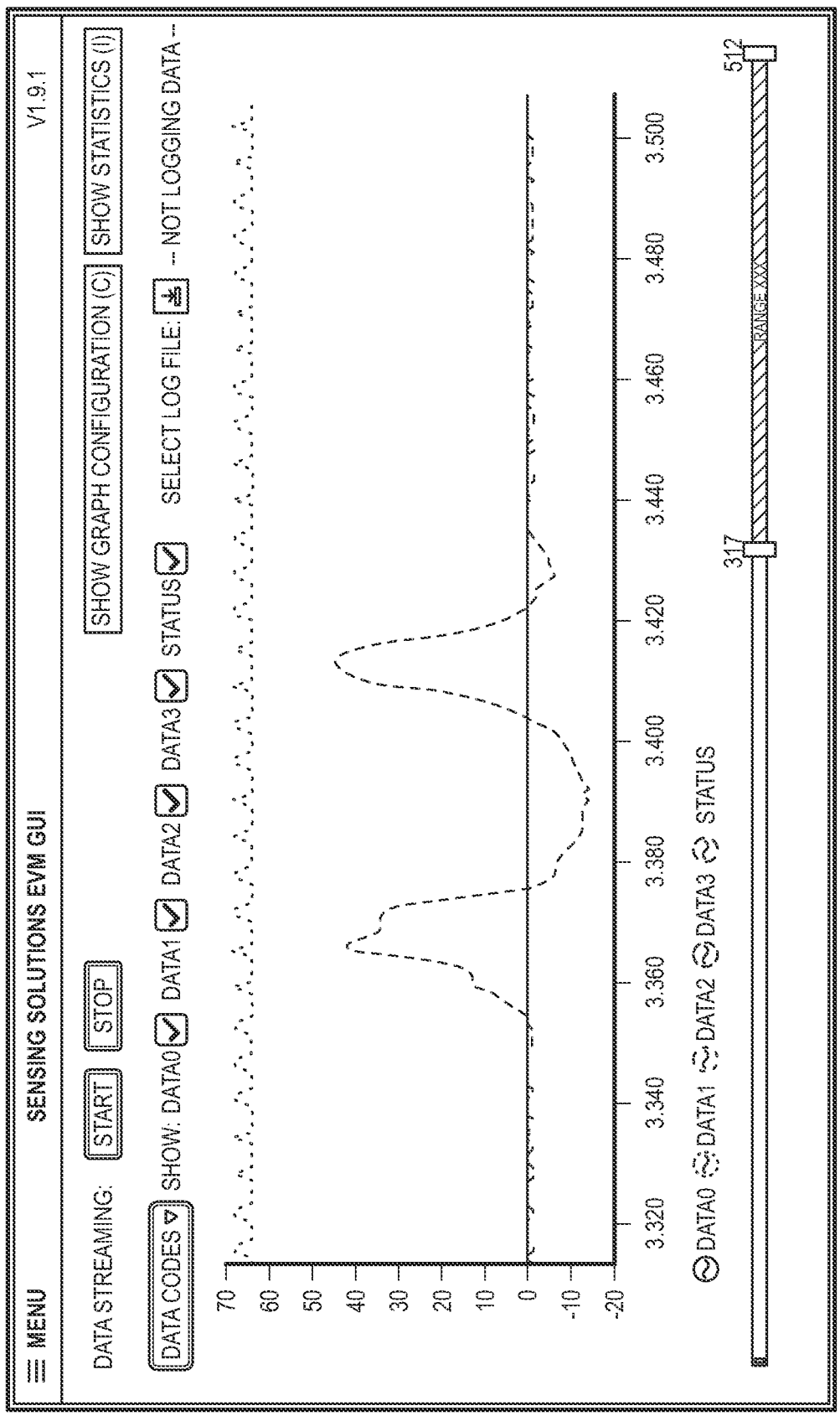
FIG. 30 is a graph showing sensation of a detection target by an inductive sensor coil according to one embodiment of the disclosure.

Turning now to FIG. 29, a graph is shown, which depicts data generated from the embodiment depicted in FIG. 28. In this graph, pairs of detection spikes are shown where the inductive sensor coil passed along the syringe barrel and each of the annular rings. Each pair of detection spikes represents a first signal from the first annular ring, and a second signal from the second annular ring. FIG. 30 depicts data generated from the same embodiment, depicted in FIG. 28, but with a lower rate of speed when passing the first and second annular ring detection targets with the inductive sensor coil. In this graph, each detection spike has a wider base, demonstrating a larger and more defined signal distribution obtained from passing the detection targets at a lower rate of speed.

Actuation Component

Aspects of the disclosure include actuation components that are configured to move, thereby causing a drug to be dispensed from the drug reservoir and injected into the patient. Actuation components in accordance with embodiments of the disclosure can generally be actuated by any suitable mechanism. In some embodiments, an actuation component is configured to be moved manually by a user. In some embodiments, an actuation component is configured to be moved automatically by one or more driver components (e.g., one or more mechanical, electrical, or electromechanical controllers). In certain embodiments, a subject drug delivery system or device in configured to automatically inject a drug dose into the patient, and is characterized as an auto-injector.

In some embodiments, an actuation component can include a controller that is coupled to one or more assemblies or subassemblies of the subject systems or devices. The controller can be configured or adapted (e.g., programmed, if the controller comprises an electrical or electromechanical component) to move the actuation component in response to a user input or an activation signal.

In some embodiments, an actuation component can comprise one or more coupling components that are configured or adapted to mechanically connect the actuation component to one or more additional components of the subject systems or devices. Coupling components in accordance with embodiments of the disclosure broadly include threaded couplers, adhesive couplers, snap-fit couplers, magnetic couplers, or any combination thereof. For example, in one embodiment, an actuation component comprises a syringe stopper rod that comprises a threaded coupler located at the distal end. The threaded coupler is configured to screw into a proximal end of a syringe stopper to physically couple the syringe stopper rod to the syringe stopper.

Figure 23:
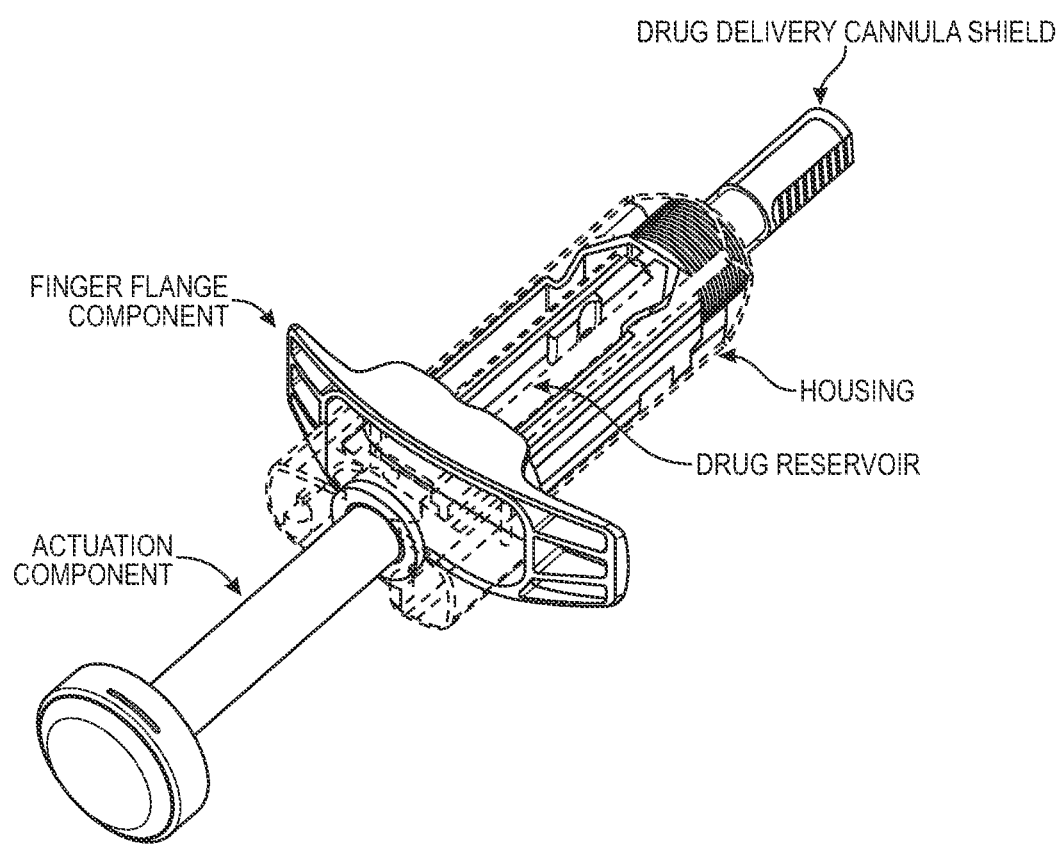
FIG. 23 is a three dimensional rendering of a drug delivery system according to one embodiment of the disclosure.
Figure 24:
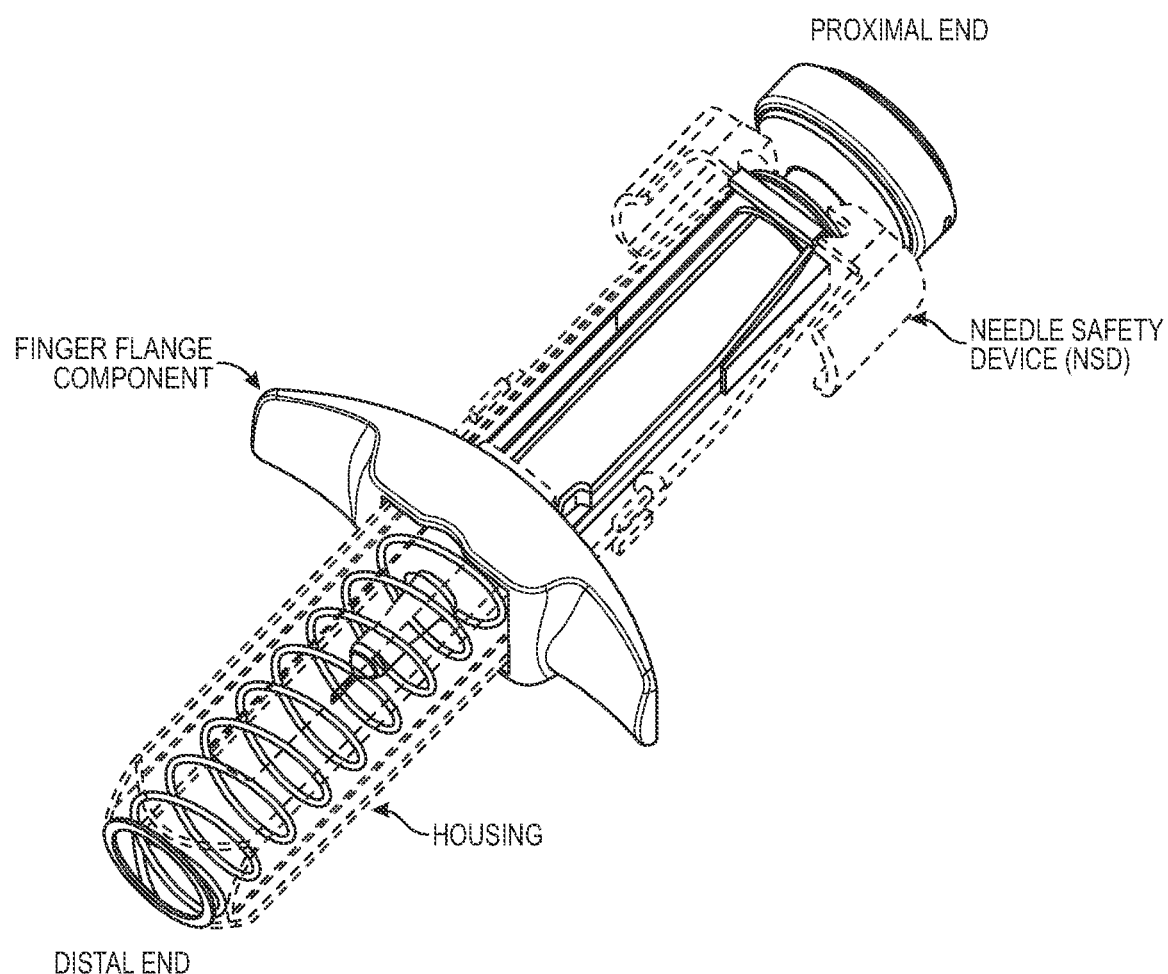
FIG. 24 is a three dimensional rendering of a drug delivery system according to one embodiment of the disclosure.
Figure 25:
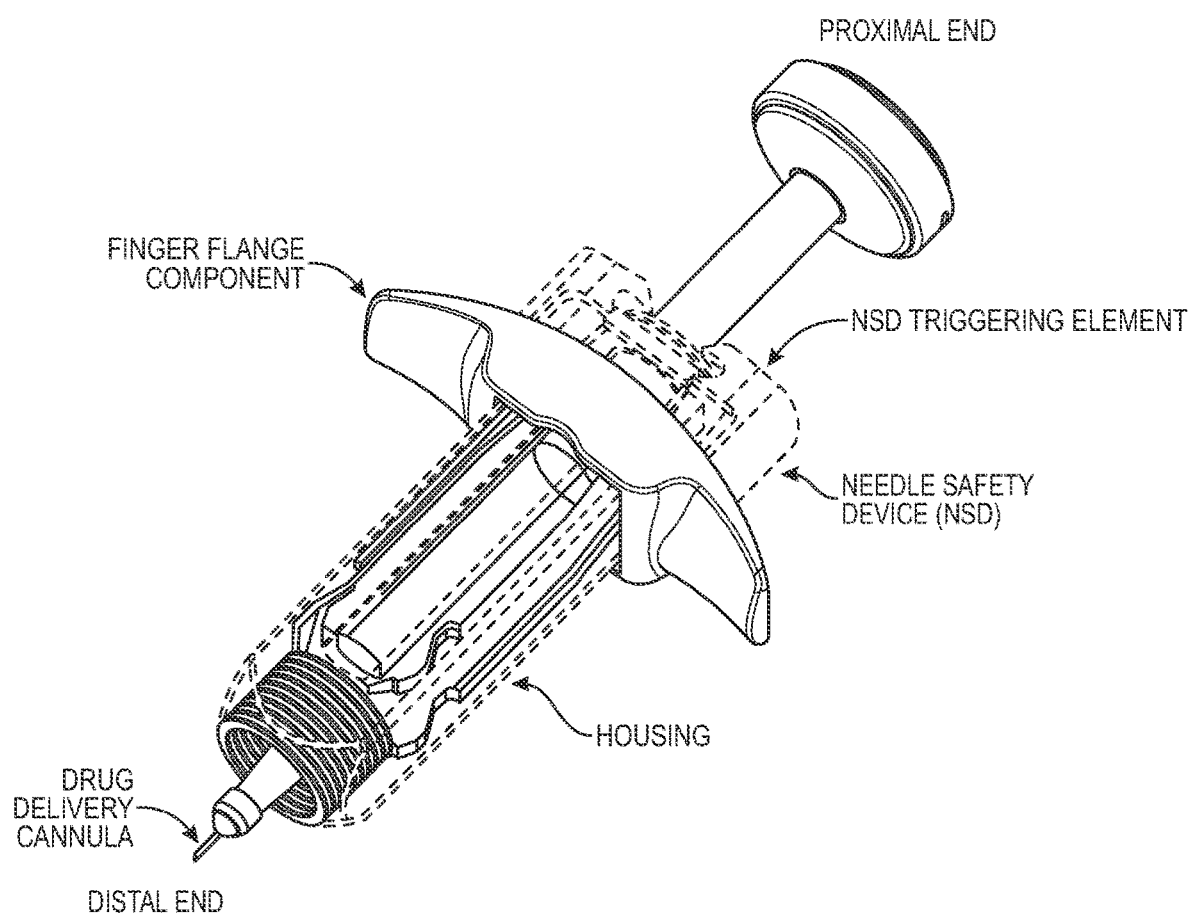
FIG. 25 is a three dimensional rendering of a drug delivery system according to one embodiment of the disclosure.

FIGS. 23-25 depict drug delivery devices in accordance with embodiments of the disclosure, comprising an actuation component in the form of a syringe stopper rod, a finger flange component, a drug reservoir, a housing, a drug delivery cannula, a drug delivery cannula shield, and a needle safety device.

Indicator Component

Aspects of the disclosure include indicator components that are configured or adapted to communicate one or more operational states of the subject drug delivery systems or devices to a user. In use, a given operational state of a subject drug delivery system or device can be assigned a specific indicator signal, and the subject indicator components can be used to communicate the specific indicator signal to a user, thereby indicating to the user that the system or device is in the indicated operational state. Indicator components in accordance with embodiments of the disclosure broadly include visual, haptic and auditory indicators, each of which is described in further detail herein.

Aspects of the disclosure include visual indicator components that are configured or adapted to display a visual signal regarding an operational state of a subject system or device to a user. In some embodiments, a visual indicator comprises a light-emitting component. Light emitting components in accordance with embodiments of the disclosure include, without limitation, light emitting diodes (LEDs) and organic light emitting diodes (OLEDs). In some embodiments, a visual indicator comprises a light pipe (also referred to as a light tube). In some embodiments, a light pipe comprises a hollow structure that is configured to contain light within the structure by utilizing a reflective lining. In some embodiments, a light pipe comprises a transparent solid material that is configured to contain light within the material by utilizing total internal reflection. In some embodiments, a visual indicator comprises a diffuser component (e.g., a light pipe diffuser) that is configured to uniformly spread a visual signal (e.g., light from an LED) over a defined area. In some embodiments, a visual indicator component comprises a light pipe and a light pipe diffuser. Visual indicator components in accordance with embodiments of the disclosure can be configured or adapted to generate visual signals having any color (e.g., red, orange, yellow, green, blue, purple) or any combination thereof. In some embodiments, an operational state of a subject system or device can be assigned a specific color. For example, in one embodiment, an unready operational state is assigned the color red, and when the system or device is in an unready state, a red color is displayed to a user using a visual indicator component. In some embodiments, a visual indicator component can be configured to flash a visual indicator on and off in a particular sequence (e.g., a series of three short flashes) or to remain constantly on to provide an indication of an operational state. Other indicator settings in accordance with embodiments of the disclosure include: attempting to connect to a data management component (e.g., flashing yellow or blue indicator light), and connected to a data management component (e.g., flashing or solid green or blue indicator light). Any of a variety of "ready" or "unready" states can be indicated to a user. For example, in some embodiments, an indicator component is configured to indicate that a drug reservoir has reached a suitable temperature for use. In some embodiments, an indicator component is configured to indicate to a user that the device is attempting to connect to a wireless network or a data management component. In some embodiments, an indicator component is configured to indicate to a user that the device is connected to a wireless network or a data management component. In some embodiments, indicator component(s) can be located on a GUI of a mobile device.

Aspects of the disclosure include haptic indicator components that are configured or adapted to generate one or more vibration signals that are specific to an operational state of a subject system or device. In some embodiments, a haptic indicator comprises a vibration generator component. Vibration generator components in accordance with embodiments of the disclosure are configured or adapted to generate vibrations having any desired combination of amplitude, frequency and duration in order to generate a plurality of unique vibration signals. For example, in one embodiment, an unready operational state can be assigned a vibration signal that consists of a single, high amplitude vibration that has a duration of one second.

Aspects of the disclosure include auditory indicator components that are configured or adapted to generate one or more auditory signals that are specific to an operational state of a subject system or device. In some embodiments, an auditory indicator comprises a sound generator component. Sound generator components in accordance with embodiments of the disclosure are configured or adapted to generate a plurality of unique sounds having a plurality of different tones and/or volumes. For example, in one embodiment, an unready operational state can be assigned a sound that consists of a single, high-volume buzzer sound.

Indicator components in accordance with embodiments of the disclosure can be mounted in any suitable location on the subject systems or devices. For example, in some embodiments, an indicator component can be mounted in a housing that is positioned anywhere on the system or device. In some embodiments, an indicator component can comprise a plurality of individual components that work in concert to generate a desired indicator signal. For example, in one embodiment, a visual indicator component comprises an LED that generates a visible light signal, and also comprises a light pipe that transfers the visible light from the LED to one or more locations on the subject system or device. In some embodiments, a visual indicator further comprises a light pipe diffuser that evenly spreads the visible light signal over a desired location (e.g., over the entire area of a thumb pad, over an entire indicator window).

In one embodiment, an indicator component is mounted in a thumb pad that is attached to an actuation component (e.g., a syringe stopper rod, as described further herein). In some embodiments, an indicator component is configured to be removably coupled to subject drug delivery system or device. For example, in some embodiments, an indicator component is mounted in a thumb pad, and the thumb pad is configured to be removably coupled to a distal end of a syringe stopper rod.

Housing Component

Aspects of the disclosure include one or more housing components that are formed from suitable materials, such as, e.g., glass, plastic, metal, or any combination thereof. In some embodiments, one or more individual components of the subject drug delivery systems or devices can be located within a single housing and formed into a single unit. In some embodiments, one or more components of the subject systems or devices can be located in a first housing component, and one or more additional components of the subject systems or devices can be located in a second housing component, and the first and second housing components can be operably coupled to one another to form a single unit.

In some embodiments, a housing comprises one or more transparent or semitransparent windows that are made of a material that is at least partially transparent to light, and is configured to allow ambient light to pass through the housing to reach a light sensor positioned therein. In some embodiments, a housing comprises one or more windows or openings that allow one or more components of the systems or devices to physically pass through.

Drug Reservoir

Aspects of the disclosure include a drug reservoir that is configured or adapted to contain a volume of a drug. In certain embodiments, a drug reservoir is operably coupled to one or more additional components of a subject system or device (e.g., an actuation component and/or a drug delivery cannula). In some embodiments, a drug can comprise a large or small molecule composition. In some embodiments, a drug can comprise a biological composition. Non-limiting examples of biological compositions include proteins (e.g., antibodies). In some embodiments, a drug can be in a fluid or liquid form, although the subject drug delivery systems and devices are not limited to a particular drug state. For example, in some embodiments, a drug reservoir can contain a liquid solution, a gel, or a solid (e.g., a lyophilized) drug substance. In some embodiments, a subject drug delivery system or device can comprise a plurality of drug reservoirs. In some embodiments, a first drug reservoir can contain, e.g., a lyophilized drug and a second drug reservoir can contain a liquid that can be used to reconstitute the lyophilized drug. In some embodiments, a subject drug delivery system or device is configured to carry out a mixing procedure, wherein a lyophilized drug is mixed with a reconstitution solution before the drug is administered to the patient.

Drug reservoirs in accordance with embodiments of the disclosure can be constructed from any suitable material, such as, e.g., glass, plastic, metal, or any combination thereof. In certain embodiments, a drug reservoir is configured or adapted to be non-reactive with a drug that is to be stored in the reservoir. In certain embodiments, a drug reservoir is configured to hold a volume of drug that ranges from about 10 µL up to about 1,000 mL, such as about 15, 20, 25, 30, 35, 40, 45, 50, 55, 60, 65, 70, 75, 80, 85, 90, 100, 125, 150, 200, 250, 300, 350, 400, 450, 500, 550, 600, 650, 700, 750, 800, 850, 900 or 950 µL or more, such as about 1, 5, 10, 15, 20 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, or about 950 mL.

In some embodiments, a drug reservoir is configured or adapted to be stored at a variety of different temperatures. In some embodiments, a drug reservoir is configured to be stored at a temperature ranging from about −100° C. to about 40° C., such about −90, −80, −70, −60, −50, −40, −30, −20, −10, 0, 2-8, 10, 15, 20, 25, 30 or 35° C.

Drug reservoirs in accordance with embodiments of the disclosure are configured to maintain their contents in a sterile condition. In certain embodiments, a drug reservoir can comprise at least one sterile barrier that is configured to maintain the sterility of the reservoir's contents prior to use in a subject system or device, and is configured to be removed when the drug reservoir is operably coupled to a subject system or device. In some embodiments, a drug reservoir is configured to be removably coupled to one more components of a subject system or device (e.g., is configured to be removably coupled to an actuation component of a subject drug delivery device).

In some embodiments, a drug reservoir comprises a syringe, consisting of a stopper that fits tightly inside a syringe barrel. Movement of the stopper along the inside of the syringe barrel results in movement of a liquid that is present inside the syringe barrel. In some embodiments, a stopper is configured or adapted to be operably coupled to an actuation component (e.g., a syringe stopper rod) that is configured to move the stopper. In some embodiments, an end of the syringe that is opposite the stopper comprises an opening through which a liquid can be taken in or expelled, depending on the direction of motion of the stopper. In some embodiments, a syringe can be operably coupled to a drug delivery cannula (e.g., a needle or a catheter). In some embodiments, a drug delivery cannula can be removably coupled to a syringe. In some embodiments, a drug delivery cannula can be non-removably coupled to a syringe (e.g., a staked needle syringe). In some embodiments, a syringe is a pre-filled syringe, which contains a predetermined volume of liquid.

Figure 26A:
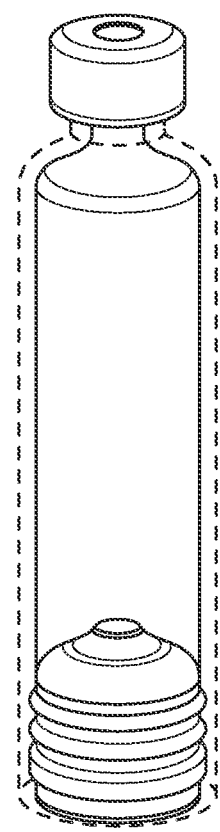
FIG. 26A is a three dimensional rendering of a drug cartridge according to one embodiment of the disclosure.
Figure 26B:
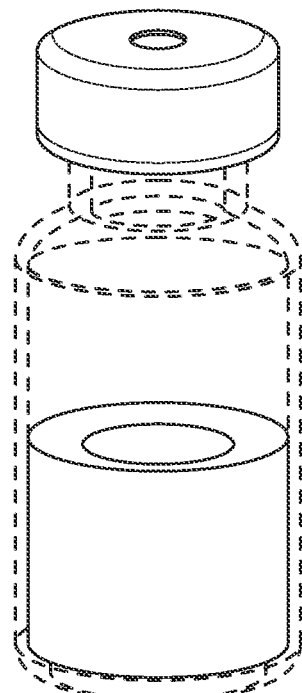
FIG. 26B is three dimensional rendering of a vial according to one embodiment of the disclosure.

In some embodiments, a drug reservoir comprises a vial. Vials in accordance with embodiments of the disclosure are composed of any suitable material, e.g., glass, plastic, metal, or any combination thereof, and comprise one open end. In some embodiments, a vial comprises a removable cap that is configured to close the open end. In some embodiments, a cap comprises a stopper that is configured to be punctured, e.g., by a drug delivery cannula, or by one or more fluid coupler components that are configured to transfer the contents of the vial from one position to another within a subject system or device. In some embodiments, a stopper is a rubber stopper that is covered with a protective layer of metal to prevent accidental punctures of the stopper prior to use. FIG. 26, Panel B depicts one embodiment of a vial.

In some embodiments, a drug reservoir comprises a cartridge. Cartridges in accordance with embodiments of the disclosure are composed of any suitable material, e.g., glass, plastic, metal, or any combination thereof, and comprise one or more openings that are configured to operably couple to a subject drug delivery system or device. In some embodiments, a cartridge comprises a removable barrier that is configured to cover the one or more openings prior to use. FIG. 26, Panel A depicts one embodiment of a cartridge.

Aspects of the disclosure include a drug reservoir that comprises a memory component (as described herein) that is configured or adapted to store one or more drug identification characteristics. Memory components in accordance with embodiments of the disclosure can be volatile or non-volatile memory components. In certain embodiments, a sensor component is configured to acquire the one or more drug characteristics that are stored in the memory component on the drug reservoir. In some embodiments, a drug reservoir comprises a near-field communication (NFC) component and/or a radio frequency identification (RFID) component that are configured for data exchange.

Drug Delivery Cannula

Aspects of the disclosure include a drug delivery cannula that is configured to be inserted into a patient's body to deliver a medication. In some embodiments, a drug delivery cannula can comprise a rigid or semi-rigid needle. In some embodiments, a drug delivery cannula can comprise a catheter. Drug delivery cannulas in accordance with embodiments of the disclosure can be integrated with one or more components of the subject systems and devices, or can be separate components that are configured to be operably connected to a subject system or device for purposes of delivering a medication to a patient. In some embodiments, a drug delivery cannula can be configured for implantation into a patient, wherein at least a portion of the drug delivery cannula is configured or adapted to remain implanted in the patient (e.g., to remain placed in an artery or vein of a patient, or to remain placed under a patient's skin) for an extended period of time.

In certain embodiments, a drug delivery cannula can comprise one or more insertion components that are configured to introduce the drug delivery cannula into a desired position (e.g., into an artery or vein of a patient, or under a patient's skin, i.e., for subcutaneous delivery) in order to carry out delivery of a medication. In some embodiments, an insertion component is configured to be removed before a medication is delivered to the patient, whereas in some embodiments, an insertion component is configured to remain in place while a medication is delivered to the patient. A non-limiting example of an insertion component is a catheter needle, which is configured to introduce a catheter into a patient's vein, and to be removed following placement of the catheter, leaving the catheter positioned in the vein, or in a subcutaneous position.

In some embodiments, a subject drug delivery system or device comprises a drug delivery cannula shield (e.g., a needle shield) that is configured to protect a user from accidentally coming into contact with the drug delivery cannula. Drug delivery cannula shields in accordance with embodiments of the disclosure comprise an open proximal end, a closed distal end, and a tubular body having a length that is at least slightly longer than the drug delivery cannula prior to its deployment. In use, the drug delivery cannula shield is configured to be placed over the drug delivery cannula so that the open distal end mechanically interacts with one or more components of the drug delivery system or device (e.g., a distal end of a syringe barrel) to keep the drug delivery cannula shield in place until it is removed by a user. In certain embodiments, a drug delivery cannula shield is retractable, and is configured to retract when the shield is placed against a user's skin and pressure is applied. In some embodiments, after the drug has been delivered to the patient and pressure is removed from the system or device, the drug delivery cannula shield is configured to move back into position to protect the user from accidental contact with the drug delivery cannula. In some embodiments, a drug delivery cannula shield can comprise a spring mechanism that is configured to allow the shield to retract when pressure is applied, and to return to a protective position when pressure is removed.

Needle Safety Device (NSD)

Aspects of the disclosure include a needle safety device (NSD) that is configured or adapted to sequester the drug delivery cannula after it has been withdrawn from the patient. NSDs in accordance with embodiments of the disclosure include a housing component that is appropriately sized to sequester a drug delivery cannula. In some embodiments, an NSD is configured to be mechanically activated when the actuator component completes a delivery stroke. For example, in some embodiments, an NSD comprises one or more trigger elements that are triggered when the actuation component completes a delivery stroke. In some embodiments, an NSD comprises a trigger element that is triggered when one or more elements of the actuation component makes contact with the trigger element, thereby configuring the NSD to be triggered when the actuation component contacts the trigger element. In certain embodiments, an actuation component comprises a contact switch with a predetermined force value required to activate the contact switch, and an NSD comprises a trigger element with a triggering force requirement that is higher than the predetermined force required to activate the contact switch. As such, a mechanical force that activates the NSD will necessarily activate the contact switch. In some embodiments, an NSD is activated simultaneously with detection of a delivery signature by the sensor component. In some embodiments, an NSD is activated simultaneously with transmission of a report comprising a drug dose completion signal from the sensor component to the data management component.

In some embodiments, an NSD is configured to be electrically activated by a sensor component. For example, in some embodiments, when a sensor component detects a delivery signature at the completion of a delivery stroke, the sensor component sends an electronic activation signal to the NSD, causing the NSD to activate and sequester the drug delivery cannula.

In some embodiments, when the NSD is activated, the NSD changes position so that the drug delivery cannula is completely surrounded by (or sequestered within) the NSD component. In some embodiments, an NSD is configured to move over a drug delivery cannula. In some embodiments, a drug delivery cannula is configured to move within an NSD. In some embodiments, an NSD is configured to lock into place to sequester the drug delivery cannula inside the NSD when the NSD is activated. In some embodiments, an NSD is configured to withdraw a drug delivery cannula into a syringe, with no external housing, to sequester the drug delivery cannula. Such approaches prevent a user from accidentally coming into contact with drug delivery cannula after it has been used.

Turning now to FIG. 24, a drug delivery system comprising an NSD is depicted. In the depicted embodiment, the NSD is in an activated state, and is extended over the drug delivery cannula to sequester the drug delivery cannula. In FIG. 25, the same drug delivery system is depicted prior to activation of the NSD. As depicted, the drug delivery system in FIG. 25 comprises a drug delivery cannula that has not yet been sequestered within the NSD. Further depicted in FIG. 25 is an NSD triggering element that is configured to trigger the NSD when the syringe stopper rod mechanically interacts the NSD triggering element.

Finger Flange Component

Aspects of the disclosure include a finger flange component that is configured or adapted to be coupled to a subject system or device (e.g., configured to be coupled to a housing of a subject device, or to be coupled to a syringe barrel of a subject device). Finger flange components in accordance with embodiments of the disclosure comprise lateral surfaces that increase the surface area available for a user's fingers to grasp a subject device. The additional surface area makes it easier for a user to grip and control the device during administration of the drug.

In some embodiments, a finger flange component is configured to be removably coupled to a subject system or device. For example, in some embodiments, a finger flange component is configured to be press fitted onto a housing, or onto a drug reservoir (e.g., onto a pre-filled syringe) and can comprise one or more mechanical components (e.g., snap components) that can mate with one or more complementary components on, e.g., a housing or a drug reservoir, in order to ensure a secure connection. In some embodiments, a finger flange component can be integrated with a needle safety device (NSD) as described above. In some embodiments, a sensor component is configured to fit within a finger flange component. In certain embodiments, a sensor component comprises two or more individual units, and each unit is configured to fit on one side of a finger flange component, so that a first unit of the sensor component is located on a first side of a finger flange component, and a second unit of the sensor component is located on a second side of the finger flange component. FIG. 23 depicts a drug delivery system comprising a finger flange component.

Data Management Component

Aspects of the disclosure include a data management component that is configured or adapted to communicate with the subject systems or devices and/or a user, e.g., to receive a report comprising a drug dose completion signal from a subject system or device, to send one or more commands to a subject system or device, or to send a reminder to a user that a drug dose is due to be administered at a certain time. In some embodiments, a data management component comprises a computer (e.g., a personal computer, a networked computer or a network server). In some embodiments, a data management device comprises a mobile computing device (e.g., a smart phone, or a laptop computer). In some embodiments, a data management component is an Internet-enabled device that is capable of sending and receiving information over the Internet. In some embodiments, a data management component comprises an application that is configured to manage one or more aspects relating to administration of a drug to a user (e.g., to record administration of individual drug doses to a patient, to remind a patient regarding upcoming drug dose administrations, to validate one or more drug identification characteristics by interacting with a remote database, etc.). In some embodiments, a data management component is configured to indicate to a user that one or more communication components are operational and/or are connected to one or more additional components of the subject drug delivery systems or devices. For example, in some embodiments, a data management component is configured to indicate to a user that the data management component is connected (e.g., via a Bluetooth or WiFi connection) to a subject drug delivery system or device. In some embodiments, one or more indicator components on a subject drug delivery system or device, as described above, can further be used to indicate to a user that the data management component is connected to the system or device. Any suitable combination of indicator components on the data management component and/or the other components of the system or device can be used to indicate a connection status of the data management component to a user (e.g., connected, attempting to connect, not connected, disconnected, etc.).

In some embodiments, a data management component is configured or adapted to receive a report from a subject drug delivery system or device, and to record one or more aspects of the report for purposes of maintaining a patient's medical record/history. For example, in some embodiments, a data management component is configured to receive a report from a system or device that indicates a drug dose was administered to the patient, and the data management component records administration of the drug dose, including the date and time at which the drug dose was delivered. In some embodiments, a report can contain additional information relating to, e.g., the drug that was administered or the patient that received the drug. In some embodiments, a report can contain information relating to one or more operational states of the subject systems or devices. For example, in some embodiments, a report comprises information relating to, e.g., the temperature or temperature history of a system or device. In some embodiments, a report comprises information relating to a geographical location of the drug delivery system at the time of administration. In some embodiments, a report comprises information relating to an anatomical location on a patient's body (e.g., the patient's right arm, or the patient's left leg) where the dose was delivered. In some embodiments, a report comprises information relating to a force profile that was used to administer the drug dose to the patient.

In some embodiments, a data management component is configured or adapted to receive one or more data inputs from a subject system or device, and to validate the one or more data inputs prior to proceeding with administration of the drug to the patient. For example, in some embodiments, a data management component is configured to receive a drug identification characteristic from a subject system or device (e.g., from a drug reservoir that has been coupled to the system or device), and to verify that the drug identification characteristic is valid before proceeding with administration of the drug to the patient. In some embodiments, a data management component is configured to transmit one or more drug identification characteristics over the Internet to a remote database, and to receive an authentication signal in response, prior to administering the drug to the patient.

In some embodiments, a data management component is configured or adapted to receive one or more data inputs from a subject system of device, and to analyze the received data to determine whether a delivery stroke has been completed. For example, in some embodiments, a subject system or device is configured or adapted to transmit data from a deflection component and/or a sensor to a data management component, and to analyze the received data and compare the received data to one or more stored delivery signature parameters (e.g., a reference delivery signature) to determine whether the received data corresponds to a delivery signature for the device.

In some embodiments, a data management component is configured or adapted to determine whether a specific drug delivery system or device, or a component thereof (e.g., a drug reservoir) is the result of an authorized sale from a manufacturer, and/or an authorized prescription of the drug from a prescribing health care provider (e.g., from a prescribing physician), in a specific geographical location (e.g., in a specific country). For example, in some embodiments, a data management component is configured to receive one or more drug identification characteristics from a subject drug delivery system or device (or a component thereof, e.g., a drug reservoir), and to transmit the one or more drug identification characteristics to a remote database. In some embodiments, a data management component is further configured or adapted to transmit a geographical location of the drug delivery system or device to the remote database as well. In some embodiments, a remote database is configured or adapted to compare the one or more drug identification characteristics with the geographical location received from the data management component to determine whether a specific drug delivery system or device, or component thereof (e.g., a drug reservoir), is being used in the geographical location (e.g., the specific country) where it was sold.

In some embodiments, a data management component is configured to validate one or more operational states of the subject systems or devices prior to administration of the drug to the patient. For example, in one embodiment, a data management component is configured to determine whether a drug reservoir is at a temperature that falls within a predetermined acceptable temperature range prior to administering the drug to the patient. In some embodiments, a data management component is configured to verify that a subject system or device is in a "ready" operational state prior to administering the drug to the patient.

Data management components in accordance with embodiments of the disclosure are configured to determine a date and time at which a drug is administered to a patient (e.g., a time stamp for the drug dose administration). In some embodiments, a data management component is configured to receive a drug dose completion signal from a subject system or device, and is configured to determine the exact time of the drug administration based on additional information transmitted from the system or device. For example, in some situations, a subject system or device may not be operatively connected to a data management component at the specific date and time at which administration of the drug was carried out. In such instances, a subject system or device is configured to determine an elapsed time since completion of the drug administration procedure. When the system or device becomes connected to the data management component, a drug dose delivery signal as well as the elapsed time since the administration is transmitted to the data management component. The data management component then utilizes the transmitted information to back-calculate the specific date and time at which the drug administration procedure was completed, and records this information in the patient's records.

Controller, Processor, and Computer-Readable Media

In some embodiments, a subject system or device can comprise a controller, a processor, and a computer readable medium that are configured or adapted to control or operate one or more components of the subject systems or devices. In some embodiments, a system or device includes a controller that is in communication with one or more components of the subject systems of devices, and is configured to control aspects of the systems or devices and/or execute one or more operations or functions of the subject systems or devices. In some embodiments, a system or device includes a processor and a computer-readable medium, which can include memory media and/or storage media. Applications and/or operating systems embodied as computer-readable instructions on the computer-readable memory can be executed by the processor to provide some or all of the functionalities described herein.

In some embodiments, a subject system or device includes a user interface, such as a graphical user interface (GUI), that is configured or adapted to receive an input from a user, and to execute one or more of the methods as described further herein. In some embodiments, a GUI is configured to display data or information to a user.

Energy Harvesting

Aspects of the disclosure include energy harvesting systems. Such systems may be coupled to a drug delivery device, such as the "smart" prefilled syringe devices disclosed herein. The use of an energy harvesting system allows the drug delivery device to harvest energy from its surrounding to power on-board communication electronics. This reduces or eliminates the need for a battery located on the device. In turn, this reduces challenges associated with environmentally-friendly disposal of the devices, which are often single-use and disposable type devices. In some embodiments, mechanical energy is stored in a spring or similar means and this energy is recaptured at the time of use, such as at the end-of-dose (EOD). In some embodiments, the spring or other storage mechanism supplies a generator with mechanical energy that is converted to electrical energy, rectified and regulated to power a wireless transmission from the pre-filled syringe to a mobile device or home based receiver or hub. As previously described, this wireless transmission can provide drug delivery dose completed confirmation via smart device technology.

Various connection methods may be employed to wirelessly connect the self-powered drug delivery device to a user's smartphone. These may be segmented into direct and indirect methods:

Direct Methods—Communication Requiring No External Peripherals
    BLE—Master/slave
    BLE—Non-connectable connection (Advertising)
    BLE—Scan response
    WiFi
    NFC (Near-field communication)
    Cellular (existing logistics)
    Audio (utilizing ultrasound identifiers)

Indirect Methods—Communication Requiring External Peripherals/Infrastructure
    Internet (web-hosted)
    'Home hub'—RF (local)
    'Home hub'—Backscatter
    'Remote hub'—LORAWAN, SIGFOX, Narrowband Internet of Things (IoT)

In some embodiments of energy harvesting, BLE (Bluetooth Low Energy) "non-connectable" may be chosen due to it being a widespread and mature technology. With this approach, a connection does not need to be initiated between the device and phone, thereby reducing power consumption. In some embodiments, at least 1.04 mJ is required to be delivered to a BLE module to perform the types of communications described herein. Because of energy losses between a power generating device and a BLE module, in some embodiments it is desirable to have a generator output of approximately 10 mJ.

Figure 31:
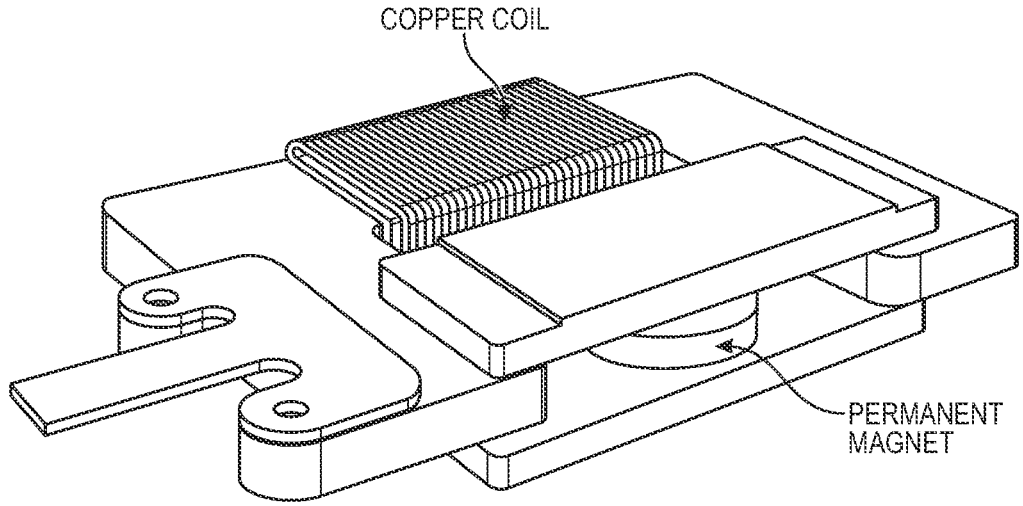
FIG. 31 is a three dimensional rendering of an impulse energy harvester according to one embodiment of the disclosure with its lever in a raised position.
Figure 32:
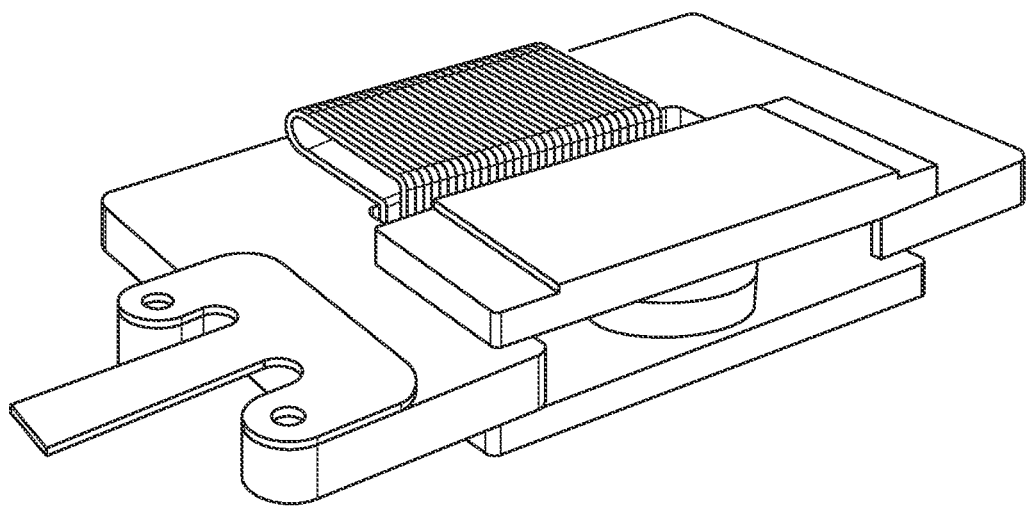
FIG. 32 is a three dimensional rendering of the impulse energy harvester of FIG. 31 with its lever in a lowered position.

According to aspects of the disclosure, the energy harvesting source may comprise:
    Ambient radiation
    Fluid flow
    Photovoltaic
    Piezoelectric
    Pyroelectric
    Thermoelectric
    Electrostatic
    Magnetic inductive
    Chemical In the magnetic inductive category, the energy harvesting source may be of one of the following design configurations:
    Impulse Energy Harvester
    Levitating Magnetic Harvester Cantilever Beam Harvester
Axial Flux Generator
Claw-Pole Microgenerator Referring now to FIGS. 31 and 32, an exemplary embodiment of an impulse energy harvester is provided. It is to be understood that this embodiment demonstrates the principles of the impulse energy harvesting technology but may be further optimized for use with a syringe barrel and/or stopper rod. In this exemplary device, the magnetic flux of a permanent magnet is routed through an iron core, around which a copper coil is wound. Depressing a lever flips the polarity of the field, generating a current pulse by electromagnetic induction. FIG. 31 shows the device with its lever in a raised position and FIG. 32 shows the device with the lever in a lowered position.

Figure 33:
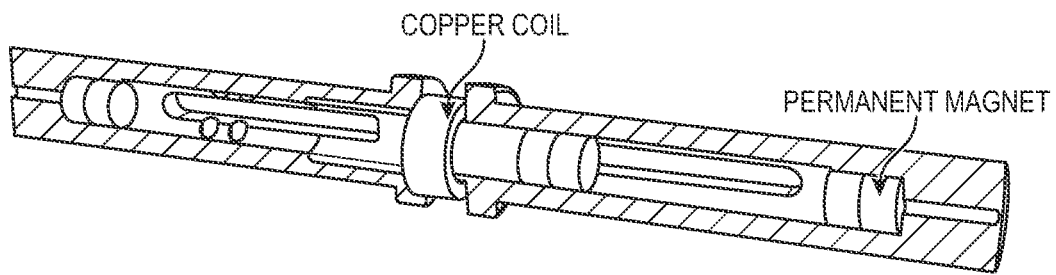
FIG. 33 is a three dimensional rendering of a levitating magnetic harvester according to one embodiment of the disclosure.

Referring now to FIG. 33, an exemplary embodiment of a levitating magnetic harvester is provided. It is to be understood that this embodiment demonstrates the principles of the levitating magnetic harvester technology but may be further optimized for use with a syringe barrel and/or stopper rod. In this exemplary device, a permanent magnet slides within a stationary coil, inducing current flow as the field moves. Released from a displaced position on drug delivery, the magnet would oscillate back and forth to produce an alternating current. Either compression springs or repelling magnets (shown) would return the magnet at the positional extremes.

Figure 34:
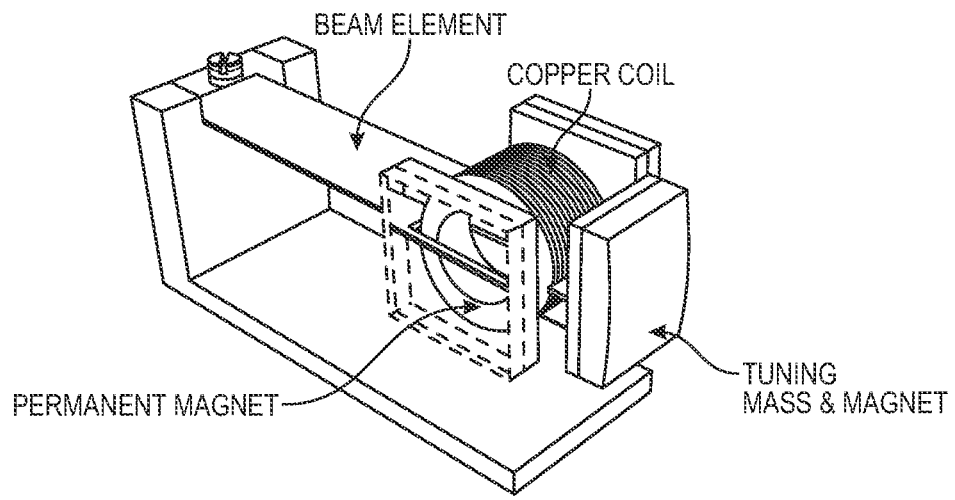
FIG. 34 is a three dimensional rendering of a cantilever beam harvester according to one embodiment of the disclosure.

Referring now to FIG. 34, an exemplary embodiment of a cantilever beam harvester is provided. It is to be understood that this embodiment demonstrates the principles of the cantilever beam harvester technology but may be further optimized for use with a syringe barrel and/or stopper rod. In this exemplary device, two magnets are mounted at the end of a cantilever beam, either side of a static, base-mounted copper coil. When the beam vibrates the magnets oscillate back and forth, inducing a current in the central coil.

Figure 35:
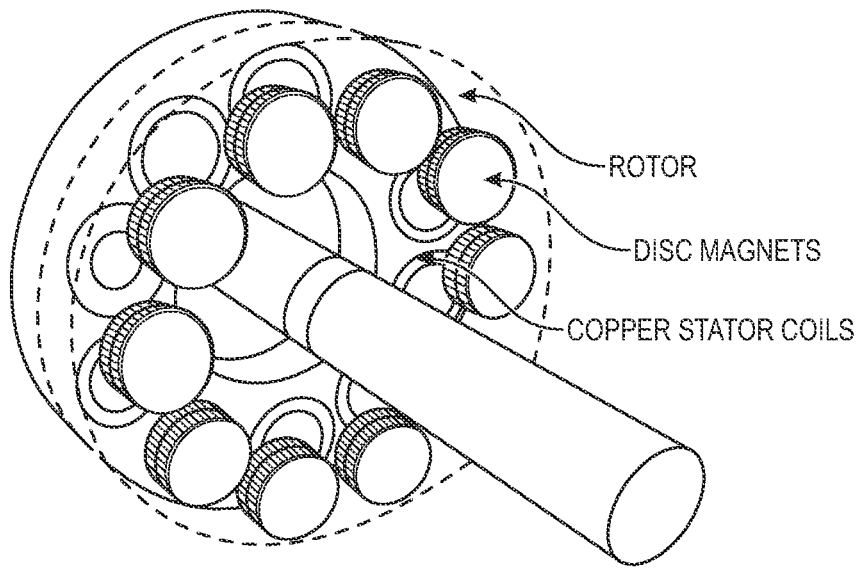
FIG. 35 is a three dimensional rendering of an axial flux generator according to one embodiment of the disclosure.
Figure 36:
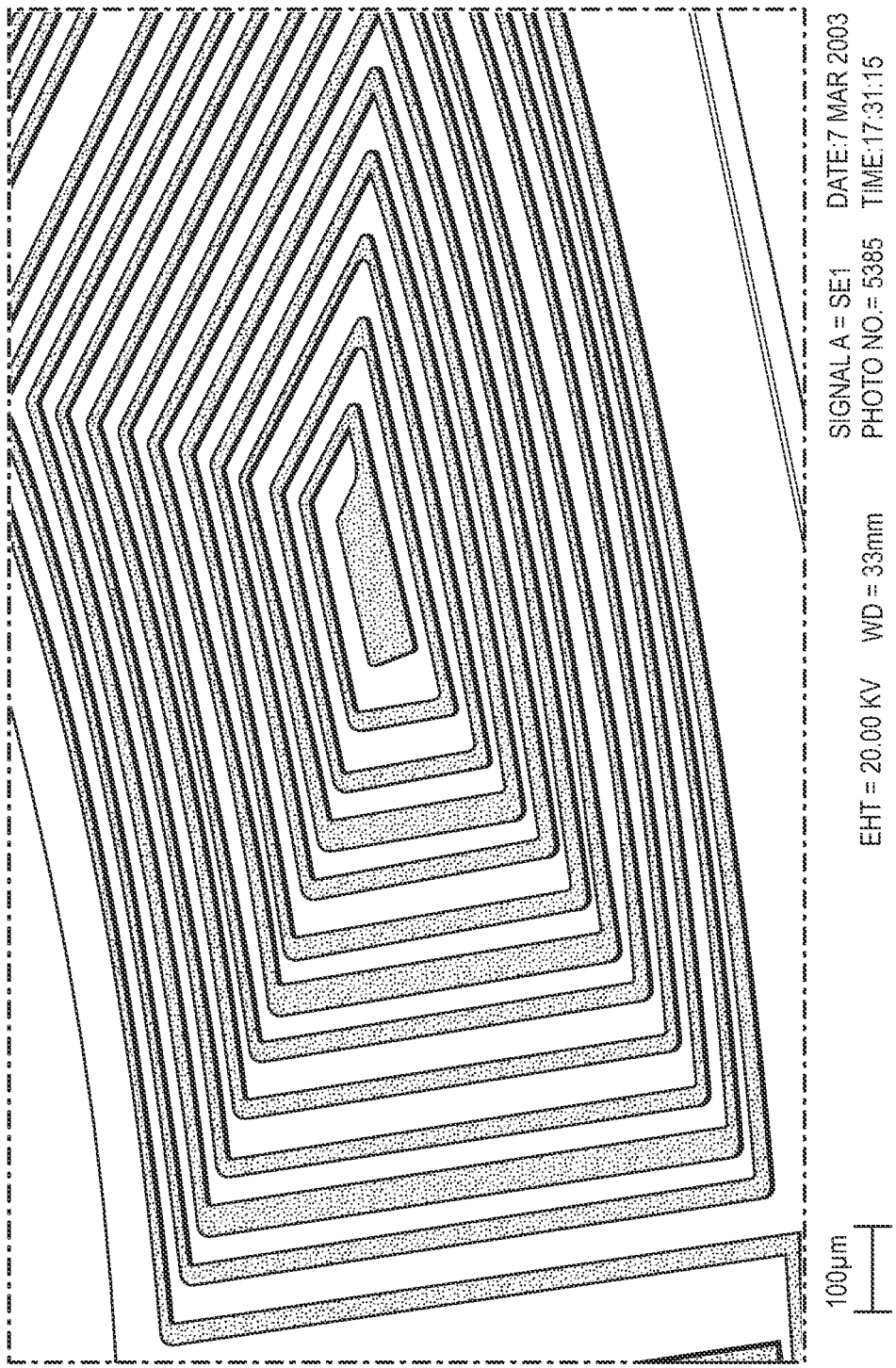
FIG. 36 is a photograph of coils manufactured in multiple layers on a printed circuit board that may be utilized in the axial flux generator shown in FIG. 35.
Figure 37:
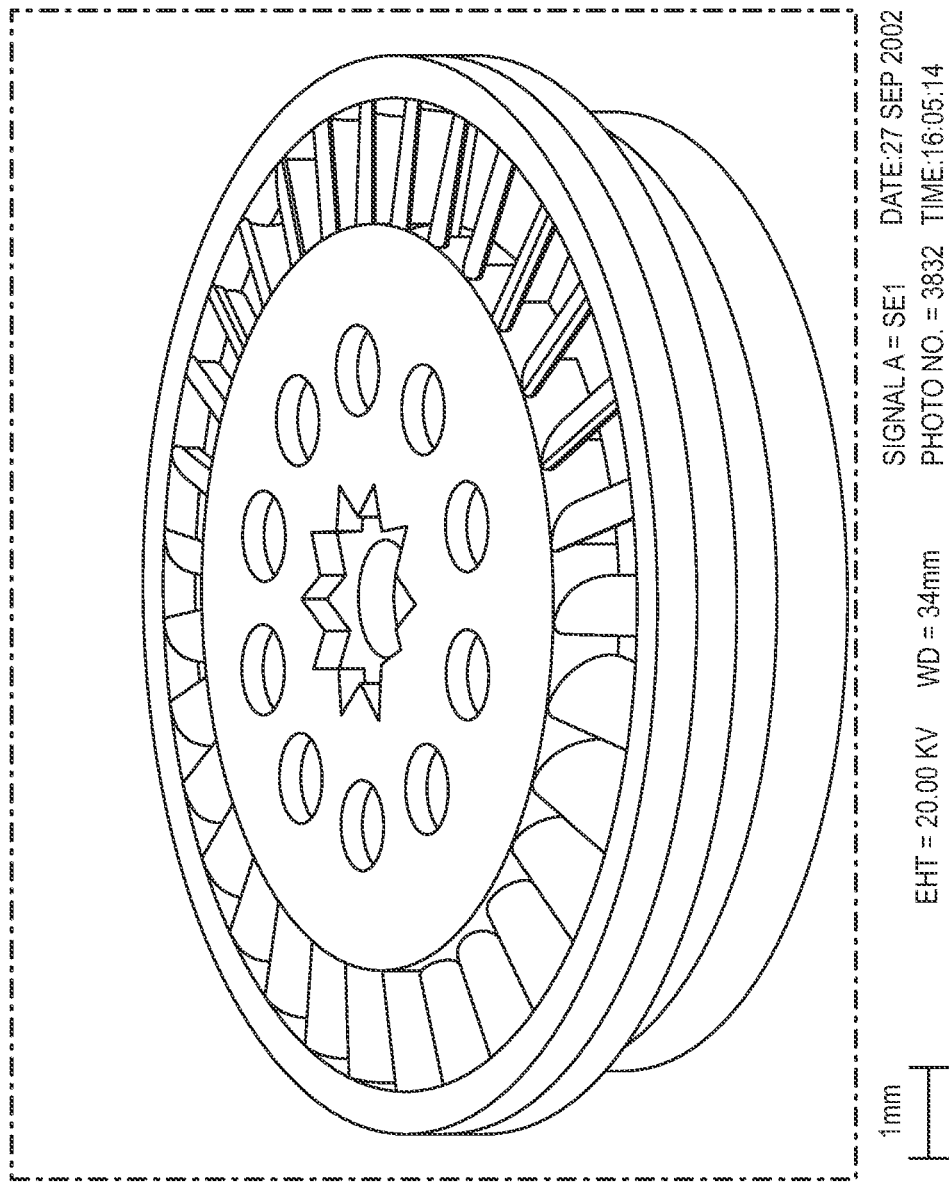
FIG. 37 is a photograph of a rotor having that may be utilized in the axial flux generator shown in FIG. 35.

Referring now to FIGS. 35-37, an exemplary embodiment of an axial flux generator is provided. It is to be understood that this embodiment demonstrates the principles of the axial flux generator technology but may be further optimized for use with a syringe barrel and/or stopper rod. In this exemplary device, a series of magnets around the perimeter of a spinning rotor induce current flow in stator coils. The primary direction of magnetic flux and the coil axes is axial. This arrangement allows for a compact 'pancake' form factor suitable for location within the plunger-rod head. Further details of axial flux devices can be found in Holmes, A., Guodong, H. and Pullen, K. (2005). Axial-Flux Permanent Magnet Machines for Micropower Generation, Journal of Microelectromechanical Systems, 14(1), pp. 54-62, incorporated herein by reference. In research conducted by Holmes et al., stator coils were manufactured in multiple layers on a printed circuit board as shown in FIG. 36, allowing for low manufacture costs. The rotor featured permanent disc magnets as shown in FIG. 37, and the device produced 1.1 mW per stator at 30,000 rpm.

Figure 38:
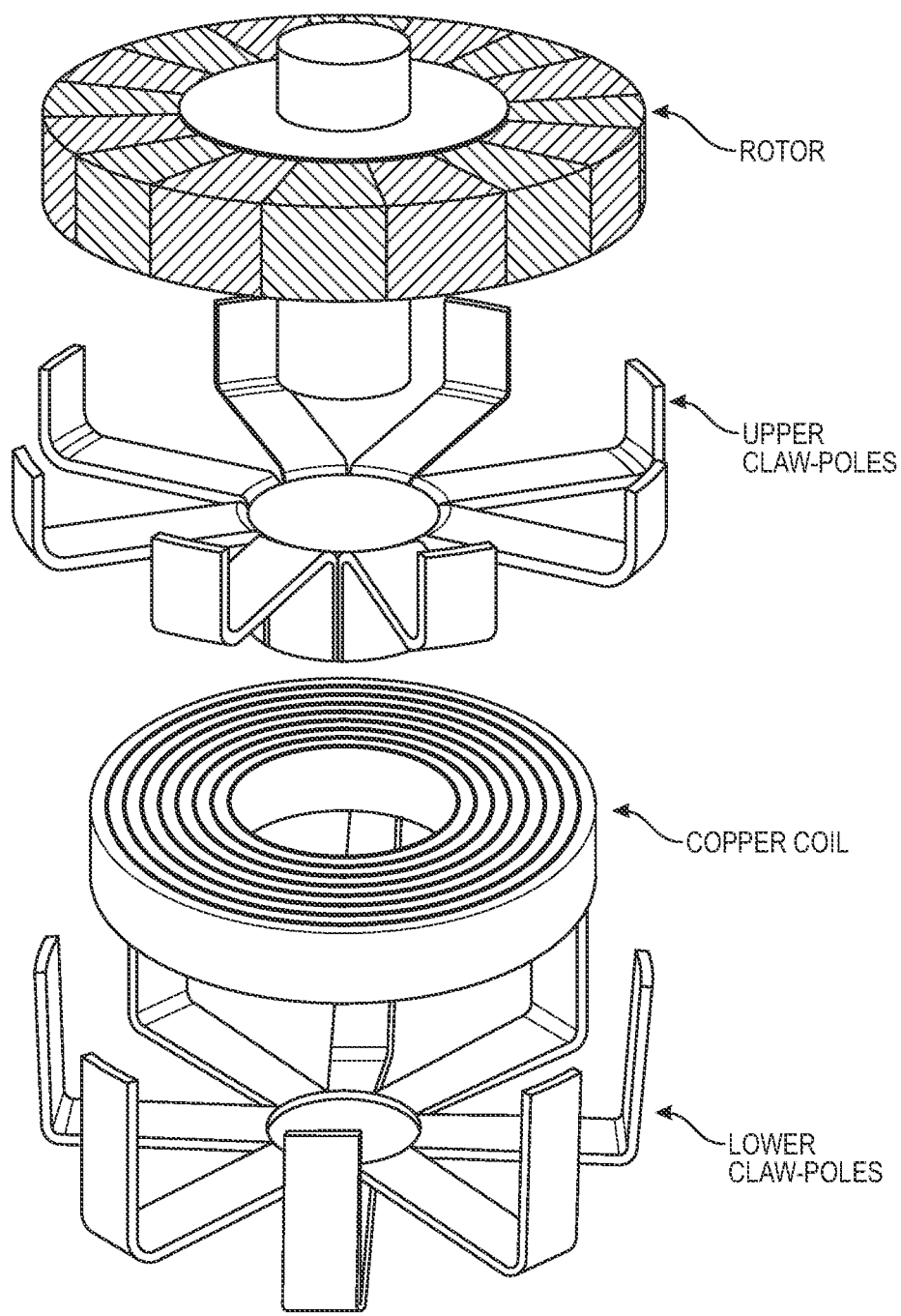
FIG. 38 is a three dimensional exploded view rendering of a claw-pole microgenerator according to one embodiment of the disclosure.

Referring now to FIG. 38, an exemplary embodiment of a claw-pole microgenerator is provided. It is to be understood that this embodiment demonstrates the principles of the claw-pole microgenerator technology but may be further optimized for use with a syringe barrel and/or stopper rod, such as in the embodiments subsequently described herein. In some embodiments, a rotor is divided into segments with alternating magnetic flux direction. Ferrous pole pieces direct the flux in a radial loop around a copper coil. As the rotor turns, magnetic flux switches direction every time a segment moves from one 'claw' to the next.

Various sources of kinetic and/or potential energy may be used to drive the previously described energy harvesting mechanisms. In some embodiments, energy may be provided by the user when depressing the syringe plunger rod. FIG. 27 depicts a typical force that is required to drive a plunger rod through a 22 mm stroke in a 1.0 ml syringe without energy harvesting. The work done (energy used) by the patient can be calculated from the product of force and distance. Making the simplification of a constant 2N applied force throughout the stroke yields the following calculation:

Work done, $E = F \times d = 2N \times 22$ mm $= 44$ mJ

In some embodiments, a minimum increase of 23% is required to harvest the aforementioned 10 mJ target energy to drive the on-board electronics from the plunger rod push force.

Figure 39:
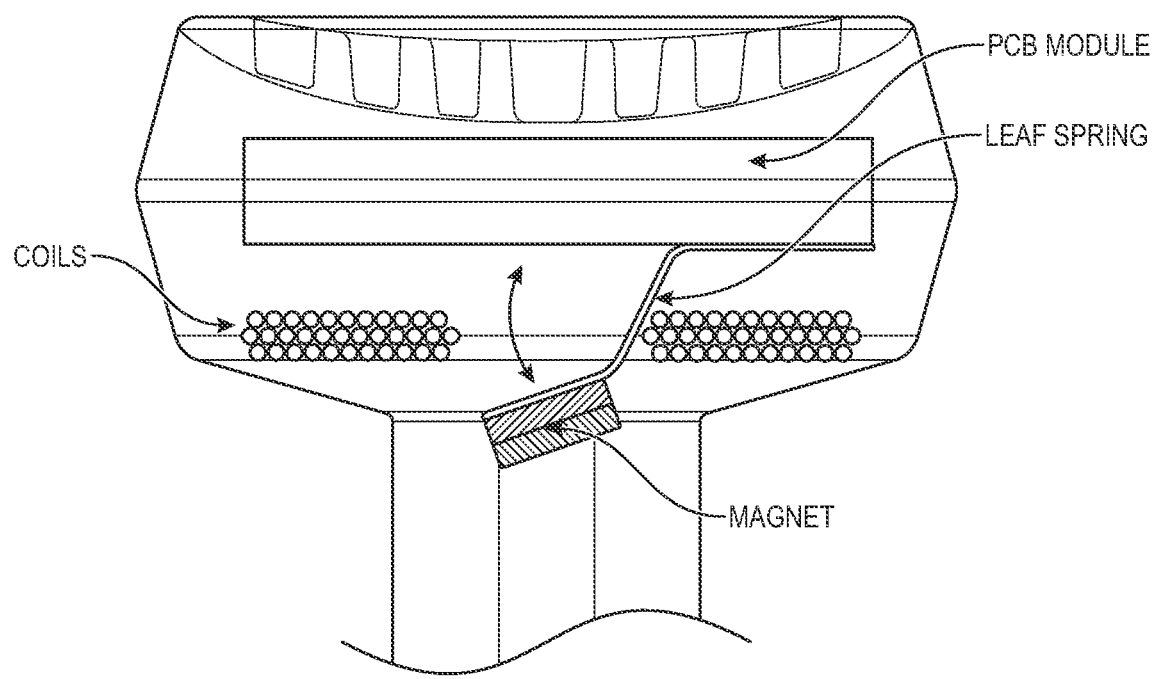
FIG. 39 is a cross-sectional side view depicting an energy harvesting arrangement utilizing a leaf spring according to one embodiment of the disclosure.

Referring to FIG. 39, a leaf spring may be used to store energy that is harvested when the syringe is used. In some embodiments, the leaf spring is located in the head of the plunger rod as shown. A magnet on the leaf spring can be released from a latched position on end of dose. The leaf spring then springs back and forth through a surrounding coil, inducing electrical current flow.

Figure 40:
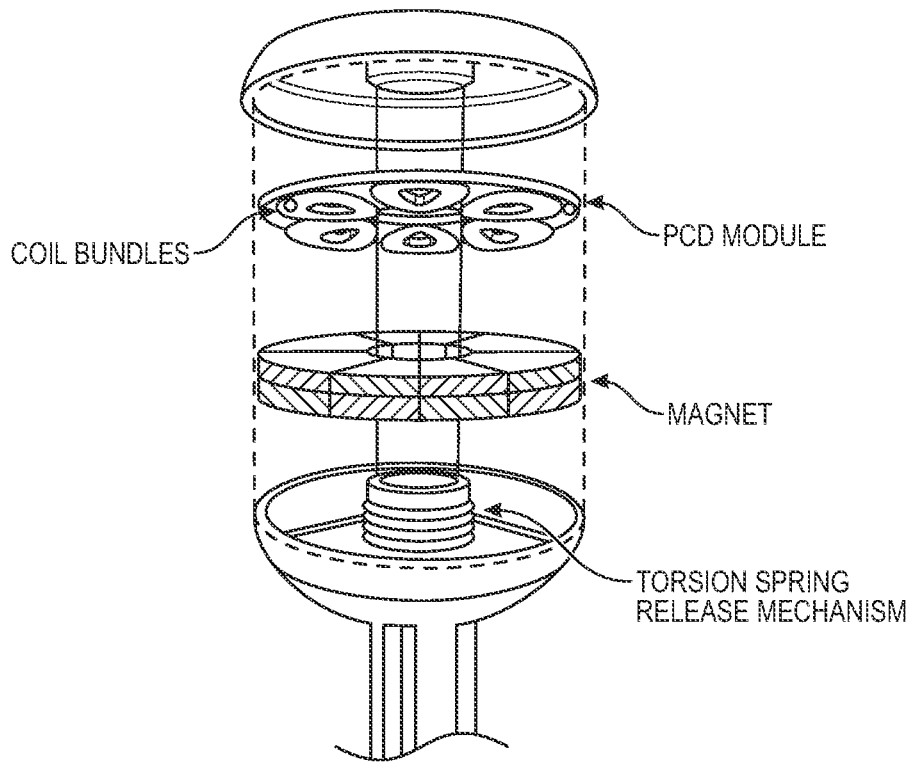
FIG. 40 is a three dimensional exploded view rendering depicting an energy harvesting arrangement utilizing a torsion spring according to one embodiment of the disclosure.

Referring to FIG. 40, a torsion spring may be used to store energy that is harvested when the syringe is used. In some embodiments, the torsion spring is located in the head of the plunger rod as shown. The torsion spring may be preloaded on device assembly and latched in position. At the end of dosing, the spring unlatches, spinning a magnetic rotor which can freewheel. As the rotor spins, electrical current is induced in a rotary generator. In this particular embodiment an axial flux generator type is utilized.

Figure 41:
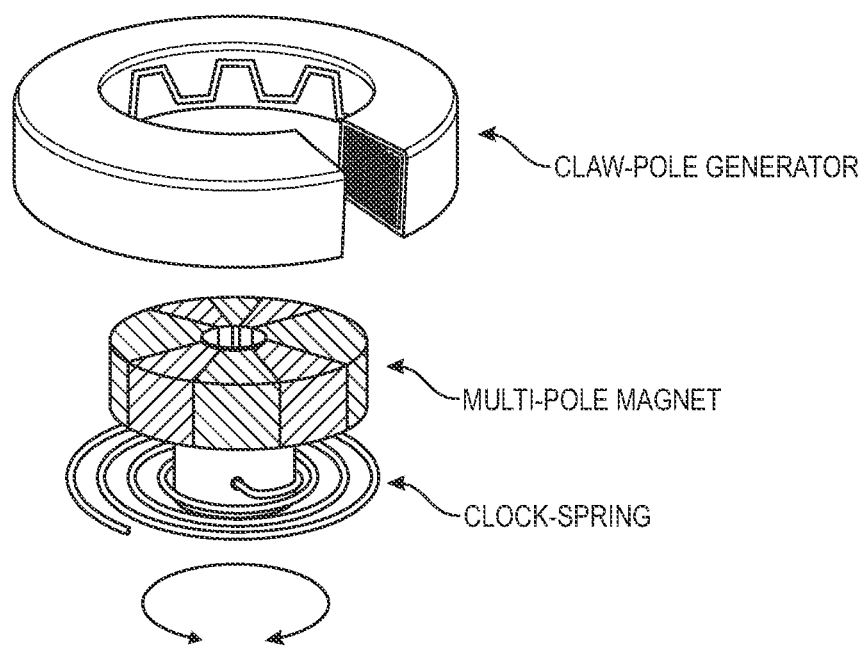
FIG. 41 is a three dimensional exploded view rendering depicting an energy harvesting arrangement utilizing a clock spring according to one embodiment of the disclosure.

Referring to FIG. 41, a clock spring may be used to store energy that is harvested when the syringe is used. In some embodiments, the clock spring is located in the head of the plunger rod as shown. This arrangement enables multiple turns of preload to be placed on the rotor. When the elastic energy is released, the rotor may either freewheel in one direction or oscillate back and forth via its spring connection. In this particular embodiment a claw-pole generator type is utilized.

Naturally, other configurations of springs (not shown) may also be used to store potential energy that is converted into electrical energy during used of the syringe. In torsion and clock springs, stored elastic energy may be proportional to the square of deflection angle. Accordingly, springs with a large deflection angle may be chosen in preference to stiff springs with a small working range. In some embodiments, stored energy varies from 14 mJ to 280 mJ. In some embodiments, peak rotor speeds range from 1,000-30,000 rpm. In other embodiments, peak rotor speeds range from 7,500-16,750 rpm.

Figure 42:
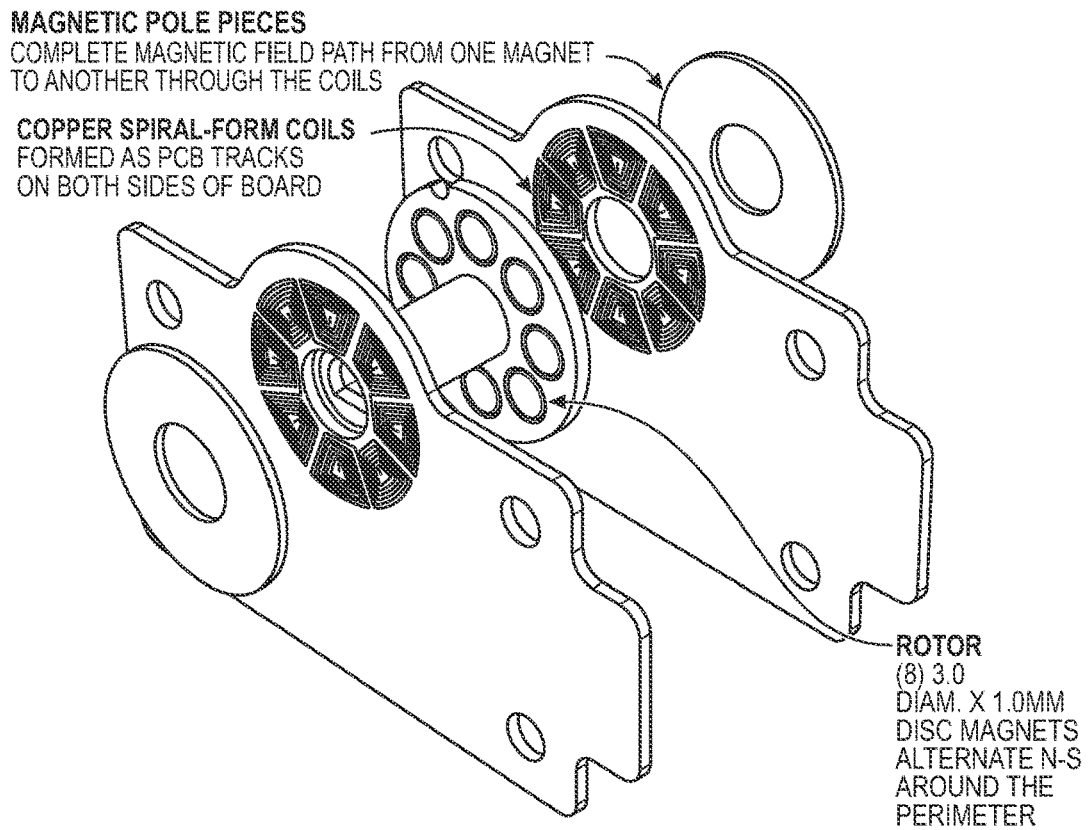
FIG. 42 is a three dimensional exploded view rendering of an axial flux generator according to one embodiment of the disclosure.
Figure 43:
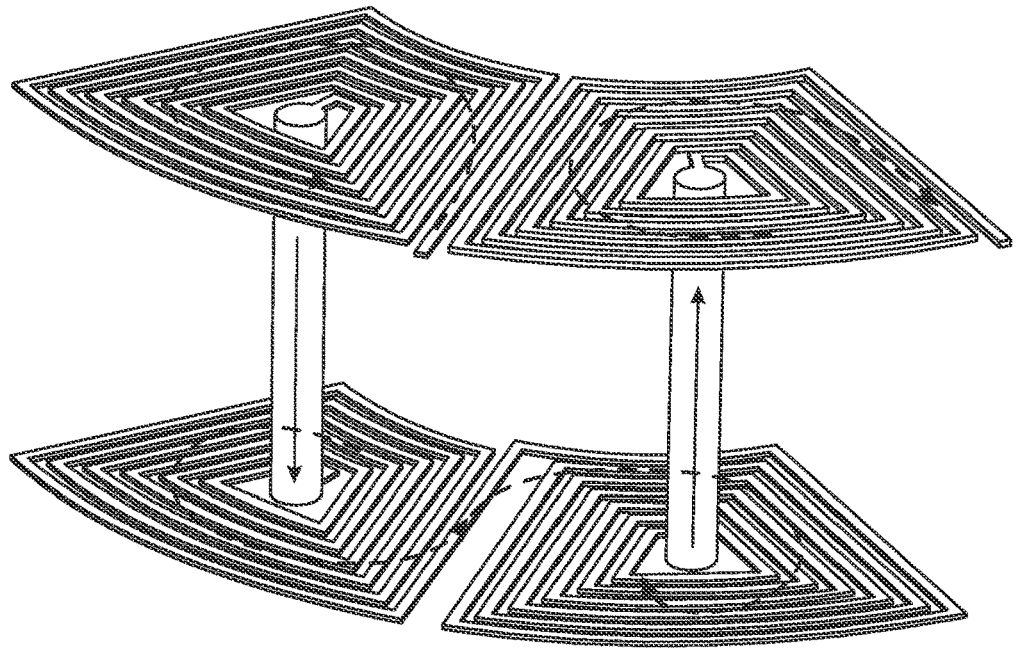
FIG. 43 is a three dimensional rendering of spiral wound coils provided on a PCB of the axial flux generator shown in FIG. 42.

Referring now to FIGS. 42-43, another exemplary embodiment of an axial flux generator is provided. In this embodiment, 8 magnets spin between two coil-loaded printed circuit boards (PCBs), as shown in FIG. 42. Ferrous ring pieces attached to each PCB provide a flux return path. As shown in FIG. 43, the PCB may be provided with spiral wound coils which operate in sets of four, providing a corresponding voltage boost. The dashed lines in FIG. 43 indicate the instantaneous direction of induced current when the rotor is spinning. The coil arrangement shown spans one quadrant of the stator. Four identical sets of these complete the PCB. Each coil set can be combined with the others either in series, providing a voltage boost, or in parallel to boost current. Multilayer PCBs may be used to allow for tens of coils to be stacked one above the other. In some embodiments, the PCB has 96 turns with 6 turns per coil, a track width of 0.125 mm and a gap width of 0.125 mm. Magnets may be bonded in place on the rotor in an alternating North-South configuration. The magnets may be formed from N42 neodymium, have a diameter of 3 mm, a thickness of 1 mm and a pull force of 0.19 kg each. The pole piece may be cut from a ferrous steel sheet of 1 mm thickness. In initial testing, doubling the magnet thickness to 2 mm resulted in an 85% gain in output voltage, with a 1.89 Vp-p output at 2000 rpm.

Figure 44:
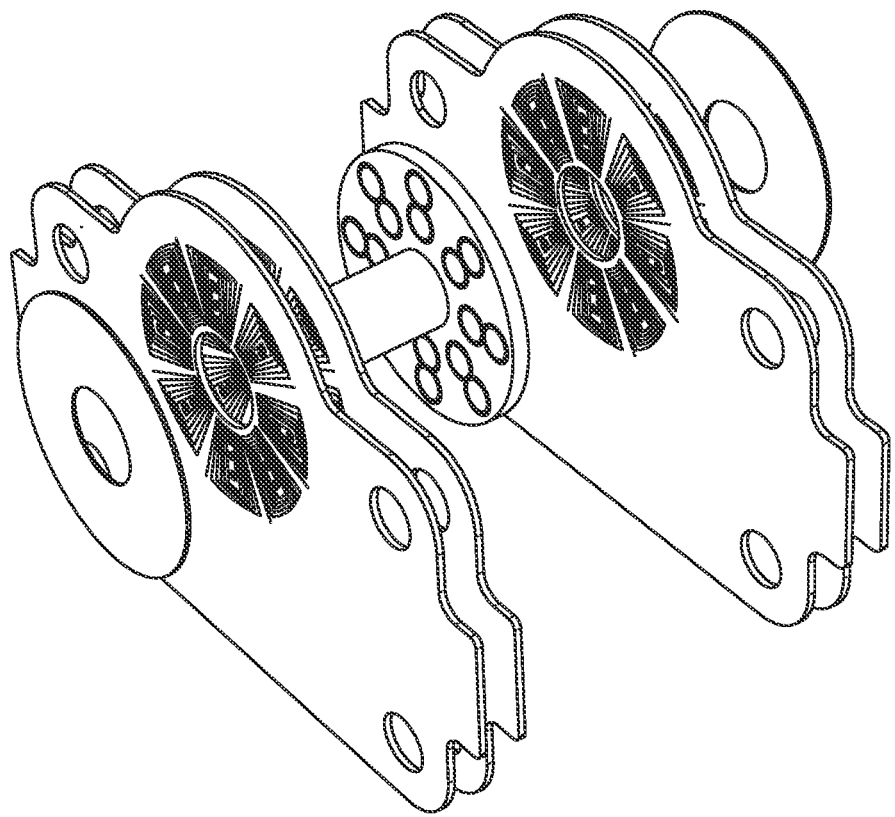
FIG. 44 is a three dimensional exploded view rendering of another axial flux generator according to one embodiment of the disclosure.
Figure 45:
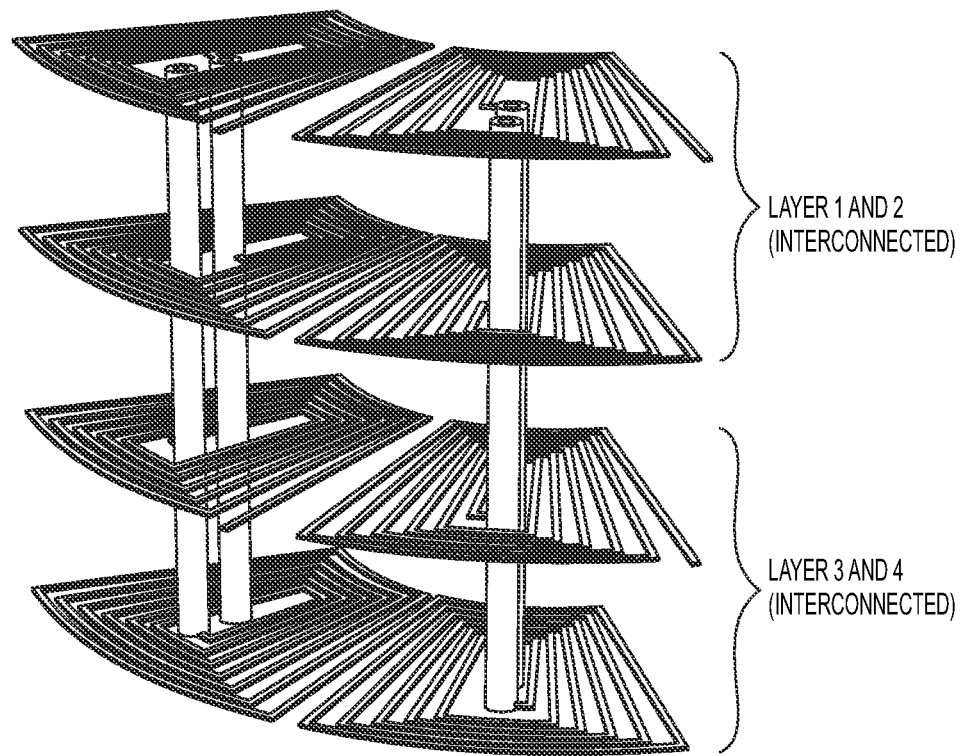
FIG. 45 is a three dimensional rendering of spiral wound coils provided on a PCB of the axial flux generator shown in FIG. 44.

Referring now to FIGS. 44-45, another exemplary embodiment of an axial flux generator is provided. In this embodiment, the use of 8-layer PCB's provides four times the coil number and a corresponding voltage increase compared with the previous embodiment which utilizes 2-layer boards. Alternatively, 4-layer boards with a 0.4 mm sheet thickness may be sandwiched together to give an 8-layer, 0.8 mm format, as shown in FIG. 44. The pole pieces may be manufactured from Arnon 7 electrical steel which reduces losses in the flux return path. Instead of the 8-magnet arrangement of the previous embodiment, the rotor format of this embodiment utilizes 16 magnets each having a diameter of 2 mm and a thickness of 1 mm.

FIG. 45 shows the layout of coils in one quadrant of the PCB over the 4 layers of the board. The upper two layers are isolated from the lower two layers. The current path of the previous embodiment is replicated first across layers 1 and 2, and then again for layers 3 and 4. One through-via connects only layer 1 to layer 2. A second through-via connects only layer 3 to layer 4. In effect, this arrangement provides 8 independent coil sets per PCB. These may then be connected in series to maximize voltage output. In order to accommodate two through-vias and increase the effective (radial) track area, the track and gap width may be reduced to 0.004", or 0.1 mm. In some embodiments, the copper weight is 1 oz, equivalent to a 35 μm thickness.

In initial testing, the power measured of this exemplary embodiment of axial flux generator was 1.80 mJ/s @ 2000 rpm (theoretical). The open circuit voltage was 1.89 Vp-p @2000 rpm. The time to generate 10 mJ @2000 rpm was 5.56 s. Scaling the open-circuit voltage to approximate the output in a spring driven system, where speeds of 15,000 rpm have been observed, suggests 15 Vp-p is achievable. This AC voltage is sufficiently high to rectify efficiently to DC.

Figure 46:
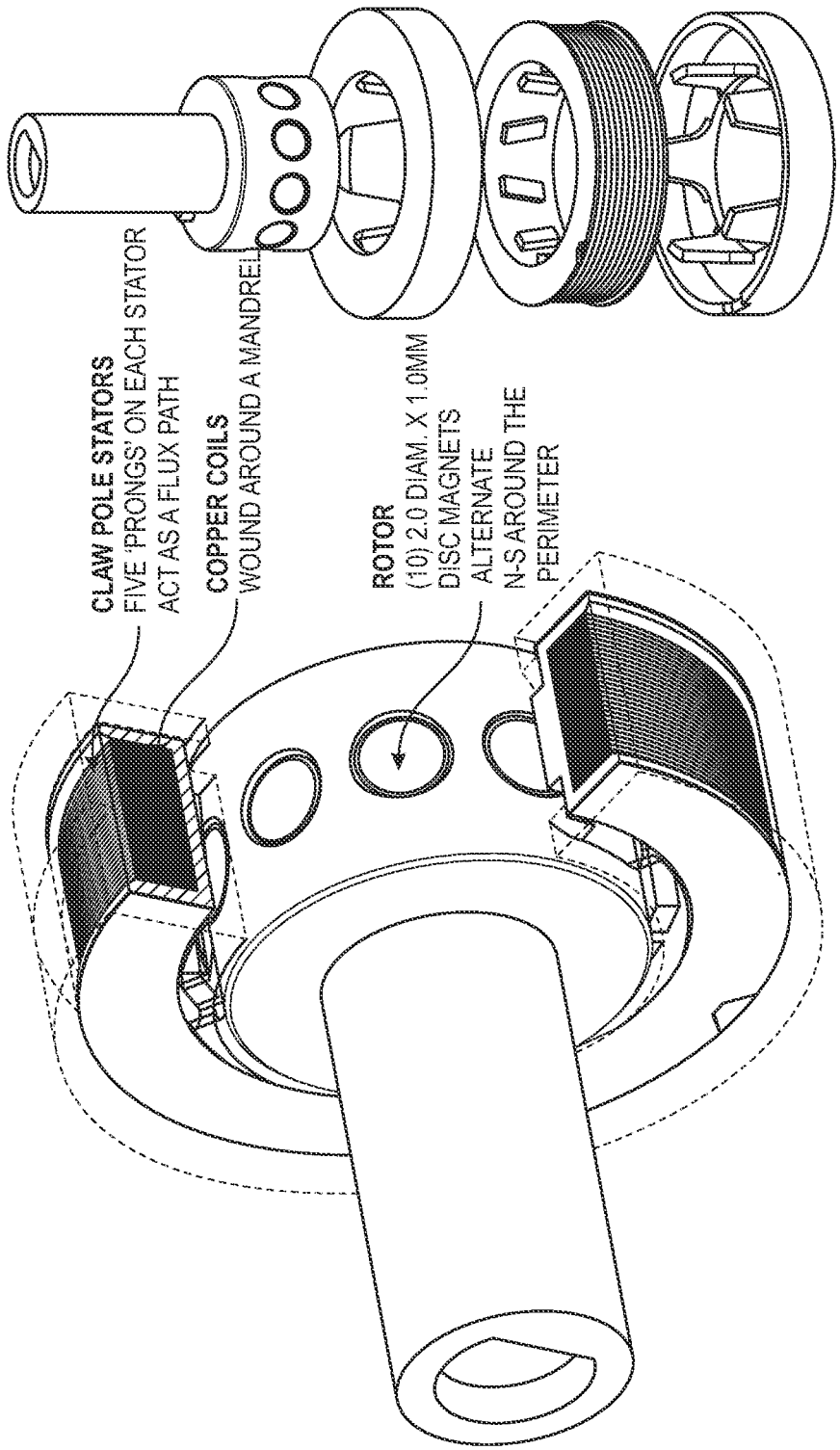
FIG. 46 is a three dimensional rendering of a claw-pole microgenerator according to one embodiment of the disclosure. The left side shows a cut away view and the right side shows an exploded view.

Referring now to FIG. 46, another exemplary embodiment of a claw-pole microgenerator is provided. The left side of FIG. 46 shows a cut-away view of the assembly while the right side shows an exploded view. In this embodiment, 10 permanent magnets are located around the perimeter of the rotor and a wire coil is located on the stator surrounding the rotor. Two claw-pole stator pieces are sandwiched on either side of the coil. When the rotor spins within the annular assembly, an alternating current is induced in the coil. Five prongs on each stator act as a flux path. The outer diameter of the assembly is 16.2 mm, the stator depth is 5.5 mm, the stator wall thickness is 0.6 mm, and the magnet PCD is 9 mm. The 10 rotor magnets are each 2.0 mm in diameter, are 1.0 mm thick, and alternate N—S around the rotor.

Figure 47:
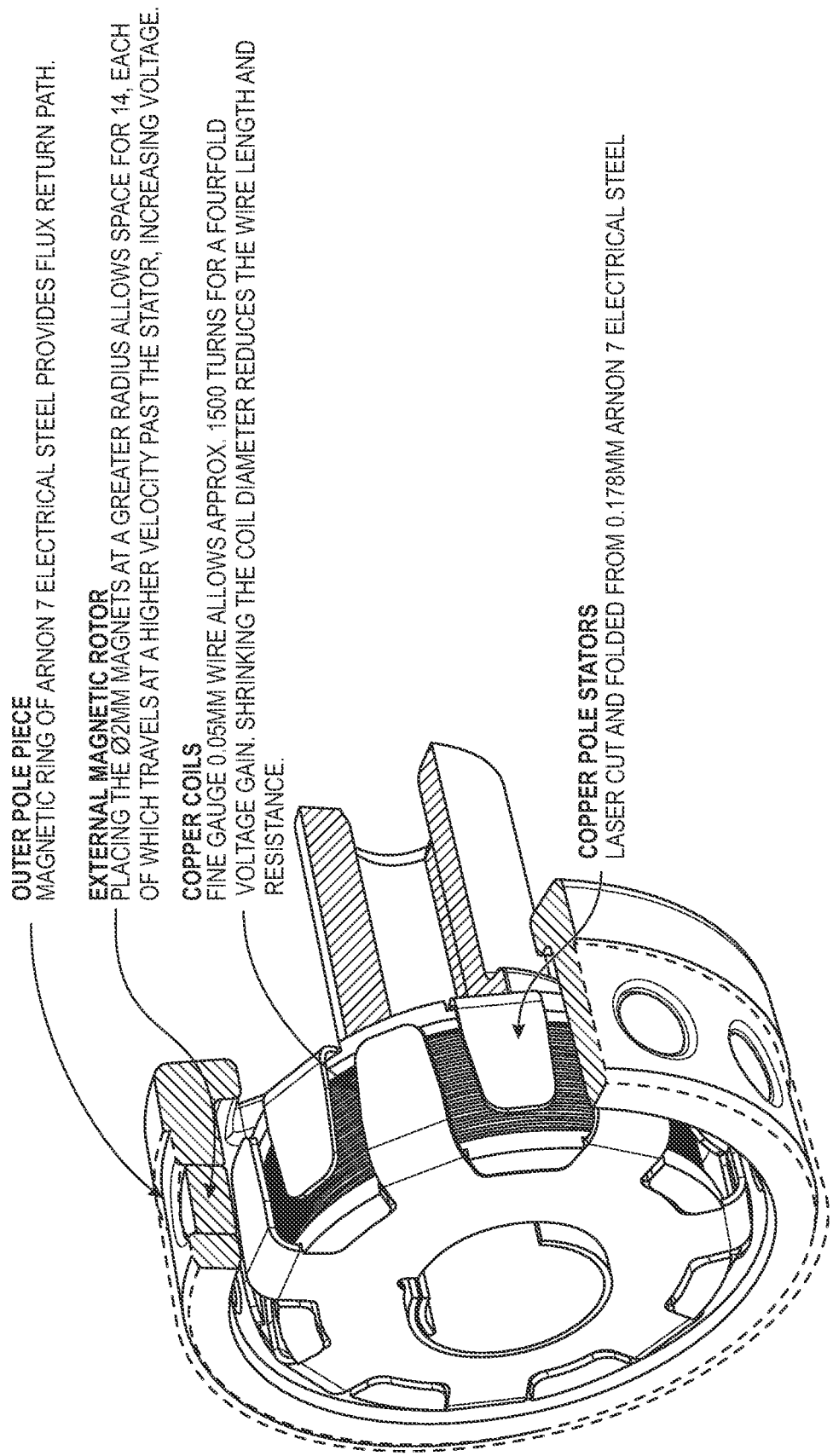
FIG. 47 is a three dimensional rendering of another claw-pole microgenerator according to one embodiment of the disclosure.

Referring now to FIG. 47, another exemplary embodiment of a claw-pole microgenerator is provided. In this embodiment, the wire coil stator is located radially inward from the annular rotor which holds the magnets and spins around the outer periphery of the stator. Placing the ⌀2 mm magnets at a greater radius allows space for 14 magnets, each of which travels at a higher velocity past the stator, thereby increasing voltage. An outer pole piece may be a magnetic ring of Arnon 7 electrical steel to provide a flux return path. Finer gauge 0.05 mm wire allows approximately 1500 turns for a fourfold voltage gain over the previous embodiment. Shrinking the coil diameter reduces the wire length and resistance. Claw pole stators may be laser cut and folded from 0.178 mm Arnon 7 electrical steel for optimal performance. In this exemplary embodiment, the outer diameter of the assembly is 16 mm, the stator depth is 4.35 mm, the stator wall thickness is 0.178 mm, and the magnet PCD is 13.2 mm. At 2000 rpm, this arrangement produces 16.6V.

Figure 49:
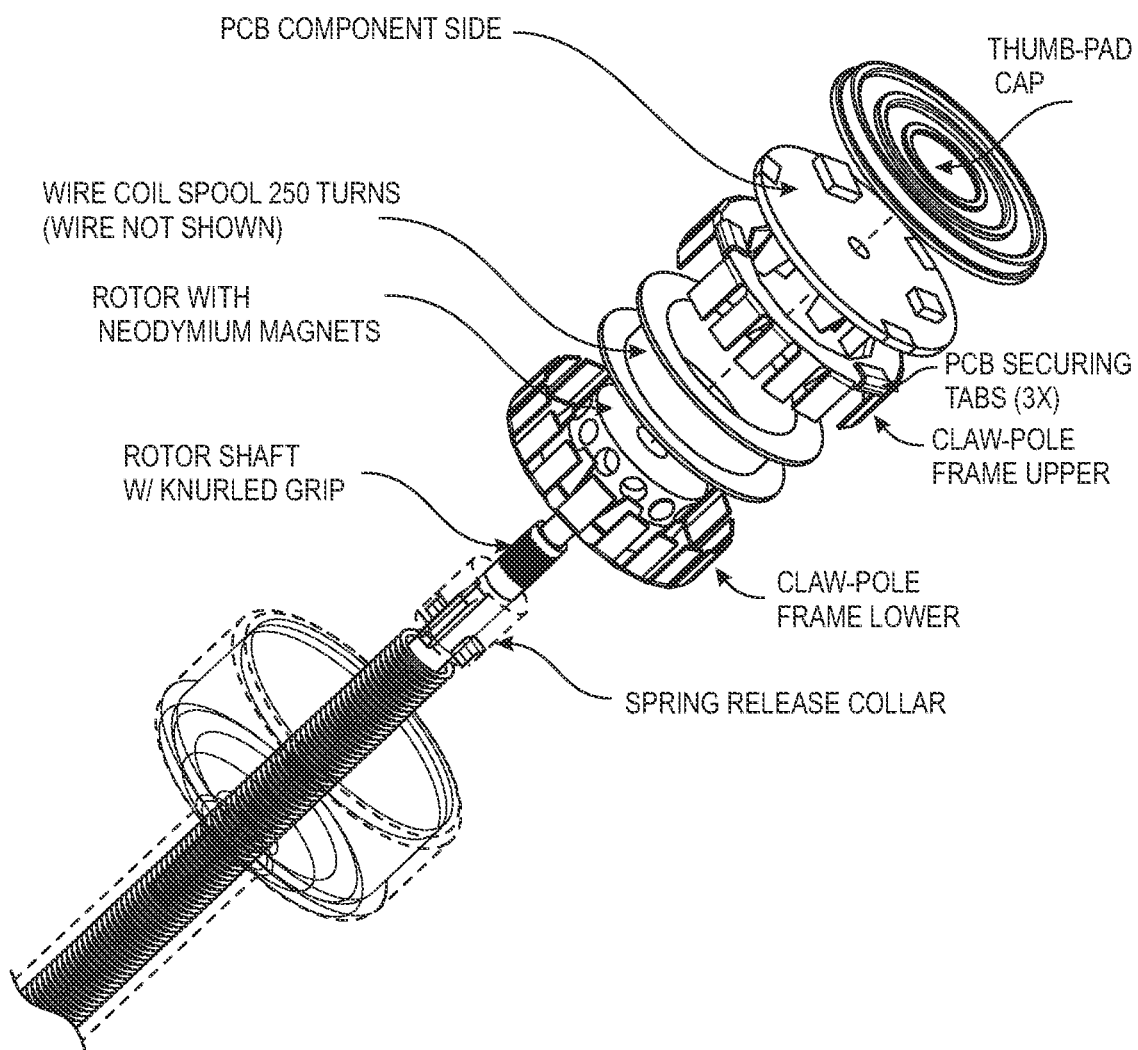
FIG. 49 is a three dimensional exploded view rendering of the claw-pole microgenerator shown in FIG. 48.
Figure 50:
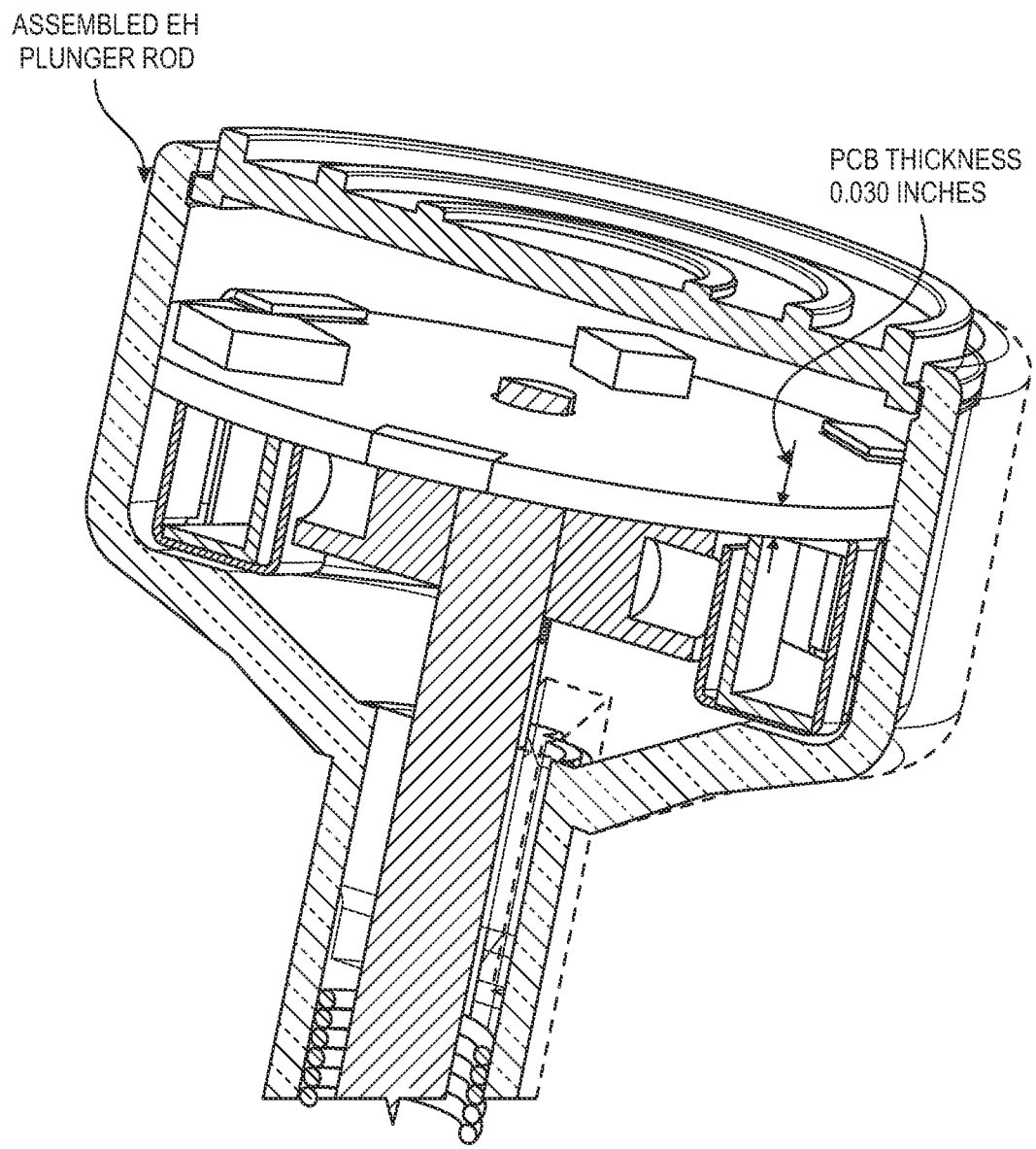
FIG. 50 is an enlarged three dimensional rendering of the proximal head portion of the claw-pole microgenerator shown in FIG. 48.

Referring now to FIGS. 48-50, another exemplary embodiment of a claw-pole microgenerator similar to the one shown in FIG. 46 is provided. This design is optimized for deployment in a syringe plunger rod, as shown. In this embodiment, a torsion spring is located inside the shaft portion of the plunger. Its distal end is rotationally fixed to the plunger and its proximal end is coupled to an internal rotor of the microgenerator, which is located in the head portion of the plunger. The torsion spring may be wound during manufacture of the device and held in its charged state by a clutch release collar located at its proximal end as shown. The clutch release collar prevents the proximal end of the spring from rotating until its energy is to be released. The clutch release collar may be configured to slide longitudinally toward the plunger head when the plunger reaches its end of delivery (EOD) position, thereby automatically disengaging the proximal end of the spring and allowing it to release its stored energy to drive the microgenerator. FIG. 48 provides details on a spring that may be used in this exemplary embodiment.

To maximize the energy produced by the microgenerator, the inertia of the rotor may be decreased and the inertia of the spring/coupler may be increased. In conjunction with this configuration, a decoupling mechanism may be provided between the spring and the rotor to allow the rotor to freewheel once the spring has imparted its energy to it. In other embodiments, the proximal end of the torsion spring is rotationally fixed to the microgenerator rotor. This spring-mass-dampener arrangement allows the rotor to intentionally oscillate, changing rotation directions between oscillations.

Figure 51:
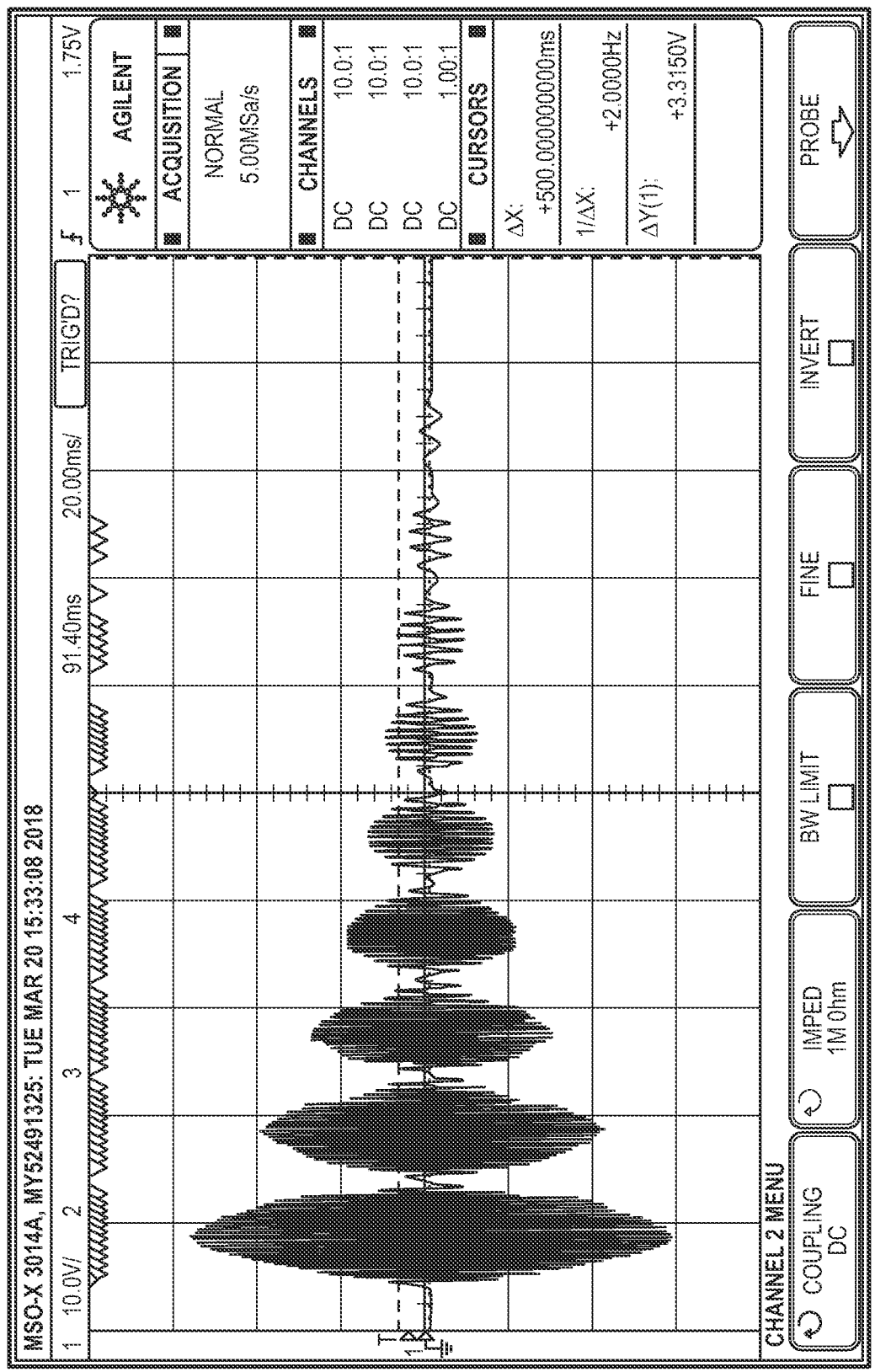
FIG. 51 is a photograph of an oscilloscope screen showing the voltage vs. time raw output of a claw-pole microgenerator according to one embodiment of the disclosure.
Figure 52:
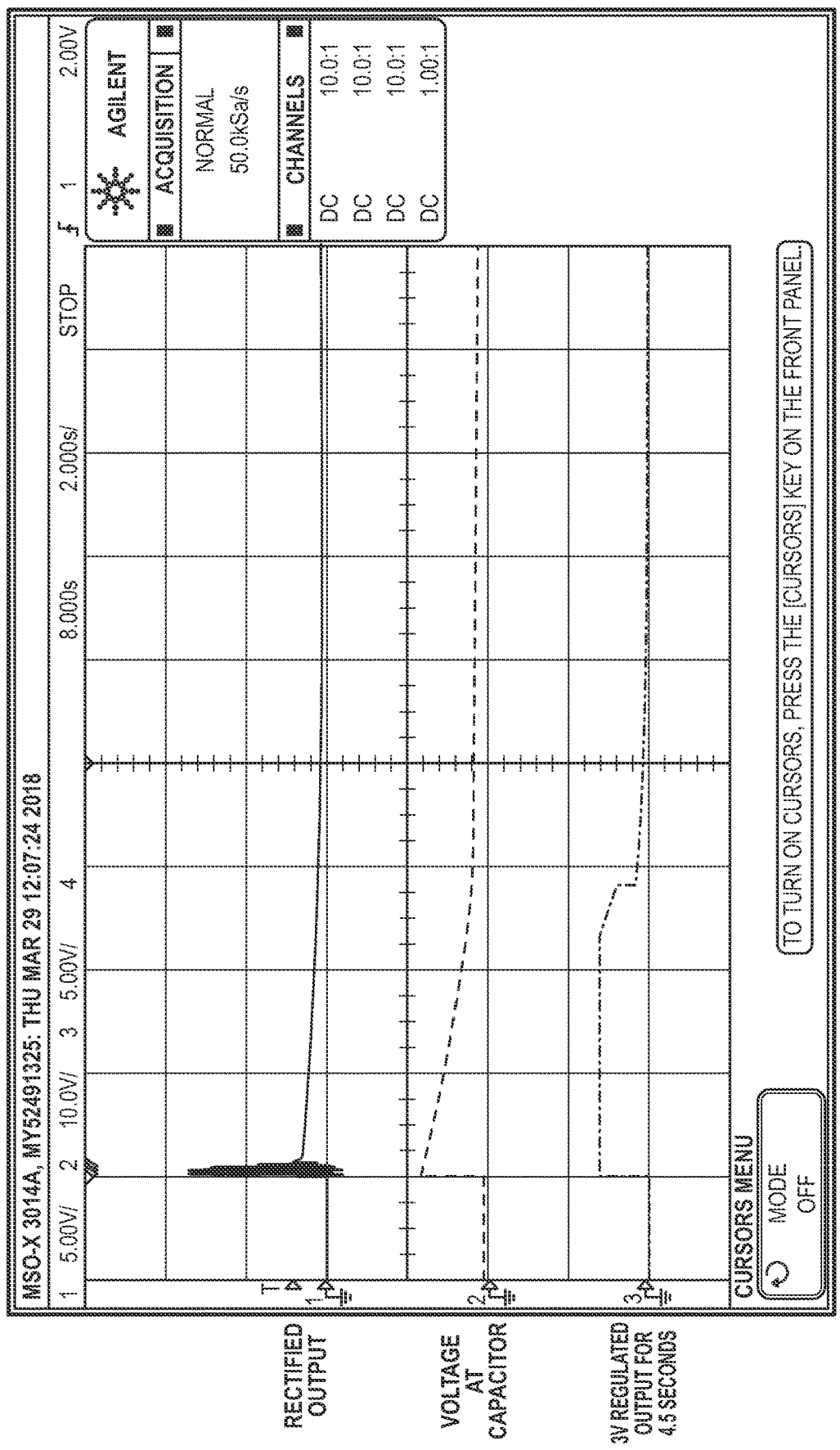
FIG. 52 is a photograph of an oscilloscope screen showing various voltage vs. time signals of a claw-pole microgenerator circuit according to one embodiment of the disclosure.

Referring now to FIGS. 51 and 52, electrical performance characteristics are provided for the exemplary embodiment shown in FIGS. 48-50. In this embodiment, the spring and rotor are designed to oscillate. A full-wave bridge rectifier may be added to a voltage regulation circuit to convert the generated AC voltage to DC. Capacitance may be added to the circuitry to capture the generated energy. In some embodiments, 3 volts is generated for 3 to 5 seconds from the energy harvested from the torsion spring. For the test results shown in FIG. 52, a 40 ohm coil and square magnets were used, producing a resistance of 10 ohms, a load test raw output of 4.6 volts, a current of 0.46 amps and a power of 0.21 watts. A 3/32 inch diameter rod inside the spring and a softer spring than shown in FIG. 48 with 11 turns were also used. In other embodiments (not shown), a planetary geared system may be used to increase the load on the spring and increase the speed of the rotor.

Battery Segregation

Figure 53:
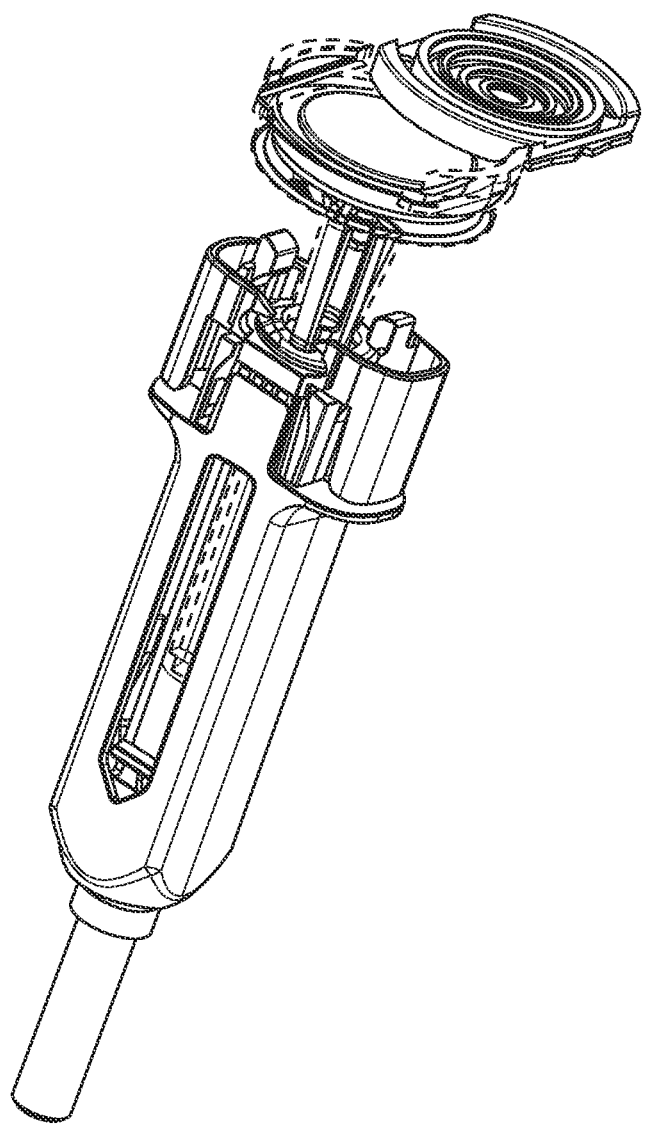
FIG. 53 is a three dimensional rendering of a smart syringe having a slide top battery segregation configuration according to one embodiment of the disclosure.
Figure 54:
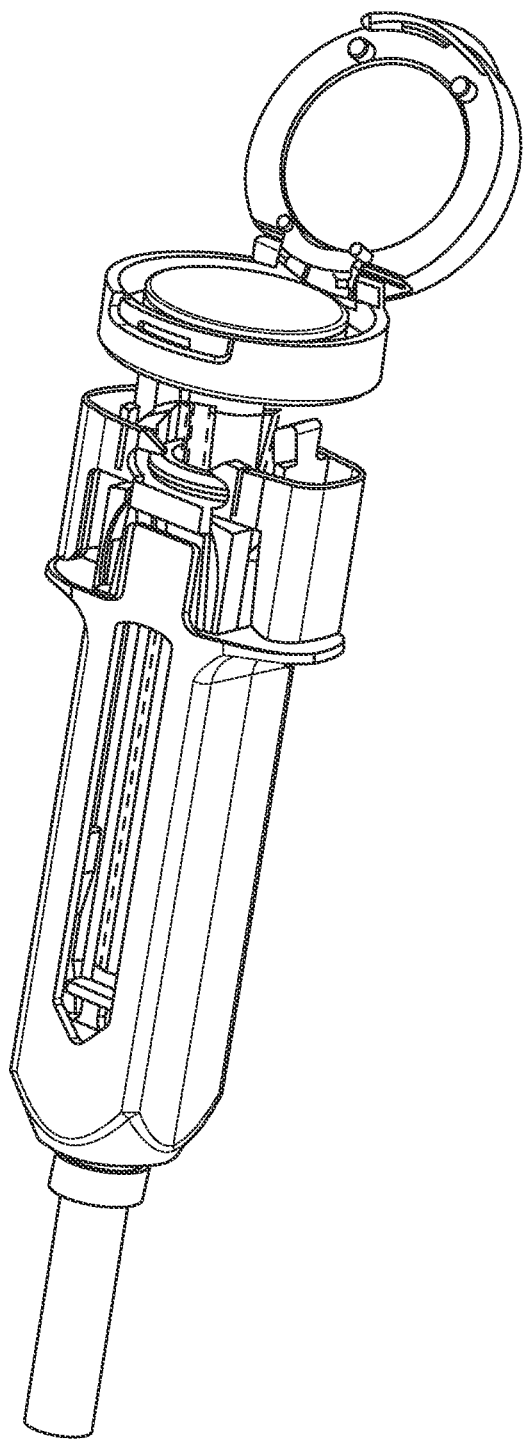
FIG. 54 is a three dimensional rendering of a smart syringe having a flip top battery segregation configuration according to one embodiment of the disclosure.
Figure 55:
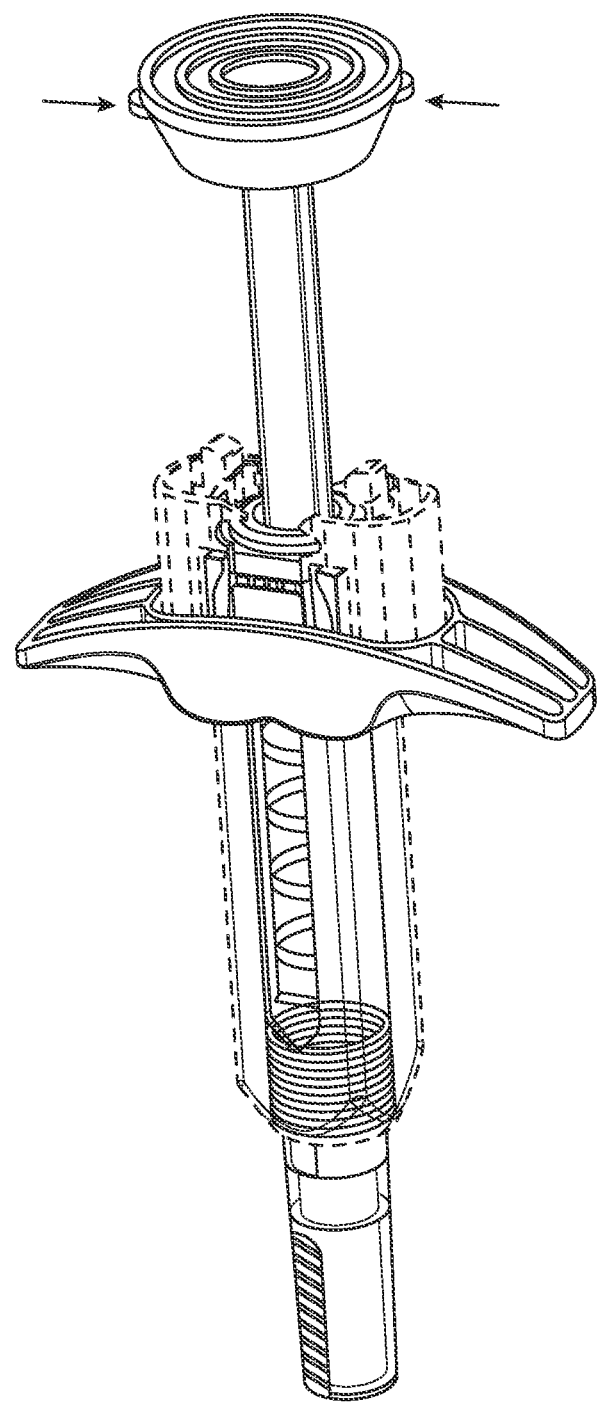
FIG. 55 is a three dimensional rendering of a smart syringe having an oval pop top battery segregation configuration according to one embodiment of the disclosure.
Figure 56:
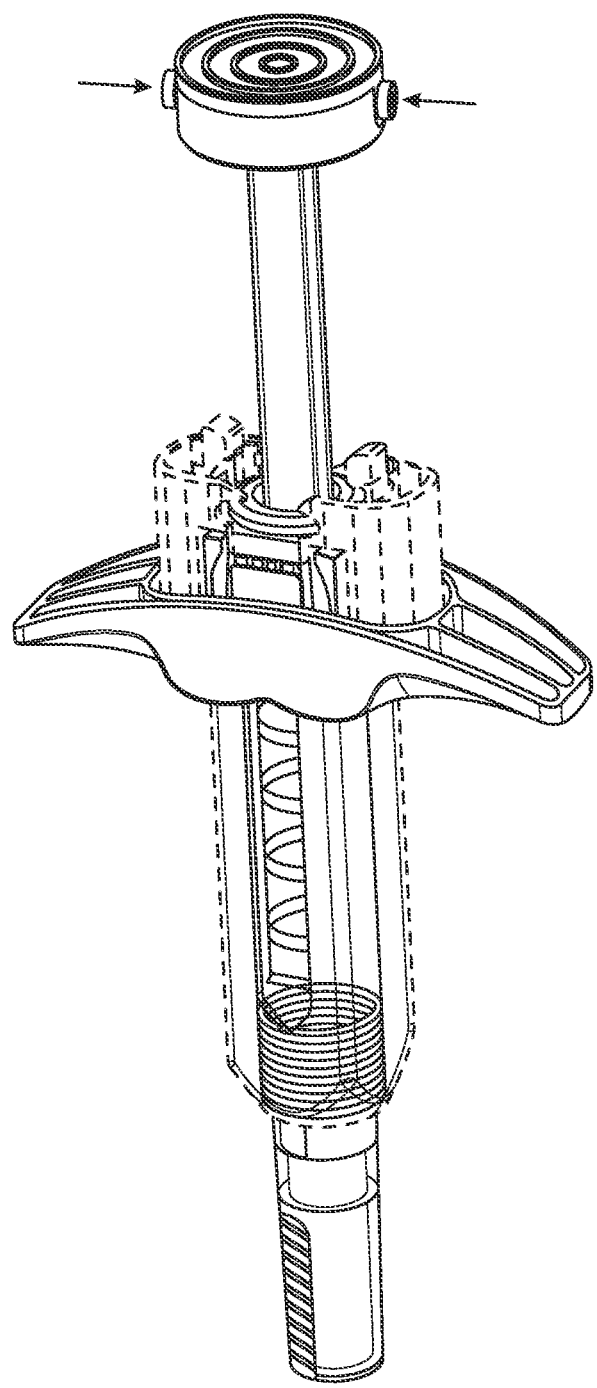
FIG. 56 is a three dimensional rendering of a smart syringe having a round pop top battery segregation configuration according to one embodiment of the disclosure.
Figure 57:
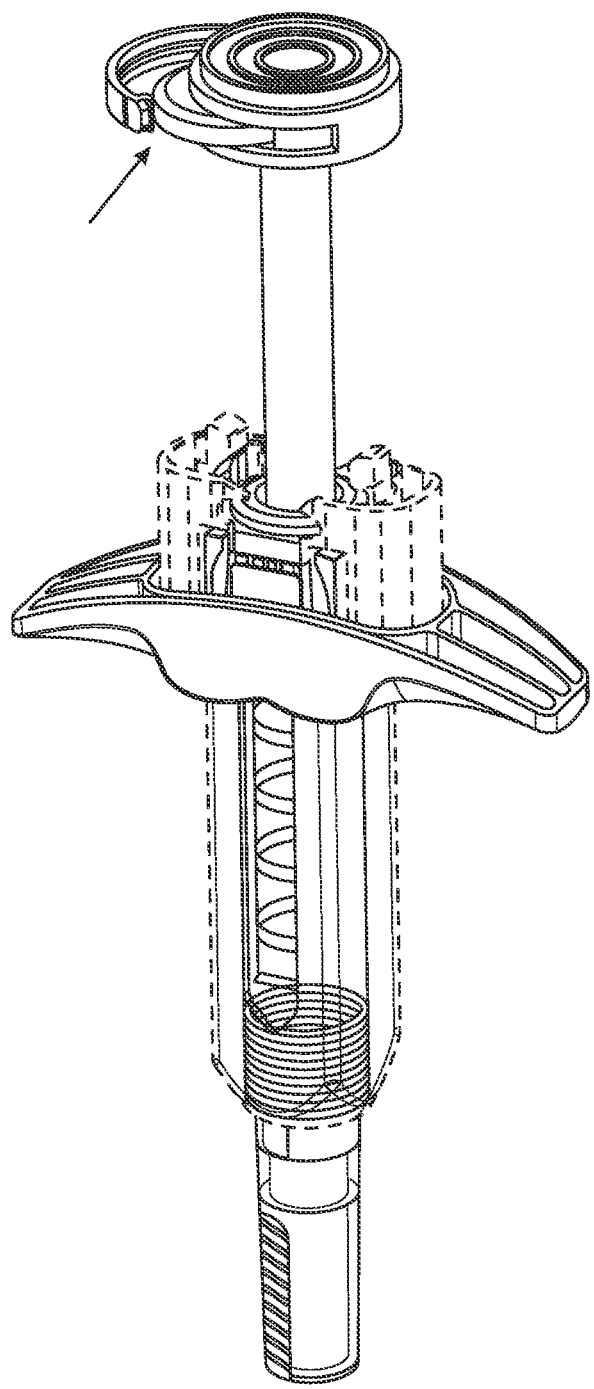
FIG. 57 is a three dimensional rendering of a smart syringe having a side flip-out eject battery segregation configuration according to one embodiment of the disclosure.

For embodiments of the disclosure that utilize a battery, aspects of the disclosure include various configurations for segregating the battery from other components of the device. Referring to FIGS. 53-57, various exemplary embodiments are provided. In each of these embodiments, the battery is located in the head portion of the syringe plunger as is easily accessible so the user may remove the battery before disposing of the device. FIG. 53 shows a slide top configuration in which the top slides open to expose and remove the battery. FIG. 54 shows a flip top configuration in which the top rotates open to expose and remove the battery. FIG. 55 shows an oval pop top configuration in which the sides are squeezed together in order to release the top. FIG. 56 shows a round pop top configuration in which the sides are squeezed together in order to release the top. FIG. 57 shows a side flip-out eject configuration in which a fingertip is used to flip an ejection lever to eject the battery as shown.

Methods of Use

Aspects of the disclosure include methods for operating the subject drug delivery systems and devices to deliver a drug dose to a patient, and to record information relating to the drug dose administration in a data management component. In some embodiments, the subject methods comprise verifying one or more operational states of a subject system or device prior to administering the drug dose to the patient. In some embodiments, the subject methods comprise authenticating a drug in a subject system or device prior to administering the drug to the patient.

In one embodiment, a subject method comprises inserting a drug delivery cannula of a subject drug delivery system into a patient and completing a delivery stroke of the actuation component, thereby causing the deflection component to generate a delivery signature that is detected by the sensor. In response to detect of the delivery signature, a wireless transmitter module in the sensor component transmits a report comprising a drug dose completion signal to the data management system. Upon receipt of the report, the data management system records administration of the drug dose to the patient. By automating this step, the user is ensured of more accurate record keeping regarding administration of the drug. In addition, other parties, such as a treating physician or health care network, can have greater access to more accurate information regarding the patient's medical record, e.g., the history of administration of the drug.

In some embodiments, the subject methods comprise a validation or verification step in which one or more data values are received from the subject drug delivery systems or devices, and are validated or verified to determine whether the drug is suitable for administration to the a patient. In some embodiments, the subject methods comprise verification of one or more drug identification characteristics, e.g., a drug identification number, in order to confirm the authenticity of the drug. In some embodiments, the subject methods comprise analyzing a plurality of data collected from the sensor component of a subject drug delivery system or device to evaluate one or more environmental parameters. For example, in one embodiment, the subject methods comprise analyzing the temperature history of a drug reservoir to verify that the drug reservoir has been maintained under required temperature conditions prior to administration of the drug to the patient. By including a sensor component on the subject systems and devices, many of the steps associated with verifying the authenticity and condition of a given drug can be done automatically using a data management component, providing greater ease of use to the end user, and providing more accurate safety and administration information.

In some embodiments, the subject methods comprise utilizing a computer application (e.g., a mobile application) on a subject data management component that is configured or adapted to facilitate improved patient adherence to a drug dosage regimen by recording the date and time of each administration of a drug to the patient. In some embodiments, the methods involve recording the date and time of each administration of a drug dose to the patient so that the patient can be accurately reminded when the next administration of the drug dose should take place in accordance with a prescribed drug dose regimen. In some embodiments, the subject methods involve sending a reminder to a patient that a drug dose is due to be administered at a designated time. For example, in some embodiments, the subject methods involve sending one or more regularly-scheduled reminders to the patient to administer a dose of a drug. In some embodiments, the subject methods comprise sending a reminder to the patient at a predetermined time, e.g., every day at a specific time. In some embodiments, the subject methods involve determining when a subsequent dose of a drug is due to be administered to a patient based on the patient's prior administrations of the drug, and sending a reminder to the patient at a predetermined time, (e.g., about 1 hour, about 30 minutes, or about 10 minutes) before the drug dose is due to be administered. In some embodiments, the subject methods involve monitoring a patient's adherence to a drug dosage regimen, and sending a notification to one or more third parties if the patient is not adequately adhering to the dosage regimen. For example, in some embodiments, the subject methods comprise sending a notification to one or more members of a patient's family if the patient is not adhering to the dosage regimen. In some embodiments, the subject methods comprise sending a notification to one or more health care providers (e.g., to a prescribing physician) if the patient is not adhering to a dosage regimen.

Aspects of the disclosure include Internet-based computing techniques (also known as "cloud computing" techniques) that involve sending and/or receiving information to or from one or more shared computer processing resources and/or data repositories over the Internet at the time such resources are needed or used by a user. Such techniques allow a user to utilize sophisticated computing equipment without being required to personally purchase and maintain the equipment. In addition, Internet-based computing techniques facilitate access to user information by patient-authorized third parties, such as, e.g., health care providers, or drug manufacturers.

In some embodiments, the subject methods comprise sending one or more drug identification characteristics to a remote database, and receiving, in response, one or more additional drug identification characteristics that can be recorded by the data management system. For example, in one embodiment, the subject methods comprise receiving a first drug identification characteristic (e.g., a drug lot number) from a subject system or device, and transmitting the first drug identification characteristic to a remote database using the data management component. The remote database uses the first drug identification characteristic to retrieve one or more additional drug identification characteristics, which are then transmitted back to the data management component.

Aspects of the disclosure relate to methods for monitoring the progress of a clinical trial. In some embodiments, the subject drug delivery systems and devices can be used to electronically track one or more individual patients in a clinical trial, and to record one or more items of information associated with each administration of a drug. For example, in some embodiments, the subject drug delivery systems and devices can be used to monitor the progress of a clinical trial while providing adequate protection of the rights of any human subjects involved the clinical trial by rendering the data anonymous to any personnel who are administering the trial. The subject systems and devices can be used to transmit and/or store information relating to successful administration of a drug dose to a patient, and the information can be reviewed by personnel administering the clinical trial to monitor the progress of the clinical trial. In some embodiments, the subject systems and devices can be used to record one or more drug identification characteristics, such as, e.g., a drug lot number, for each patient in a clinical trial. At any point during the progress of the trial, and/or at the completion of the trial, the drug identification information can be used to analyze the results of the trial, e.g., to determine patient response as a function of one or more drug identification characteristics.

In some embodiments, the subject methods result in improved patient adherence to a drug dosage regimen. For example, in some embodiments, implementation of the subject methods, as described above, results in an increase in patient adherence to a drug dosage regimen by an amount that ranges from about 1% up to about 75% or more, such as about 2%, 3%, 4%, 5%, 6%, 7%, 8%, 9%, 10%, 15%, 20%, 25%, 30%, 35%, 40%, 45%, 50%, 55%, 60%, 65%, or about 70% or more.

In some embodiments, the subject methods comprise separating one or more components of the subject systems and devices following administration of the drug to the patient, and separately disposing of the individual components. For example, in one embodiment, a portion of a subject system or device that comprises electronic components (e.g., a circuit board component, a power component, etc.) can be separated from the remainder of the device and disposed of according to electronic waste handling procedures. Separation of the electronic components from the remainder of the device reduces the amount of electronic waste, as the non-electronic components (e.g., the housing, the drug reservoir, etc.) can be disposed of separately.

Similarly, in some embodiments, a portion of a subject system or device that comprises biohazardous waste (e.g., a drug delivery cannula, a drug reservoir, etc.) can be separated from the remainder of the device and disposed of according to biohazardous waste handling procedures. Separation of the biohazardous waste from the remainder of the device reduces the amount of biohazardous waste, as the non-biohazardous components (e.g., the electronic components) can be disposed of separately.

The following examples are offered for illustrative purposes only, and are not intended to limit the scope of the present disclosure in any way. While several embodiments have been provided in the present disclosure, it should be understood that the disclosed systems and methods might be embodied in many other specific forms without departing from the scope or spirit of the present disclosure. The present examples are to be considered as illustrative and not restrictive, and the intention is not to be limited to the details given herein. Various examples of changes, substitutions, and alterations are ascertainable by one skilled in the art and could be made without departing from the scope and spirit disclosed herein.

All references cited throughout the specification are expressly incorporated by reference herein.

Example 1: Measurement of Inductance Profiles from Detection Targets

Figure 58A:
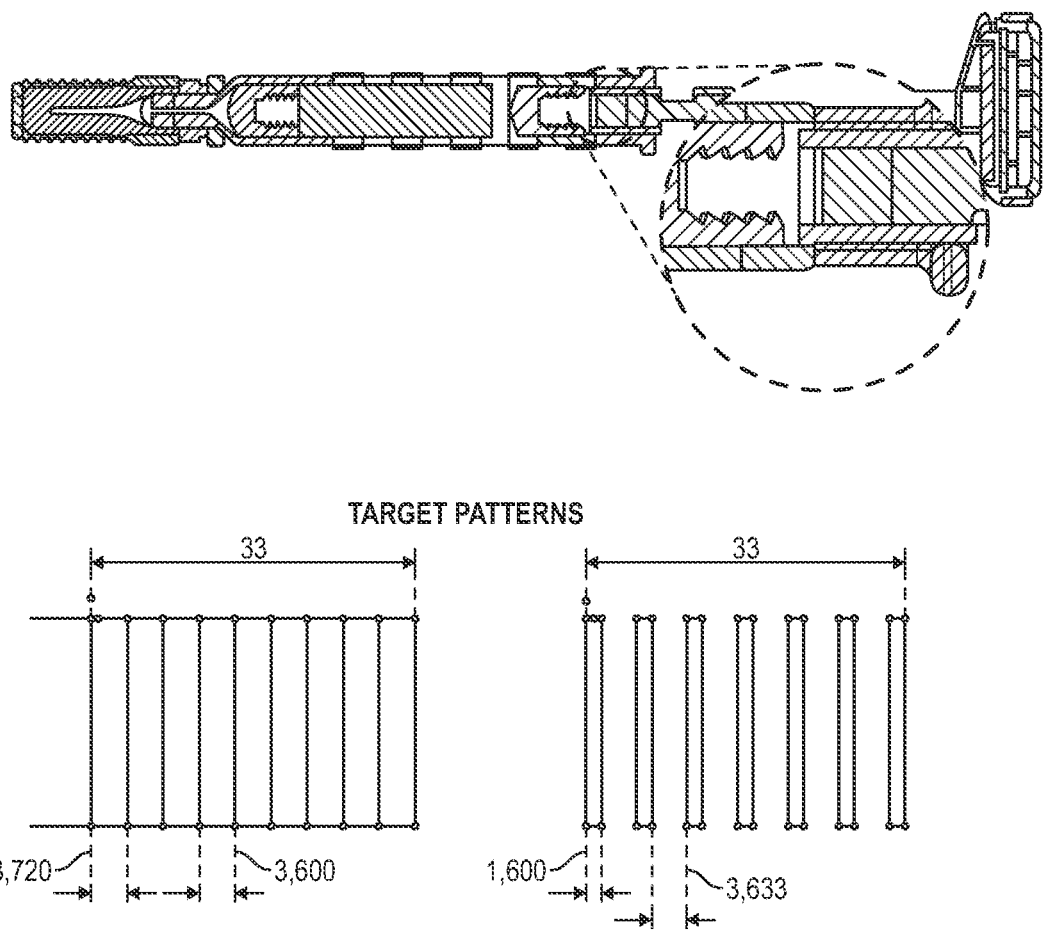
FIG. 58A is a diagram depicting a device in accordance with one embodiment of the disclosure. Exemplary detection target patterns are shown.
Figure 58B:
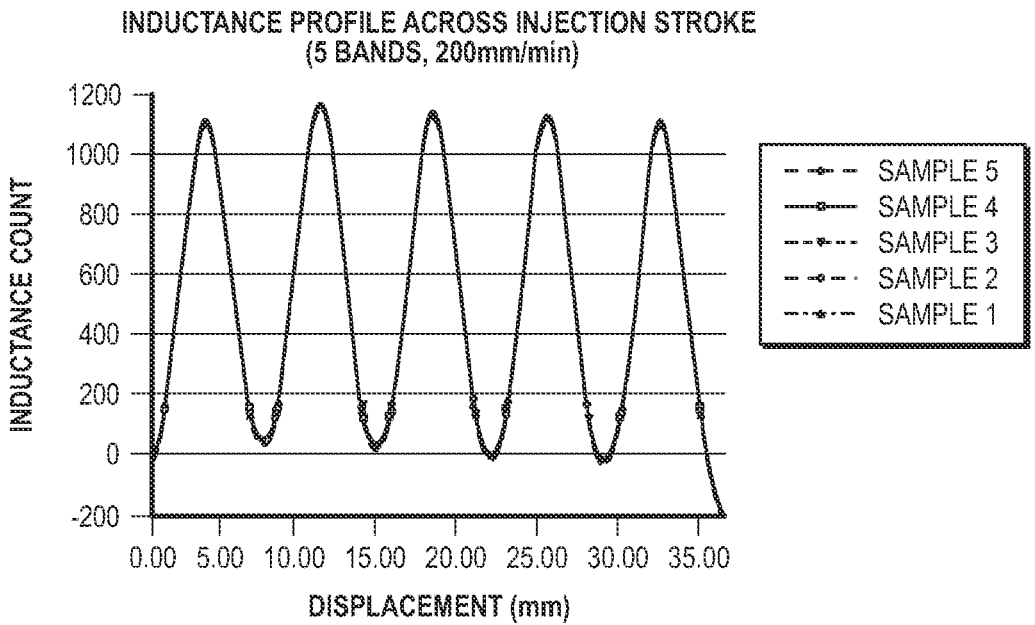
FIG. 58B is a graph showing inductance count as a function of displacement for five different samples, each being injected at a rate of 200 mm/min.
Figure 58C:
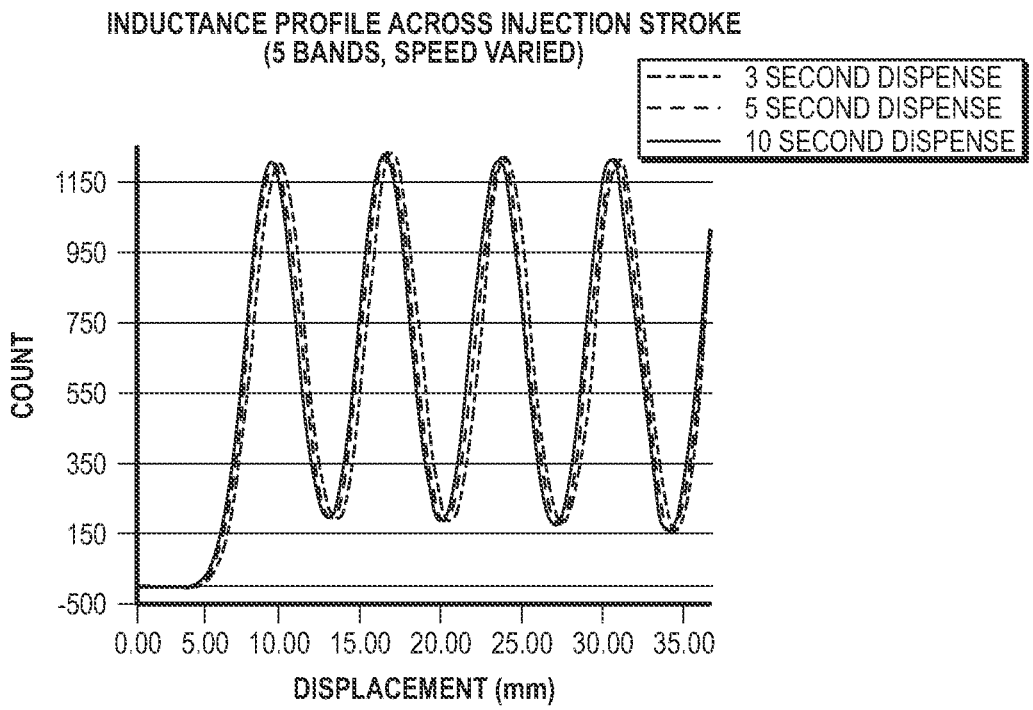
FIG. 58C is a graph showing inductance count as a function of displacement for three samples injected at varying dispensation speeds.

A system comprising a deflection component with an inductive sensor coil disposed on an extension component (as depicted in FIGS. 8-13) was used to analyze an inductance count as a function of displacement through the barrel of a glass syringe. Two detection targets, shown in FIG. 58, Panel A, were tested. The detection targets comprised a repeating pattern of 5 foil bands that were disposed on the surface of the syringe barrel, having the depicted dimensions. To test the inductance profile that could be read from the detection targets, the inductive sensor coil was first passed into and through the syringe barrel at a constant speed of 200 mm/min, and the inductance count was measured. The process was repeated for five different samples, and the results are shown in FIG. 58, Panel B. As shown in the graph, the inductance count varied geometrically in response to the inductive sensor coil passing by each of the bands on the detection target, and was highly reproducible.

Next, the inductance profile was tested using different injection speeds. The injection durations tested were 3, 5, and 10 seconds, each for the same injection distance, thereby resulting in 3 different injection speeds. The results are provided in FIG. 58, Panel C. As shown in the graph, the inductance count as a function of displacement position was highly repeatable for all three injection speeds, demonstrating that the inductance count obtained from the tested detection targets could be reliably used as a delivery signature over a range of injection speeds. These results demonstrate that the combination of an inductive sensor coil disposed within the syringe stopper rod and a detection target located on the syringe barrel could be used in an accurate and reproducible manner to generate an inductance profile that could be used as a delivery signature to verify successful completion of a delivery stroke.

What is claimed is:

1. A syringe stopper rod comprising:
   a sensor comprising a wireless transmitter module;
   a deflection component configured to generate a delivery signature in response to a delivery stroke of the syringe stopper rod; and
   at least one internal trigger switch contact assembly,
   wherein the wireless transmitter module is configured to transmit a report comprising a drug dose completion signal when the sensor detects the delivery signature,
   wherein the deflection component comprises:
     a plurality of trigger switches that are configured to deflect in an inward direction when compressed by a syringe barrel and make contact with the internal trigger switch contact assembly; and
     a circuit board component disposed on the stopper rod and configured to separately detect an inward deflection of each trigger switch.

2. The syringe stopper rod according to claim 1, wherein the internal trigger switch contact assembly is disposed between a trigger switch and an internal circuit board component.

3. The syringe stopper rod according to claim 1, wherein the circuit board component comprises a conductive rubber switch pad.

4. The syringe stopper rod according to claim 1, comprising at least two trigger switches that are disposed on a first side of the stopper rod.

5. The syringe stopper rod according to claim 4, further comprising one or more centering components disposed on a second side of the stopper rod, opposite the at least two trigger switches.

6. The syringe stopper rod according to claim 4, wherein the syringe stopper rod comprises at least four trigger switches, wherein at least two trigger switches are disposed on a first side of the syringe stopper rod, and at least two trigger switches are disposed on a second, opposite side of the syringe stopper rod.

7. The syringe stopper rod according to claim 6, wherein each of the at least two trigger switches on the first side of the syringe stopper rod is disposed at the same longitudinal position along the syringe stopper rod as each of the at least two trigger switches on the second, opposite side of the syringe stopper rod.

8. The syringe stopper rod according to claim 6, wherein each of the at least two trigger switches on the first side of the syringe stopper rod is disposed at a different longitudinal position along the syringe stopper rod than each of the at least two trigger switches on the second, opposite side of the syringe stopper rod.

9. The syringe stopper rod according to claim 1, comprising at least two trigger switches, wherein one trigger switch is disposed on a first side of the stopper rod, and one trigger switch is disposed on a second, opposite side of the stopper rod.

10. The syringe stopper rod according to claim 9, wherein each of the at least two trigger switches is disposed at the same longitudinal position along the syringe stopper rod.

11. The syringe stopper rod according to claim 9, wherein each of the at least two trigger switches is disposed at a different longitudinal position along the syringe stopper rod.

12. The syringe stopper rod according to claim 1, wherein the syringe stopper rod comprises a first material, and the trigger switches are integrated into the syringe stopper rod and comprise the first material.

13. The syringe stopper rod according to claim 12, wherein one or more trigger switches comprise a second material that is different from the first material.

14. The syringe stopper rod according to claim 12, wherein at least one trigger switch comprises an alignment component.

15. The syringe stopper rod according to claim 14, wherein the alignment component comprises a semi-circular tab.

16. The syringe stopper rod according to claim 1, wherein the trigger switches are integrated into an external trigger switch assembly that is separable from the syringe stopper rod.

17. The syringe stopper rod according to claim 16, wherein the syringe stopper rod comprises a first material, and the external trigger switch assembly comprises a second material that is different from the first material.

18. The syringe stopper rod according to claim 16, further comprising one or more deflection limiting components configured to limit a deflection range of one or more trigger switches.

19. The syringe stopper rod according to claim 18, wherein at least one deflection limiting component is disposed on the syringe stopper rod adjacent to each trigger switch.

20. The syringe stopper rod according to claim 19, wherein the deflection limiting component comprises a semi-circular tab.

21. The syringe stopper rod according to claim 1, wherein the delivery signature comprises a deflection order of the trigger switches, a deflection duration of each trigger switch, one or more time intervals corresponding to a time between a deflection of a first trigger switch and a deflection of a second trigger switch, or any combination thereof.

22. The syringe stopper rod according to claim 1, wherein the deflection component comprises a force sensor.

23. The syringe stopper rod according to claim 22, wherein the force sensor is an absolute force sensor.

24. The syringe stopper rod according to claim 22, wherein the force sensor is a relative force sensor.

25. The syringe stopper rod according to claim 22, wherein the deflection component comprises a circuit board sensor component comprising a first inductive sensor coil configured to move toward a first detection target in response to a force applied to the syringe stopper rod by a user.

26. The syringe stopper rod according to claim 25, wherein the first detection target is disposed on an internal surface of the syringe stopper rod.

27. The syringe stopper rod according to claim 25, wherein the first detection target is disposed on an external surface of the syringe stopper rod.

28. The syringe stopper rod according to claim 25, wherein the first detection target is disposed on a thumb pad.

29. The syringe stopper rod according to claim 25, wherein the first detection target comprises a conductive material.

30. The syringe stopper rod according to claim 25, wherein the delivery signature comprises an injection force profile applied to the syringe stopper rod by a user.

31. The syringe stopper rod according to claim 30, wherein the injection force profile comprises a break loose force, a glide force, an end of dose force, or any combination thereof.

32. The syringe stopper rod according to claim 31, wherein the injection force profile further comprises a first time interval and/or force magnitude associated with the break loose force, a second time interval and/or force magnitude associated with the glide force, and a third time interval and/or force magnitude associate the end of dose force.

33. The syringe stopper rod according to claim 32, wherein the injection force profile comprises a characteristic shape that is indicative of the delivery stroke.

* * * * *